(12) United States Patent
Stappenbeck et al.

(10) Patent No.: US 11,058,653 B2
(45) Date of Patent: Jul. 13, 2021

(54) COMPOSITIONS COMPRISING DESAMINOTYROSINE AND USES THEREOF TO ENHANCE TYPE I INTERFERON STIMULATION

(71) Applicant: Washington University, St. Louis, MO (US)

(72) Inventors: Thaddeus Stappenbeck, St. Louis, MO (US); Ashley Steed, St. Louis, MO (US); Gerard Kaiko, St. Louis, MO (US); George Christophi, St. Louis, MO (US)

(73) Assignee: Washington University, St. Louis, MO (US)

( * ) Notice: Subject to any disclaimer, the term of this patent is extended or adjusted under 35 U.S.C. 154(b) by 48 days.

(21) Appl. No.: 16/345,625

(22) PCT Filed: Oct. 26, 2017

(86) PCT No.: PCT/US2017/058478
§ 371 (c)(1),
(2) Date: Apr. 26, 2019

(87) PCT Pub. No.: WO2018/081388
PCT Pub. Date: May 3, 2018

(65) Prior Publication Data
US 2019/0274983 A1    Sep. 12, 2019

Related U.S. Application Data

(60) Provisional application No. 62/413,241, filed on Oct. 26, 2016.

(51) Int. Cl.
| | | |
|---|---|---|
| *A01N 27/00* | (2006.01) | |
| *A61K 31/015* | (2006.01) | |
| *A61K 31/192* | (2006.01) | |
| *A61P 1/04* | (2006.01) | |
| *A61P 31/16* | (2006.01) | |
| *A61K 31/708* | (2006.01) | |
| *C07K 14/555* | (2006.01) | |

(52) U.S. Cl.
CPC .......... *A61K 31/192* (2013.01); *A61K 31/708* (2013.01); *A61P 1/04* (2018.01); *A61P 31/16* (2018.01); *C07K 14/555* (2013.01)

(58) Field of Classification Search
None
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,099,060 A | 3/1992 | Kohn et al. |
| 5,264,618 A | 11/1993 | Feigner et al. |
| 5,670,602 A | 9/1997 | Kohn et al. |
| RE37,160 E | 5/2001 | Kohn et al. |
| 7,888,317 B2 | 2/2011 | Drucker |
| 7,939,313 B2 | 5/2011 | Heyduk et al. |
| 2004/0116504 A1 | 6/2004 | Elokdah et al. |
| 2010/0081129 A1 | 4/2010 | Belouchi et al. |
| 2013/0261058 A1 | 10/2013 | Schally et al. |
| 2016/0069905 A1 | 3/2016 | Hains et al. |
| 2016/0297861 A1 | 10/2016 | Poelstra et al. |
| 2020/0165677 A1 | 5/2020 | Stappenbeck et al. |

FOREIGN PATENT DOCUMENTS

| | | |
|---|---|---|
| WO | 2017189846 A1 | 11/2017 |
| WO | 2018081388 A1 | 5/2018 |
| WO | 2019018571 A1 | 1/2019 |

OTHER PUBLICATIONS

Lin et al. (2012). Toll-like receptor 3 ligand polyinosinic: polycytidylic acid promotes wound healing in human and murine skin. Journal of Investigative Dermatology, 132(8), 2085-2092.*
International Search Report and Written Opinion dated Feb. 12, 2018 from related Patent Application No. PCT/US2017/058478; 8 pgs.
International Search Report and Written Opinion dated Jul. 31, 2017 from related Patent Application No. PCT/US2017/029836; 11 pgs.
Jostins, L. et al., "Host-microbe interactions have shaped the genetic architecture of inflammatory bowel disease," HHS Public Access Author Manuscript, May 1, 2013, pp. 1-18, published in final edited form as: Nat., Nov. 1, 2012, pp. 119-124, vol. 491, No. 7422.
Jung, C. et al., "mTOR regulation of autophagy," FEBS Lett., 2010, pp. 1287-1295, vol. 584.
Kaiko, G. et al., "The Colonic Crypt Protects Stem Cells from Microbiota- Derived Metabolites," Cell, 2016, pp. 1708-1720, vol. 165.
Kanayama, M. et al., "Autophagy enhances NFkB activity in specific tissue macrophages by sequestering A20 to boost antifungal immunity," Nat. Commun., 2015, pp. 1-14, vol. 6, No. 5779.
Kaser, A. et al., "XBP1 Links ER Stress to Intestinal Inflammation and Confers Genetic Risk for Human Inflammatory Bowel Disease," Cell, Sep. 5, 2008, pp. 743-756, vol. 134, Elsevier Inc.
Kawai, Y. et al., "Japonica array: improved genotype imputation by designing a population-specific SNP array with 1070 Japanese individuals," J. Hum. Genet., 2015, pp. 581-587, vol. 60.

(Continued)

*Primary Examiner* — Patrick T Lewis
(74) *Attorney, Agent, or Firm* — Polsinelli PC

(57) ABSTRACT

The disclosure provides compositions comprising desaminotyrosine and methods of use thereof in enhancing type I interferon stimulation, epithelial proliferation, and treatment of inflammatory bowel disease.

19 Claims, 68 Drawing Sheets
(31 of 68 Drawing Sheet(s) Filed in Color)
Specification includes a Sequence Listing.

(56) References Cited

OTHER PUBLICATIONS

Kernbauer, E. et al., "An enteric virus can replace the beneficial function of commensal bacteria," Europe PMC Funders Group Public Access Author Manuscript, Jun. 4, 2015, pp. 1-32, Published in final edited form as: Nature, Dec. 4, 2014, pp. 94-98, vol. 516, No. 7529.
Khajah, M. et al., "Fer Kinase Limits Neutrophil Chemotaxis toward End Target Chemoattractants," J. Immunol., 2013, pp. 2208-2216, vol. 190.
Khor, B. et al., "Genetics and pathogenesis of inflammatory bowel disease," NIH Public Access Author Manuscript, Dec. 16, 2011, pp. 1-25, published in final edited form as: Nat., Jun. 16, 2011, pp. 307-317, vol. 474, No. 7351.
Knights, D. et al., "Bayesian community-wide culture-independent microbial source tracking," Nat. Methods, Sep. 2011, pp. 761-763, vol. 8, No. 9.
Knights, D. et al., "Supervised classification of microbiota mitigates mislabeling errors," ISME J., 2011, pp. 570-573, vol. 5.
Ko, Y. et al., "Epidemiological studies of migration and environmental risk factors in the inflammatory bowel diseases," World J. Gastroenterol., Feb. 7, 2014, pp. 1238-1247, vol. 20, No. 5, Baishideng Publishing Group Co., Limited, Hong Kong.
Kobayashi, T. et al., "Dysbiosis and *Staphylococcus aureus* Colonization Drives Inflammation in Atopic Dermatitis," Immunity, Apr. 2015, pp. 756-766, vol. 42, Elsevier Inc.
Koerner, I. et al., "Protective Role of Beta Interferon in Host Defense against Influenza A Virus," J. Virol, Feb. 2007, pp. 2025-2030, vol. 81, No. 4.
Kolho, K-L. et al., "Fecal Microbiota in Pediatric Inflammatory Bowel Disease and Its Relation to Inflammation," Am. J. Gastroenterol., 2015, pp. 921-930, vol. 110.
Kolumam, G. et al., "Type I interferons act directly on CD8 T cells to allow clonal expansion and memory formation in response to viral infection," J. Exp. Med., Sep. 5, 2005, pp. 637-650, vol. 202, No. 5.
Kostic, A. et al., "The Microbiome in Inflammatory Bowel Disease: Current Status and the Future Ahead," NIH Public Access Author Manuscript, May 1, 2015, pp. 1-19, published in final edited form as: Gastroenterol., May 2014, pp. 1489-1499, vol. 146, No. 6.
Koutroubakis, L. et al., "Genetic Risk Factors in Patients With Inflammatory Bowel Disease and Vascular Complications: Case-Control Study," Inflamm. Bowel Dis., Apr. 2007, pp. 410-415, vol. 13, No. 4, Wiley InterScience.
Lassen, K. et al., "Atg16L1 T300A variant decreases selective autophagy resulting in altered cytokine signaling and decreased antibacterial defense," PNAS, May 27, 2014, pp. 7741-7746, vol. 111, No. 21.
Lee, J. et al., "Genome-wide association study identifies distinct genetic contributions to prognosis and susceptibility in Crohn's disease," Europe PMC Funders Group Author Manuscript, Dec. 14, 2017, pp. 1-19, published in final edited form as: Nat Genet., Feb. 2017, pp. 262-268, vol. 49, No. 2.
Levine, A. et al., "Pediatric Modification of the Montreal Classification for Inflammatory Bowel Disease: The Paris Classification," Inflamm. Bowel Dis., Jun. 2011, pp. 1314-1321, vol. 17, No. 6.
Levine, B. et al., "Autophagy in immunity and inflammation," NIH Public Access Author Manuscript, Jul. 20, 2011, pp. 1-28, published in final edited form as: Nat., Jan. 20, 2011, pp. 323-335, vol. 469, No. 7330.
Lewis, J. et al., "Inflammation, Antibiotics, and Diet as Environmental Stressors of the Gut Microbiome in Pediatric Crohn's Disease," Cell Host Microbe, Oct. 2015, pp1 489-500, vol. 18.
Li, X. et al., "Risk of inflammatory bowel disease in first- and second-generation immigrants in Sweden: A nationwide follow-up study," Inflamm. Bowel Dis., Aug. 2011, pp. 1784-1791, vol. 17, No. 8.
Liu, B. et al., "Irgm1-deficient mice exhibit Paneth cell abnormalities and increased susceptibility to acute intestinal inflammation," Am. J. Physiol. Gastrointest. Liver Physiol., 2013, pp. G573-G584, vol. 305.
Liu, J. et al., "Association analyses identify 38 susceptibility loci for inflammatory bowel disease and highlight shared genetic risk across populations," Nat. Genet., Sep. 2015, pp. 979-986, vol. 47, No. 9.
Liu, T-C. et al., "LRRK2 but not ATG16L1 is associated with Paneth cell defect in Japanese Crohn's disease patients," JCI Insight, 2017, pp. 1-14, vol. 2, No. 6, e91917.
Liu, T-C. et al., "Paneth cell defects in Crohn's disease patients promote dysbiosis," JCI Insight, 2016, pp. 1-15, vol. 1, No. 8, e86907.
Liu, T-C. et al., "Spatial and Temporal Stability of Paneth Cell Phenotypes in Crohn's Disease: Implications for Prognostic Cellular Biomarker Development," NIH Public Access, Author Manuscript, Apr. 1, 2015, pp. 1-16, published in final edited form as: Inflamm. Bowel Dis., Apr. 2014, pp. 646-651, vol. 20, No. 4.
Lu, W. et al., "Functional intersection of Human Defensin 5 with the TNF receptor pathway," FEBS Lett., 2014, pp. 1906-1912, vol. 588.
Manichanh, C. et al., "Reduced diversity of faecal microbiota in Crohn's disease revealed by a metagenomic approach," Gut, 2006, pp. 205-211, vol. 55.
Matsumoto, M. et al., "Impact of Intestinal Microbiota on Intestinal Luminal Metabolome," Sci. Rep., 2012, pp. 1-10, vol. 2, No. 233.
McDonald, D. et al., "An improved Greengenes taxonomy with explicit ranks for ecological and evolutionary analyses of bacteria and archaea," ISME J., 2012, pp. 610-618, vol. 6.
McGovern, D. et al., "Genetics of Inflammatory Bowel Diseases," HHS Public Access Author Manuscript, Oct. 1, 2016, pp. 1-28, published in final edited form as: Gastroenterol., Oct. 2015, pp. 1163-1176.e2, vol. 149, No. 5.
Mu, C. et al., "The Colonic Microbiome and Epithelial Transcriptome Are Altered in Rats Fed a High-Protein Diet Compared with a Normal-Protein Diet," J. Nutr, Mar. 2016, pp. 474-483, vol. 146, No. 3.
Murthy, A. et al., "A Crohn's disease variant in Atg16l1 enhances its degradation by caspase 3," Nat., Feb. 2014, pp. 456-462, vol. 506.
Nagasaki, M., et al., "Rare variant discovery by deep whole-genome sequencing of 1,070 Japanese individuals," Nat. Commun., 2015, pp. 1-13, vol. 6, No. 8018.
NCBI GEO Accession No. GSE90102, dated Nov. 21, 2016; 2 pgs.
Netzel-Arnett, S. et al., "The Role of Matriptase, Urokinase-Type Plasminogen Activator, and SERPINE1 in Colitis Pathogensis," Gastroenterology, AGA Abstracts, May 2011, p. S-650, vol. 140, No. 5, Suppl. 1, Elsevier Inc.
Newby, C. et al., "The RNA Binding Domain of Influenza a Virus NS1 Protein Affects Secretion of Tumor Necrosis Factor Alpha, Interleukin-6, and Interferon in Primary Murine Tracheal Epithelial Cells," J. Virol., Sep. 2007, pp. 9469-9480, vol. 81, No. 17.
Nguyen, K. et al., "Coordinated and Distinct Roles for IFN-alpha beta, IL-12, and IL-15 Regulation of NK Cell Responses to Viral Infection," J. Immunol., 2002, pp. 4279-4287, vol. 169.
Palm, N. et al., "Immunoglobulin A Coating Identifies Colitogenic Bacteria in Inflammatory Bowel Disease," Cell, Aug. 2014, pp. 1000-1010, vol. 158, Elsevier, Inc.
"Paneth cell phenotype define a subtype of pediatric Crohn's disease through alterations in host-microbial interactions," Abstract presented at CCFA Annual Meeting, Dec. 10, 2015.
Patel, D. et al., "High Throughput Screening for Small Molecule Enhancers of the Interferon Signaling Pathway to Drive Next-Generation Antiviral Drug Discovery," PLoS One, May 2012, pp. 1-12, vol. 7, No. 5, e36594.
Perminow, G. et al., "Defective Paneth Cell-Mediated Host Defense in Pediatric Ileal Crohn's Disease," Am. J. Gastroenterol., Feb. 2010, pp. 452-459, vol. 105.
Platanias, L., "Mechanisms of Type-I- and Type-II-Interferon-Mediated Signalling," Nat. Rev. Immunol., May 2005, pp. 375-386, vol. 5.
Pobezinsky, L. et al., "Let-7 miRNAs target the lineage-specific transcription factor PLZF to regulate terminal NKT cell differentiation and effector function," HHS Public Access Author Manu-

(56) References Cited

OTHER PUBLICATIONS script, Nov. 1, 2015, pp. 1-24, published in final edited form as: Nat. Immunol., May 2015, pp. 517-524, vol. 15, No. 5.
Probert, C. et al., "Epidemiological study of ulcerative proctocolitis in Indian migrants and the indigenous population of Leicestershire," Gut, 1992, pp. 687-693, vol. 33.
Kohoutova, D. et al., "Prevalence of hypercoagulable disorders in inflammatory bowel disease," Scand. J. Gastro., 2014, pp. 287-294, vol. 49, No. 3.
UniProt Accession No. P00750, "Tissue-type plasminogen activator," Jul. 21, 1986; 21 pgs.
UniProt Accession No. P05121, "Plasminogen activator inhibitor 1," Aug. 13, 1987; 12 pgs.
Pruim, R. et al., "LocusZoom: regional visualization of genome-wide association scan results," Bioinformatics, 2010, pp. 2336-2337, vol. 26, No. 18, Oxford University Press.
Purcell, S. et al., "PLINK: A Tool Set for Whole-Genome Association and Population-Based Linkage Analyses," Am. J. Hum. Genet., Sep. 2007, pp. 559-575, vol. 81.
Qi, W. et al., "Absence of Fer protein tyrosine kinase exacerbates endotoxin induced intestinal epithelial barrier dysfunction in vivo," Gut, 2005, pp. 1091-1097, vol. 54.
Rogler, G. et al., "Exposome in IBD: Recent Insights in Environmental Factors that Influence the Onset and Course of IBD," Inflamm. Bowel Dis., Feb. 2015, pp. 400-408, vol. 21, No. 2.
Roulis, M. et al., "Host and microbiota interactions are critical for development of murine Crohn's-like ileitis," Mucosal Immunol., May 2016, pp. 787-797, vol. 9, No. 3.
Round, J. et al., "The gut microbiota shapes intestinal immune responses during health and disease," Nat. Rev. Immunol., May 2009, pp. 313-323, vol. 9, with Erratum, 1 pg., Macmillan Publishers Limited.
Rutgeerts, P. et al., "Predictability of the Postoperative Course of Crohn's Disease," Gastroenterology, 1990, pp. 956-963, vol. 99.
Ryu, S. et al., "Gut-Pancreatic Axis AMPlified in Islets of Langerhans," Immunity, Aug. 18, 2015, pp. 216-218, vol. 43.
Sadler, A. et al., "BTB-ZF transcriptional regulator PLZF modifies chromatin to restrain inflammatory signaling programs," PNAS, Feb. 3, 2015, pp. 1535-1540, vol. 112, No. 5.
Salzman, N. et al., "Enteric defensins are essential regulators of intestinal microbial ecology," HHS Publbic Access Author Manuscript, Jul. 1, 2010, pp. 1-22, published in final edited form as: Nat. Immunol., Jan. 2010, pp. 76-83, vol. 11, No. 1.
Salzman, N. et al., "Protection against enteric salmonellosis in transgenic mice expressing a human intestinal defensin," Nat., Apr. 3, 2003, pp. 522-526, vol. 422.
Sawdey, M. et al., "Regulation of murine type 1 plasminogen activator inhibitor gene expression in vivo. Tissue specificity and induction by lipopolysaccharide, tumor necrosis factor-alpha, and transforming growth factor-beta," J. Clin. Invest., Oct. 1991, pp. 1346-1353, vol. 88, No. 4.
Schaubeck, M. et al., "Dysbiotic gut microbiota causes transmissible Crohn's disease-like ileitis independent of failure in antimicrobial defence," Gut, 2016, pp. 225-237, vol. 65.
Schoefer, L. et al., "Anaerobic Degradation of Flavonoids by Clostridium orbiscindens," Appl. Environ. Microbiol., Oct. 2003, pp. 5849-5854, vol. 69, No. 10.
Schwiertz, A. et al., "Microbiota in Pediatric Inflammatory Bowel Disease," J. Pediatr., Aug. 2010, pp. 240-244.e1, vol. 157, No. 2.
Segata, N. et al., "Metagenomic biomarker discovery and explanation," Genome Biol., 2011, pp. 1-18, vol. 12, No. R60.
Shanahan, M. et al., "Mouse Paneth cell antimicrobial function is independent of Nod2," Gut, 2014, pp. 903-910, vol. 63.
Shanware, N. et al., "The PI3K, Metabolic, and Autophagy Networks: Interactive Partners in Cellular Health and Disease," Annu. Rev. Pharmacol. Toxicol., Jan. 2013, pp. 89-106, vol. 53.
Smith, P. et al., "The Microbial Metabolites, Short-Chain Fatty Acids, Regulate Colonic Treg Cell Homeostasis," Sci., Aug. 2, 2013, pp. 569-573, vol. 341, No. 6145.
Sokol, H. et al., "Faecalibacterium prausnitzii is an anti-inflammatory commensal bacterium identified by gut microbiota analysis of Crohn disease patients," PNAS, Oct. 28, 2008, pp. 16731-16736, vol. 105, No. 43.
Sorrentino, D., "State-of-the-art medical prevention of postoperative recurrence of Crohn's disease," Nat. Rev. Gastroenterol. Hepatol., Jul. 2013, pp. 413-422, vol. 10.
Soucie, E. et al., "Lineage-specific enhancers activate self-renewal genes in macrophages and embryonic stem cells," Sci., Feb. 12, 2016, pp. 680 and aad5510-1 to aad5510-13, vol. 351, No. 6274.
Steed, A. et al., "The microbial metabolite desaminotyrosine protects from influenza through type I interferon," Sci., Aug. 4, 2017, pp. 498-502, vol. 357.
Stevens, V. et al., "Comparative Effectiveness of Vancomycin and Metronidazole for the Prevention of Recurrence and Death in Patients With Clostridium difficile Infection," JAMA Intern. Med., 2017, pp. 546-553, vol. 177, No. 4.
Sun, L. et al., "Type I Interferons Link Viral Infection to Enhanced Epithelial Turnover and Repair," Cell Host Microbe, Jan. 14, 2015, pp. 85-97, vol. 17.
Takagi, S. et al., "Effectiveness of an 'half elemental diet' as maintenance therapy for Crohn's disease: a randomized-controlled trial," Aliment. Pharmacol. Ther., 2006, pp. 1333-1340, vol. 24.
Trabzuni, D. et al., "Fine-Mapping, Gene Expression and Splicing Analysis of the Disease Associated LRRK2 Locus," PLoS One, Aug. 2013, pp. 1-9, vol. 8, No. 8, e70724.
Trompette, A. et al., "Gut microbiota metabolism of dietary fiber influences allergic airway disease and hematopoiesis," Nat. Med., Feb. 2014, pp. 159-166, vol. 20, No. 2.
Tschurtschenthaler, M. et al., "Type I interferon signalling in the intestinal epithelium affects Paneth cells, microbial ecology and epithelial regeneration," Gut, 2014, pp. 1921-1931, vol. 63.
Uhlig, H. et al., "The Diagnostic Approach to Monogenic Very Early Onset Inflammatory Bowel Disease," Gastroenterol., 2014, pp. 990-1007, vol. 147, e1003.
Vacic, V. et al., "Genome-wide mapping of IBD segments in an Ashkenazi PD cohort identifies associated haplotypes," Hum. Mol. Genet., 2014, pp. 4693-4702, vol. 23, No. 17.
Van Hauwermeiren, F. et al., "TNFR1-induced lethal inflammation is mediated by goblet and Paneth cell dysfunction," Mucosal Immunol., Jul. 2015, pp. 828-840, vol. 8, No. 4.
Van Rooijen, N. et al., "Elimination of phagocytic cells in the spleen after intravenous injection of liposome-encapsulated dichloromethylene diphosphonate," Cell Tissue Res., 1984, pp. 355-358, vol. 238, No. 2.
Van Waveren, C. et al., "Transcriptional co-expression and co-regulation of genes coding for components of the oxidative phosphorylation system," BMC Genomics, 2008, pp. 1-15, vol. 9, No. 18.
Vandussen, K. et al., "Genetic Variant Synthesize to Produce Paneth Cell Phenotypes that Define Subtypes of Crohn's Disease," NIH Public Access Author Manuscript, available in PMC Jan. 1, 2015, pp. 1-19, Published in final form as: Gastroenterology, Jan. 2014, pp. 200-209, vol. 146, No. 1.
Vazquez-Baeza, Y. et al., "EMPeror: a tool for visualizing high-throughput microbial community data," Gigascience, 2013, pp. 1-4, vol. 2, No. 16.
Virgin, H. et al., "Metagenomics and Personalized Medicine," Cell, Sep. 30, 2011, pp. 44-56, vol. 147, Elsevier Inc.
Wang, J. et al., "Bacterial colonization dampens influenza-mediated acute lung injury via induction of M2 alveolar macrophages," Nat. Commun., 2013, pp. 1-10, vol. 4, No. 2106.
Wehkamp, J. et al., "Reduced Paneth cell alpha-defensins in ileal Crohn's disease," PNAS, Dec. 13, 2005, pp. 18129-18134, vol. 102, No. 50.
Welsh, E. et al., "Iterative rank-order normalization of gene expression microarray data," BMC Bioinformatics, 2013, pp. 1-11, vol. 14, No. 153.
Willing, B. et al., "Twin Studies Reveal Specific Imbalances in the Mucosa-associated Microbiota of Patients with Ileal Crohn's Disease," Inflamm. Bowel Dis., May 2009, pp. 653-660, vol. 15, No. 5.

(56) References Cited

OTHER PUBLICATIONS

Wilson, C. et al., "Regulation of Intestinal alpha-Defensin Activation by the Metalloproteinase Matrilysin in Innate Host Defense," Sci., Oct. 1, 1999, pp. 113-117, vol. 286, No. 5437.
Yamazaki, K. et al., "A Genome-Wide Association Study Identifies 2 Susceptibility Loci for Crohn's Disease in a Japanese Population," Gastroenterol., 2013, pp. 781-788, vol. 144.
Yamazaki, K. et al., "Absence of mutation in the NOD2/CARD15 gene among 483 Japanese patients with Crohn's disease," J. Hum. Genet., 2002, pp. 469-472, vol. 47.
Yamazaki, K. et al., "Single nucleotide polymorphisms in TNFSFI5 confer susceptibility to Crohn's disease," Hum. Mol. Genet., 2005, pp. 3499-3506, vol. 14, No. 22.
Yang, S-K. et al., "Genome-wide association study of Crohn's disease in Koreans revealed three new susceptibility loci and common attributes of genetic susceptibility across ethnic populations," Gut, 2014, pp. 80-87, vol. 63.
Yang, S-K. et al., "Immunochip Analysis Identification of 6 Additional Susceptibility Loci for Crohn's Disease in Koreans," NIH Public Access Author Manuscript, Jan. 1, 2016, pp. 1-14, published in final edited form as: Inflamm. Bowel Dis., Jan. 2015, pp. 1-7, vol. 21, No. 1.
Yatsunenko, T. et al., "Human gut microbiome viewed across age and geography," HHS Public Access Author Manuscript, Dec. 14, 2012, pp. 1-16, published in final edited form as: Nat., 2012, pp. 222-227, vol. 486, No. 7402.
Yilmaz, O. et al., "mTORC1 in the Paneth cell niche couples intestinal stem-cell function to calorie intake," Nat., 2012, pp. 490-495, vol. 486.
Zhang, Q. et al., "Commensal bacteria direct selective cargo sorting to promote symbiosis," Nat. Immunol., Sep. 2015, pp. 918-926, vol. 16, No. 9.
Abt, M. et al., "Commensal Bacteria Calibrate the Activation Threshold of Innate Antiviral Immunity," Immunity, Jul. 27, 2012, pp. 158-170, vol. 37.
Adolph, T. et al., "Paneth cells as a site of origin for intestinal inflammation," HHS Public Access Author Manuscript, May 14, 2014, pp. 1-19, published in final edited form as: Nature, Nov. 14, 2013, pp. 272-276, vol. 503, No. 7475.
Albenberg, L. et al., "Diet and the Intestinal Microbiome: Associations, Functions, and Implications for Health and Disease," NIH Public Access Author Manuscript, May 1, 2015, pp. 1-16, published in final edited form as: Gastroenterol., May 2014, pp. 1564-1572, vol. 146, No. 6.
Arijs, I. et al., "Mucosal gene signatures to predict response to infliximab in patients with ulcerative colitis," Gut, Aug. 20, 2009, pp. 1612-1619, vol. 58, No. 12, BMJ Publishing Group Ltd.
Arimori, Y. et al., "Type I interferon limits influenza virus-induced acute lung injury by regulation of excessive inflammation in mice," Antiviral Res., 2013, pp. 230-237, vol. 99, No. 3.
Avitzur, Y. et al., "Mutations in Tetratricopeptide Repeat Domain 7A Result in a Severe Form of Very Early Onset Inflammatory Bowel Disease," Gastroenterol., Apr. 2014, pp. 1028-1039, vol. 146, No. 4.
Aziz, A. et al., "MafB/c-Maf Deficiency Enables Self-Renewal of Differentiated Functional Macrophages," Sci., Nov. 6, 2009, pp. 867-871, vol. 326, No. 5954.
Baxt, L. et al., "Role of Autophagy in the Maintenance of Intestinal Homeostasis," HHS Public Access Author Manuscript, Sep. 1, 2016, pp. 1-19, published in final edited form as: Gastroenterol., Sep. 2015, pp. 553-562, vol. 149, No. 3.
Belkaid, Y. et al., "Role of the Microbiota in Immunity and Inflammation," Cell, Mar. 27, 2014, pp. 121-141, vol. 157, Elsevier Inc.
Bernstein, C. et al., "World Gastroenterology Organization Practice Guidelines for the Diagnosis and Management of IBD in 2010," Inflamm. Bowel Dis., Jan. 2010, pp. 112-124, vol. 16, No. 1, Wiley InterScience.
Bevins, C. et al., "Paneth cells, antimicrobial peptides and maintenance of intestinal homeostasis," Nat. Rev. Microbiol., May 2011, pp. 356-368, No. 9.
Billiau, A., "Anti-inflammatory properties of Type I inteiferons," Antiviral Res., 2006, pp. 108-116, vol. 71.
Bloom, S. et al., "Commensal Bacteroides Species Induce Colitis in Host-Genotype-Specific Fashion in a Mouse Model of Inflammatory Bowel Disease," Cell Host Microbe, May 19, 2011, pp. 390-403, vol. 9, Elsevier Inc.
Boon, A. et al., "Host Genetic Variation Affects Resistance to Infection with a Highly Pathogenic H5N1 Influenza A Virus in Mice," J. Virol., Oct. 2009, pp. 10417-10426, vol. 83, No. 20.
Byrne, A. et al., "Pulmonary macrophages: key players in the innate defence of the airways," Thorax, 2015, pp. 1189-1196, vol. 70.
Cadwell, K. et al., "A key role for autophagy and the autophagy gene Atg16l1 in mouse and human intestinal Paneth cells," Nat., Nov. 13, 2008, pp. 259-263, vol. 456, Macmillan Publishers Limited.
Cadwell, K. et al., "Virus-Plus-Susceptibility Gene Interaction Determines Crohn's Disease Gene Atg16L1 Phenotypes in Intestine," Cell, Jun. 25, 2010, pp. 1135-1145, vol. 141, Elsevier Inc.
Caporaso, J. et al., "QIIME allows analysis of high-throughput community sequencing data," NIH Public Access Author Manuscript, Aug. 16, 2011, pp. 1-4, published in final edited form as: Nat. Methods, May 2010, pp. 335-336, vol. 7, No. 5.
Caporaso, J. et al., "Ultra-high-throughput microbial community analysis on the Illumina HiSeq and MiSeq platforms," ISME J., 2012, pp. 1621-1624, vol. 6.
Carr, I. et al., "The effects of migration on ulcerative colitis: a three-year prospective study among Europeans and first- and second-generation South Asians in Leicester (1991-1994)," Am. J. Gastroenterol., Oct. 1999, pp. 2918-2922, vol. 94, No. 10.
Chassaing, B. et al., "The Commensal Microbiota and Enteropathogens in the Pathogenesis of Inflammatory Bowel Diseases," Gastroenterol., 2011, pp. 1720-1728, vol. 140, AGA Institute.
Chen, P. et al., "Autophagy-mediated regulation of macrophages and its applications for cancer," Autophagy, Feb. 2014, pp. 192-200, vol. 10, No. 2, Landes Bioscience.
Chuang, L-S. et al., "A Frameshift in CSF2RB Predominant Among Ashkenazi Jews Increases Risk for Crohn's Disease and Reduces Monocyte Signaling via GM-CSF," Gastroenterol., Oct. 2016, pp. 710-723, vol. 151, No. 4.
Conte, M. et al., "Gut-associated bacterial microbiota in paediatric patients with inflammatory bowel disease," Gut, 2006, pp. 1760-1767, vol. 55.
Dalal, S. et al., "The microbial basis of inflammatory bowel diseases," J. Clin. Invest., Oct. 2014, pp. 4190-4196, vol. 124, No. 10.
Davidson, S. et al., "Pathogenic potential of interferon alphabeta in acute influenza infection," Nat. Commun., 2014, pp. 1-15, vol. 5, No. 3864.
Deuring, J. et al., "Genomic ATG16L1 risk allele-restricted Paneth cell ER stress in quiescent Crohn's disease," Gut, 2013, pp. 1081-1091, vol. 63.
Dinh, D. et al., "Intestinal Microbiota, Microbial Translocation, and Systemic Inflammation in Chronic HIV Infection," J. Infect. Dis., Jan. 2015, pp. 19-27, vol. 211.
Donohoe, D. et al., "The Microbiome and Butyrate Regulate Energy Metabolism and Autophagy in the Mammalian Colon," Cell Metab., May 4, 2011, pp. 517-526, vol. 13, Elsevier Inc.
Faith, D. et al., "Phylogenetic diversity (PD) and biodiversity conservation: some bioinformatics challenges," Evol. Bioinform. Online, 2006, pp. 121-128, vol. 2.
Fava, V. et al., "A Missense LRRK2 Variant Is a Risk Factor for Excessive Inflammatory Responses in Leprosy," PLoS Negl. Trop. Dis., Feb. 2016, pp. 1-14, vol. 10, No. 2, e0004412.
Franke, A. et al., "Genome-wide meta-analysis increases to 71 the number of confirmed Crohn's disease susceptibility loci," Nat. Genet., Dec. 2010, pp. 1118-1125, vol. 42, No. 12.
Fuyuno, Y. et al., "Genetic characteristics of inflammatory bowel disease in a Japanese population," J. Gastroenterol., Jul. 2016, pp. 672-681, vol. 51, No. 7.

(56) References Cited

OTHER PUBLICATIONS

Gevers, D. et al., "The Treatment-Naive Microbiome in New-Onset Crohn's Disease," Cell Host Microbe, Mar. 12, 2014, pp. 382-392, vol. 15, Elsevier Inc.

Gonzalez-Navajas, J. et al., "Immunomodulatory functions of type I interferons," Nat. Rev. Immunol., Feb. 2012, pp. 125-135, vol. 12.

Guarda, G. et al., "Type I Interferon Inhibits Interleukin-1 Production and Inflammasome Activation," Immunity, Feb. 25, 2011, pp. 213-223, vol. 34.

Gunther, C. et al., "Caspase-8 regulates TNF-alpha-induced epithelial necroptosis and terminal ileitis," Nat., Sep. 15, 2011, pp. 335-339, vol. 477, Macmillan Publishers Limited.

Haberman, Y. et al., "Pediatric Crohn disease patients exhibit specific ileal transcriptome and microbiome signature," J. Clin. Invest, 2014, pp. 3617-3633, vol. 124, No. 8.

Hampe, J. et al., "A genome-wide association scan of nonsynonymous SNPs identifies a susceptibility variant for Crohn disease in ATG16L1," Nat. Genet, Feb. 2007, pp. 207-211, vol. 39, No. 2.

Hansen, R. et al., "Microbiota of De-Novo Pediatric IBD: Increased Faecalibacterium Prausnitzii and Reduced Bacterial Diversity in Crohn's But Not in Ulcerative Colitis," Am. J. Gastroenterol., Dec. 2012, pp. 1913-1922, vol. 107.

Hirano, A. et al., "Association Study of 71 European Crohn's Disease Susceptibility Loci in a Japanese Population," Inflamm. Bowel Dis., Mar. 1, 2013, pp. 526-533, vol. 19, No. 3.

Hodin, C. et al., "Reduced Paneth cell antimicrobial protein levels correlate with activation of the unfolded protein response in the gut of obese individuals," J. Pathol., Oct. 2011, pp. 276-284, vol. 225, No. 2.

Hogner, K. et al., "Macrophage-expressed IFN-beta Contributes to Apoptotic Alveolar Epithelial Cell Injury in Severe Influenza Virus Pneumonia," PLoS Pathog., Feb. 2013, pp. 1-16, vol. 9, No. 2, e1003188.

Honda, K. et al., "IRF-7 is the master regulator of type-I interferon-dependent immune responses," Nature, Apr. 2005, pp. 772-777, vol. 434.

Hong, S. et al., "Deep resequencing of 131 Crohn's disease associated genes in pooled DNA confirmed three reported variants and identified eight novel variants," Gut, 2016, pp. 788-796, vol. 65.

Huttenhower, C. et al., "Inflammatory Bowel Disease as a Model for Translating the Microbiome," Immunity, Jun. 19, 2014, pp. 843-854, vol. 40, Elsevier Inc.

Ichinohe, T. et al., "Microbiota regulates immune defense against respiratory tract influenza A virus infection," PNAS, Mar. 29, 2011, pp. 5354-5359, vol. 108, No. 13.

Igarashi, M. et al., "mTORC1 and SIRT1 Cooperate to Foster Expansion of Gut Adult Stem Cells during Calorie Restriction," Cell, Jul. 2016, pp. 436-450, vol. 166.

Inoue, N. et al., "Lack of Common NOD2 Variants in Japanese Patients With Crohn's Disease," Gastroenterol., Jul. 2002, pp. 86-91, vol. 123, No. 1.

International Search Report and Written Opinion dated Dec. 3, 2018 from related Patent Application No. PCT/US2018/042761; 18 pgs.

Zhang, Z. et al., "Isolation and Identification of Quercetin Degrading Bacteria from Human Fecal Microbes," PLoS One, Mar. 2014, pp. 1-5, vol. 9, No. 3, e90531.

Zhou, Y. et al., "TSC2/mTORC1 signaling controls Paneth and goblet cell differentiation in the intestinal epithelium," Cell Death Dis., 2015, pp. 1-10, vol. 6, No. e1631, Macmillan Publishers Limited.

* cited by examiner

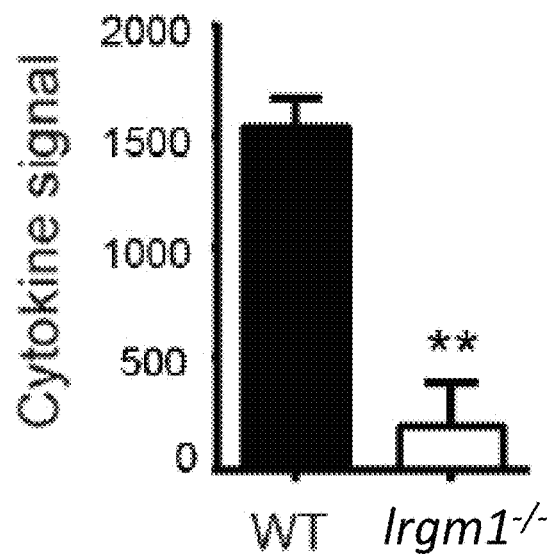
FIG. 2H
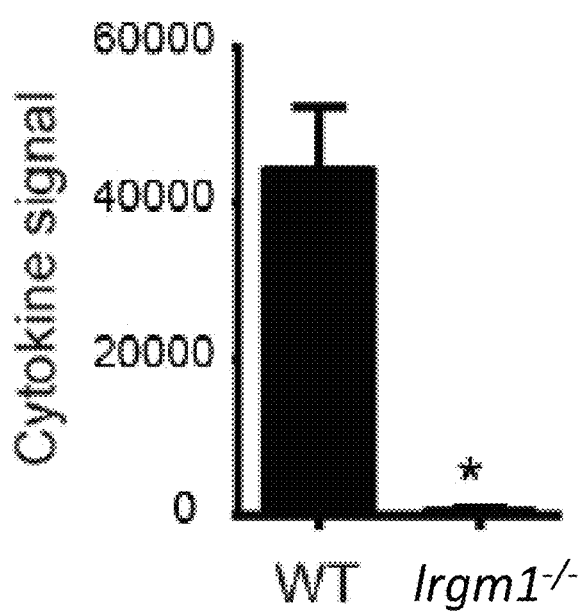 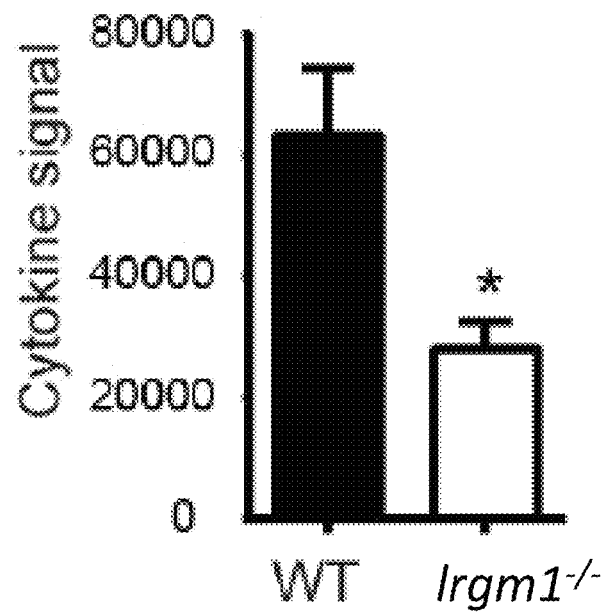
FIG. 2I  FIG. 2J

▲ Control
△ Desaminotyrosine
✱ Desaminotyrosine pretreatment
✗ Desaminotyrosine rescue

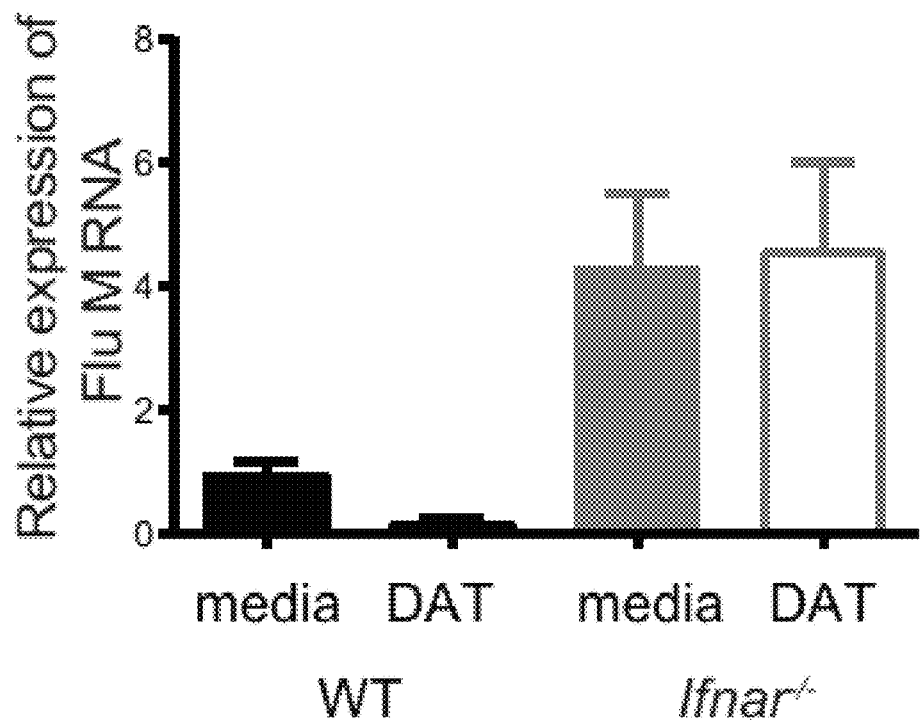
FIG. 4K
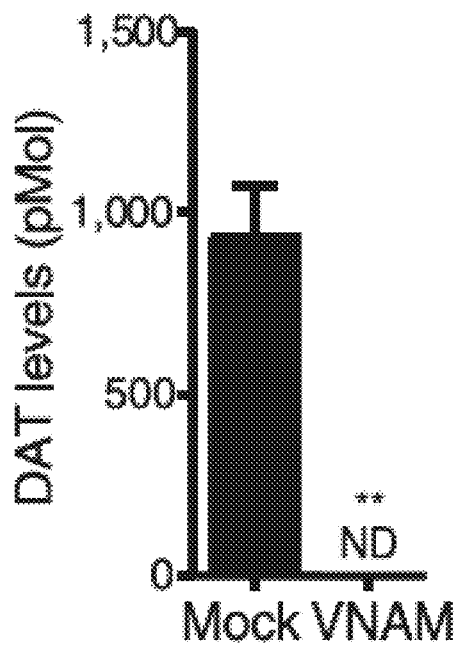 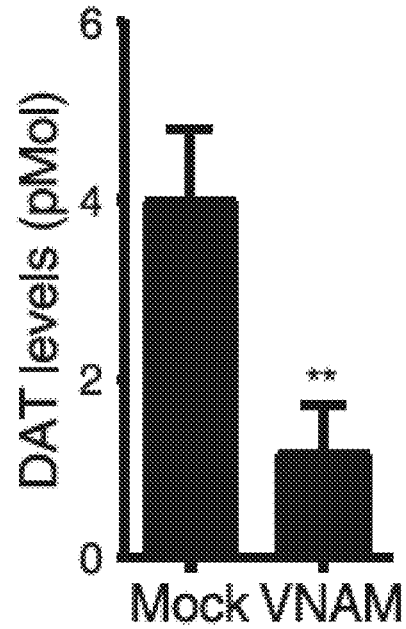
FIG. 4L        FIG. 4M

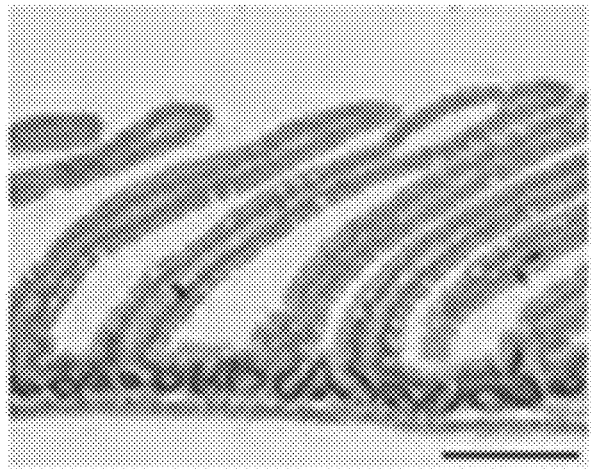 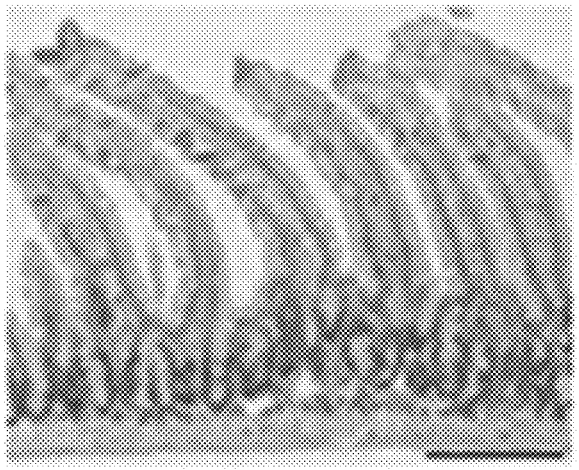
FIG. 13B  FIG. 13C
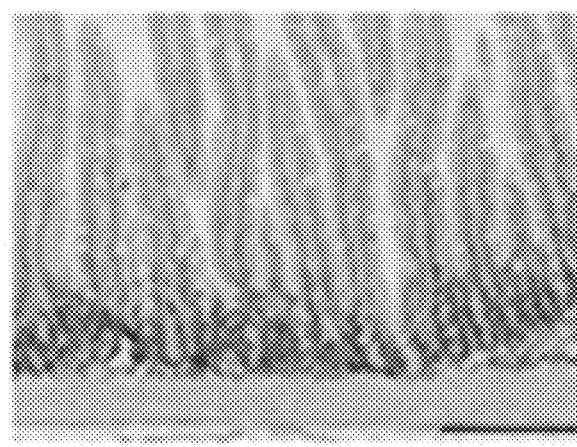 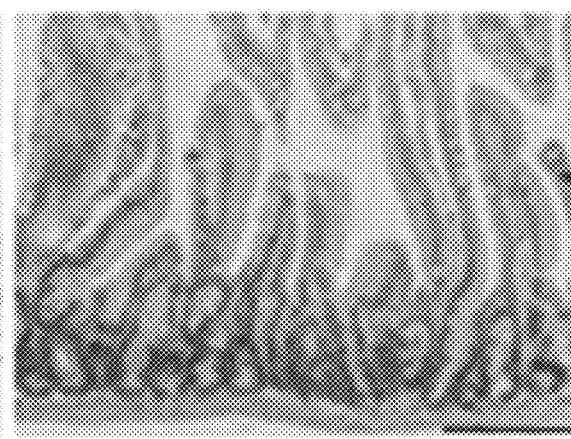
FIG. 13D  FIG. 13E

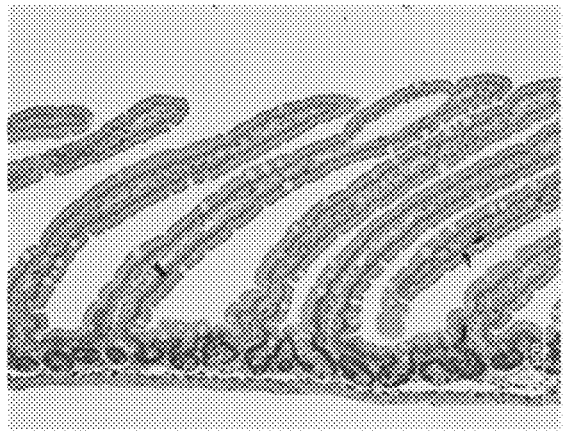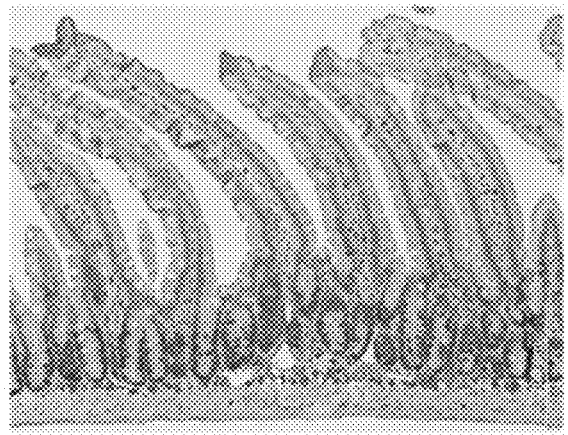
FIG. 14A  FIG. 14B
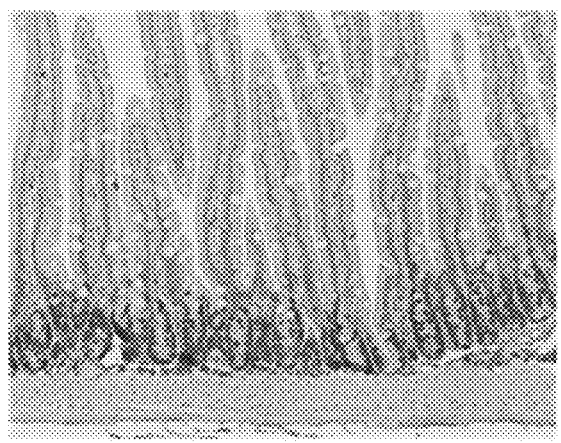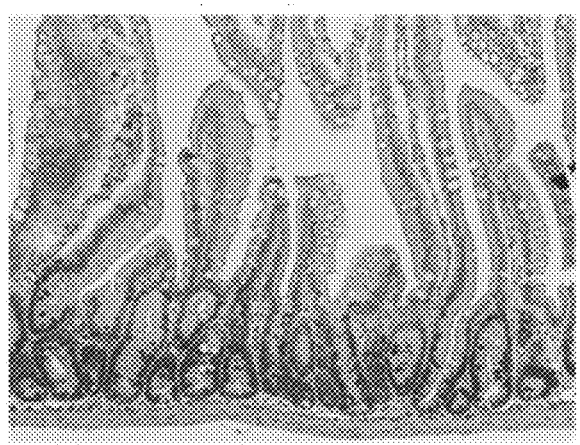
FIG. 14C  FIG. 14D

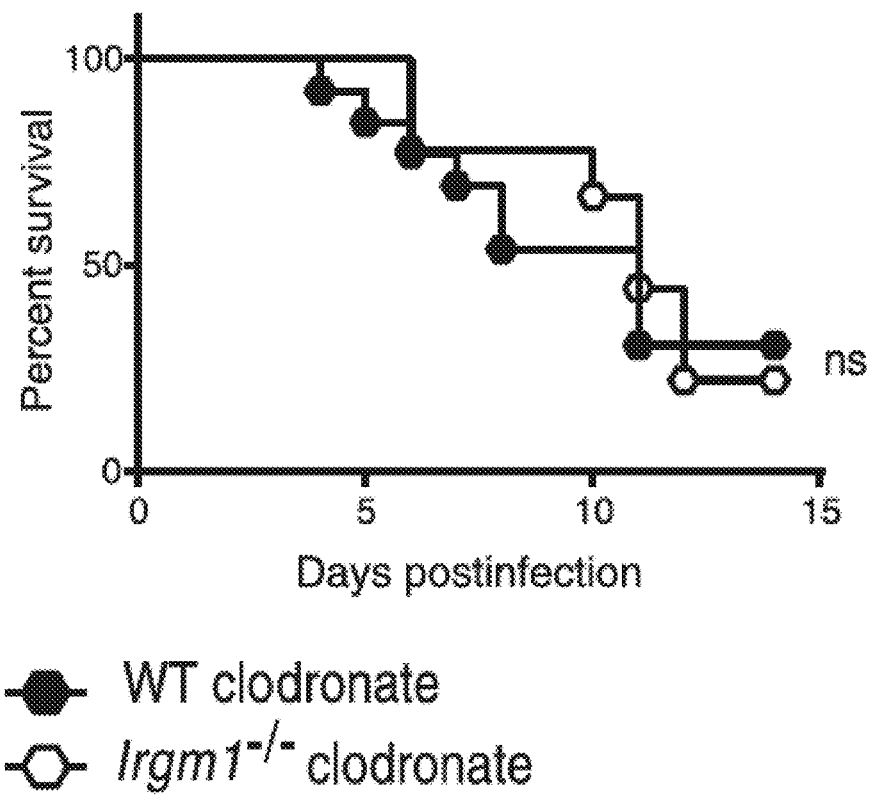
FIG. 20C
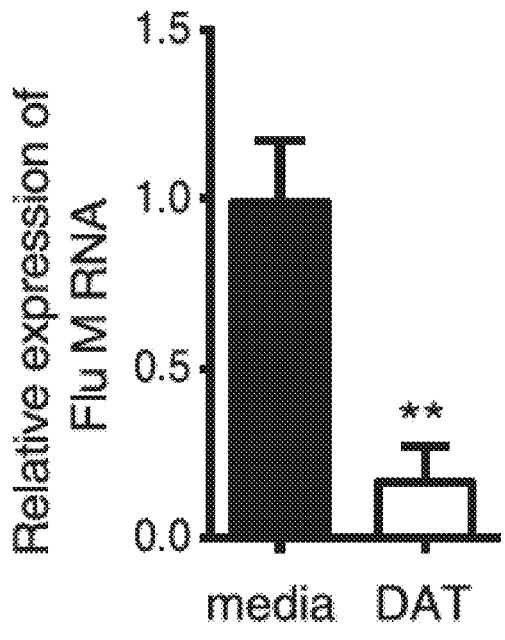 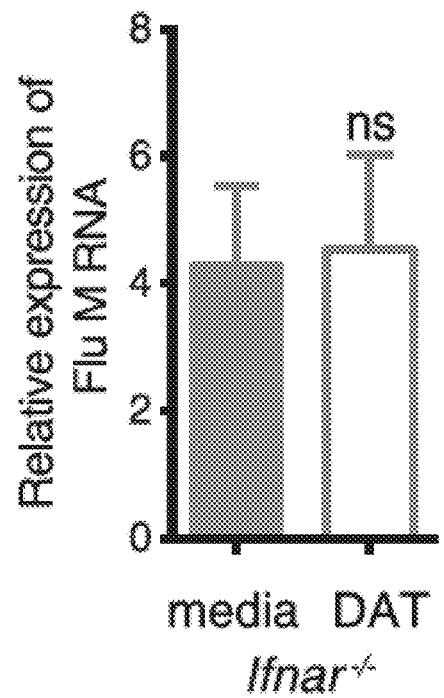
FIG. 20D  FIG. 20E

COMPOSITIONS COMPRISING DESAMINOTYROSINE AND USES THEREOF TO ENHANCE TYPE I INTERFERON STIMULATION

CROSS REFERENCE TO RELATED APPLICATIONS

This application claims the benefit of International Patent Application number PCT/US2017/058478, filed Oct. 26, 2017, which claims the benefit of U.S. Provisional Application No. 62/413,241, filed Oct. 26, 2016, the disclosures of which are hereby incorporated by reference in their entirety.

FIELD OF THE INVENTION

The disclosure provides compositions comprising desaminotyrosine and methods of use thereof in enhancing type I interferon stimulation, epithelial proliferation, and treatment of inflammatory bowel disease.

BACKGROUND OF THE INVENTION

Influenza, commonly known as "the flu," is an infectious disease caused by an influenza virus. Symptoms can be mild to severe. The most common symptoms include: a high fever, runny nose, sore throat, muscle pains, headache, coughing, and fatigue. Influenza spreads around the world in a yearly outbreak, resulting in about three to five million cases of severe illness and about 250,000 to 500,000 deaths. In the Northern and Southern parts of the world outbreaks occur mainly in winter while in areas around the equator outbreaks may occur at any time of the year. Death occurs mostly in the young, the old and those with other health problems. Accordingly, there is a need to prevent the severity of flu symptoms.

Additionally, inflammatory bowel disease (IBD) is a group of inflammatory conditions of the colon and small intestine. Crohn's disease and ulcerative colitis are the principal types of inflammatory bowel disease. It is important to note that not only does Crohn's disease affect the small intestine and large intestine, it can also affect the mouth, esophagus, stomach and the anus whereas ulcerative colitis primarily affects the colon and the rectum. IBD is a complex disease which arises as a result of the interaction of environmental and genetic factors leading to immunological responses and inflammation in the intestine. IBD resulted in a global total of 51,000 deaths in 2013 and 55,000 deaths in 1990. Accordingly, there is a need in the art for ways to treat IBD, including repair the damage to the intestines that results from IBD. Methods to restore the intestinal epithelium may also be broadly applied to other diseases that result from epithelial damage and dysfunction.

SUMMARY OF THE INVENTION

One aspect of the present disclosure is directed to a method to enhance type I interferon stimulation in a subject. The method comprises administering to the subject a composition comprising desaminotyrosine or a desaminotyrosine derivative.

Another aspect of the present disclosure is directed to a method to prevent or reduce influenza-associated symptoms in a subject. The method comprises administering to the subject a composition comprising desaminotyrosine or a desaminotyrosine derivative.

An additional aspect of the present disclosure is directed to a method to promote epithelial tissue proliferation in a subject. The method comprises administering to the subject a composition comprising desaminotyrosine or a desaminotyrosine derivative.

A further aspect of the present disclosure is directed to a method to promote wound repair in a subject. The method comprises administering to the subject a composition comprising desaminotyrosine or a desaminotyrosine derivative.

An additional aspect of the present disclosure is directed to a method to treat colitis in a subject. The method comprises administering to the subject a composition comprising desaminotyrosine or a desaminotyrosine derivative.

Other aspects and iterations of the disclosure are described in more detail below.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) IFN activity as measured by an antiviral bioassay in the lungs of littermate control and $Irgm1^{-/-}$ mice. n=19-21 mice per group from 5 independent experiments. (FIG. 1B and FIG. 1C) Relative expression of Oas2 (FIG. 1B) and Mx2 (FIG. 1D) mRNA in the lungs from littermate control and $Irgm1^{-/-}$ mice. n=7-10 mice per group from 3 independent experiments for Oas2 and n=12-14 mice per group from 4 independent experiments for Mx2. (FIG. 1D) Percent weight loss from baseline of littermate control, $Irgm1^{-/-}$, and $Irgm1^{-/-}$; $Ifnar^{-/-}$ mice infected with 5,000 pfu of Influenza H1N1. n=34, 26, and 12 mice per group for littermate control, $Irgm1^{-/-}$, and $Irgm1^{-/-}$; $Ifnar^{-/-}$ mice respectively from 5 independent experiments for littermate control and $Irgm1^{-/-}$ mice and 2 independent experiments for $Irgm1^{-/-}$;$Ifnar^{-/-}$ mice. Asterisk on top represents significance between littermate control and $Irgm1^{-/-}$ mice, and asterisk on bottom represents significance between $Irgm1^{-/-}$ and $Irgm1^{-/-}$;$Ifnar^{-/-}$ mice. (FIG. 1E) Kaplan-Meier survival curve of littermate control, $Irgm1^{-/-}$, and $Irgm1^{-/-}$; $Ifnar^{-/-}$ mice infected with 5,000 pfu of Influenza H1N1. n=40 mice per group for littermate control and $Irgm1^{-/-}$ mice and 25 for $Irgm1^{-/-}$;$Ifnar^{-/-}$ mice from 5 independent experiments for littermate control and Irgm1−/− mice and 2 independent experiments for $Irgm1^{-/-}$;$Ifnar^{-/-}$ mice. (FIG. 1F) Infectious viral load by plaque assay at indicated timepoints postinfection for littermate control and $Irgm1^{-/-}$ mice infected with 5,000 pfu of Influenza H1N1. n=11-23 mice per group from 4-5 independent experiments for days 3 and 6 and n=4-7 mice from 2 independent experiments for day 10. *p< or =0.05 by Mann-Whitney test, p<0.01 by Mann-Whitney test, *p<0.001 by Mantel-Cox test (FIG. 1C) or Mann-Whitney test, and ****p<0.0001 by Mann-Whitney test. (FIG. 1G and FIG. 1H) Representative images of influenza H1N1 staining by polyclonal antibody on lung cross sections from wild-type (WT) (FIG. 1G) and $Irgm1^{-/-}$ (FIG. 1H) mice 6 days postinfection (representative images from 5-6 mice per group from two experiments). Bar=200 µm.

FIG. 2A, FIG. 2B, FIG. 2C, FIG. 2D, FIG. 2E, FIG. 2F, FIG. 2G, FIG. 2H, FIG. 2I, FIG. 2J, FIG. 2K, FIG. 2L, FIG. 2M, FIG. 2N, FIG. 2O, FIG. 2P, FIG. 2Q, FIG. 2R, FIG. 2S, FIG. 2T, FIG. 2U, FIG. 2V, and FIG. 2W depict graphs and images showing that Irgm1$^{-/-}$ lungs have decreased inflammatory chemokines and cytokines associated with severe human influenza. (FIG. 2A and FIG. 2B) Representative images of uninfected lung cross sections from littermate control (FIG. 2A) and Irgm1$^{-/-}$ mice (FIG. 2B). (FIG. 2C) Percentage of mice with presence of lymphoid tissue aggregates for littermate control, Irgm1$^{-/-}$, Ifnar$^{-/-}$ and Irgm1$^{-/-}$; Ifnar$^{-/-}$. n=4-5 animals per group. (FIG. 2D) Average ratio of lymphoid tissue aggregate to lung parenchyma area was measured in littermate control, Irgm1$^{-/-}$, Ifnar$^{-/-}$ and Irgm1$^{-/-}$;Ifnar$^{-/-}$. n=4-5 animals per group. (FIG. 2E) Kaplan-Meier survival curve of Irgm1$^{-/-}$ and Irgm1$^{-/-}$; Rag$^{-/-}$ mice infected with 1,000 pfu of Influenza H1N1. n=15-22 mice per group from 3 independent experiments. (FIG. 2F, FIG. 2G, FIG. 2H, FIG. 2I, and FIG. 2J) TNFα, (FIG. 2F) MIP-1 (FIG. 2G), IL-10 (FIG. 2H), MCP-1 (FIG. 2I), and IL-1Rα (FIG. 2J) levels in lung homogenates from littermate control and Irgm1$^{-/-}$ mice 6 days postinfection with 5,000 pfu of Influenza H1N1. n=3 mice in each group. (FIG. 2K and FIG. 2L) Representative images of lung cross sections from infected littermate control and Irgm1$^{-/-}$ mice 6 days postinfection. Black box represents location magnified below. (FIG. 2L) Cleaved caspase 3 immunohistological staining of infected littermate control and Irgm1$^{-/-}$ lung cross sections 6 days postinfection. Black box represents location magnified below. (FIG. 2M) Percentage of airways positive for at least 1 cleaved caspase positive cell per airway. n=5-6 mice per group from 2 independent experiments for F-H.*p<0.05 and p<0.01 by Mann-Whitney test. (FIG. 2N, FIG. 2O, FIG. 2P, FIG. 2Q, FIG. 2R, FIG. 2S, FIG. 2T, and FIG. 2U) Viral RNA transcript counts, PV1 (FIG. 2N), PA (FIG. 2O), HA (FIG. 2P), NP (FIG. 2Q), NA (FIG. 2R), NS1 (FIG. 2S), MP2 (FIG. 2T), and MP1 (FIG. 2U) in the lungs of infected control and Irgm1$^{-/-}$ mice at day 3 postinfection. (FIG. 2V and FIG. 2W) Bioassay for type I IFN in the serum of indicated mice. Specificity for type I IFN is shown by the addition of anti-Ifnar antibody (n=2-3 mice per group). *p<0.001 and ns=not significant by Mann-Whitney test. Kaplan-Meier survival analysis of infected Irgm1$^{-/-}$ and Irgm1$^{-/-}$;Rag$^{-/-}$ mice (n=15-22 mice per group from three experiments). *p<0.05 by Mantel-Cox test.

(FIG. 3A) Kaplan-Meier survival curve of littermate control and Irgm1$^{-/-}$ mice treated with control liposomes or clodronate liposomes 2 days prior to infection, infected with 5,000 pfu of Influenza H1N1 and treated with control liposomes or clodronate liposomes again on days 0, 2, 5, 8, and 11 postinfection. n=6-13 mice per group from 3 independent experiments. (FIG. 3B) IFN activity as measured by an antiviral bioassay in the serum of littermate control and Irgm1$^{-/-}$ mice treated with control liposomes or clodronate liposomes twice separated by 48 hours. n=7-8 mice per group from 2 independent experiments. (FIG. 3C) IFNα protein quantification from bone marrow derived macrophages infected with Influenza H1N1 at MOI-2 for 48 hours. n=3 independent experiments. (FIG. 3D) Relative expression of matrix influenza mRNA from bone marrow derived macrophages infected with Influenza H1N1 at MOI-2 for 48 hours. n=7 independent experiments for littermate control and Irgm1$^{-/-}$ and 2 independent experiments comparing Irgm1$^{-/-}$ and Irgm1$^{-/-}$;Ifnar$^{-/-}$ cells. *p<0.05 by Mann-Whitney and **p= or <0.01 by Mantel-Cox test (FIG. 3A) or Mann-Whitney test.

FIG. 4A, FIG. 4B, FIG. 4C, FIG. 4D, FIG. 4E, FIG. 4F, FIG. 4G, FIG. 4H, FIG. 4I, FIG. 4J, FIG. 4K, FIG. 4L, FIG. 4M, FIG. 4N, FIG. 4O, and FIG. 4P depicts graphs and images showing that microbial-derived metabolite induces IFN and protects from Influenza. (FIG. 4A) Assay schematic of the screen for IFN-inducing metabolites. (FIG. 4B) Kaplan-Meier survival analysis of groups of mice with variations on the timing desaminotyrosine treatment with respect to infection. Control=no desaminotyrosine; desaminotyrosine continuous=one week pretreatment and continuous treatment postinfection; desaminotyrosine pretreatment=one week pretreatment only; desaminotyrosine day +2=treatment commenced 2 days postinfection (n=30 mice/group from two experiments). (FIG. 4C) Fold increase in luminescence for desaminotyrosine at indicated doses with polyIC and Type I IFN. n=3-4 independent experiments. (FIG. 4D) Relative expression of matrix influenza mRNA from wildtype and Ifnar$^{-/-}$ BMDMs pretreated with or without desaminotyrosine and then infected (n=7 replicates/group from two experiments for wildtype BMDMs and 3 replicates/group from three experiments for Ifnar$^{-/-}$ BMDMs). Matrix viral RNA expression determined by qRT-PCR from infected BMDMs from indicated genotypes (n=two to seven experiments). (FIG. 4E and FIG. 4F) Percent weight loss from baseline of mice treated with or without antibiotics and with or without desaminotyrosine and infected with 5,000 pfu of Influenza H1N1. n=30 mice per group from 2 independent experiments. * p<0.05 and ** p<0.01 by ANOVA with Tukey's multiple comparisons. (FIG. 4G) Kaplan-Meier survival curve of mice in E. (FIG. 4H) Percent weight loss from baseline of Ifnar$^{-/-}$ mice treated with or without desaminotyrosine and infected with 5,000 pfu of Influenza H1N1. n=11-12 mice per group from 1-2 independent experiments. (FIG. 4I) Kaplan-Meier survival curve of Ifnar$^{-/-}$ mice in G. (FIG. 4J) Kaplan-Meier survival curve of mice pretreated with desaminotyrosine for only 1 week and then infected with Influenza H1N1, treated for 1 week prior to infection and then treatment continued, not treated, or treated for rescue 2 days postinfection. n=15 mice per group in the pretreated or rescue group. (FIG. 4K) Relative expression of matrix influenza mRNA from littermate control and Ifnar$^{-/-}$ bone marrow derived macrophages treated with or without desaminotyrosine for 24 hours and then infected with Influenza H1N1 at MOI-2 for 48 hours. n=2 and 3 independent experiments respectively for littermate control including 7 independent BMDM lines and Ifnar$^{-/-}$ cells including 3 independent BMDM lines. (FIG. 4L and FIG. 4M) Stool (FIG. 4L) and serum (FIG. 4M) desaminotyrosine levels measured by mass spectroscopy in mice either vehicle (mock) or treated with 2 weeks of antibiotics (n=9-15 mice/group from three experiments). (FIG. 4N, FIG. 4O, and FIG. 4P) Relative mRNA expression of ISGs, Mx2 (FIG. 4N), Oas2 (FIG. 4O), and IP-10 (FIG. 4P), from lung homogenates of mice treated with or without desaminotyrosine (n=5 samples/group from two experiments). Graphs denote average with SEM displayed. ND denotes not detected. *p<0.05, **p<0.01. ANOVA used for statistical analysis in E (F=10.9) with Sidak's multiple comparisons test.

(FIG. 7A) CD45—green highlighting leukocytes. (FIG. 7B) B220—green and CD19—pink highlighting B-cells. (FIG. 7C) CD3—purple and B220—green highlighting T-cells and B-cells, respectively.

(FIG. 11A, FIG. 11B, and FIG. 11C) IFN 50 U/ml; (FIG. 11D, FIG. 11E, and FIG. 11F) IFN 5 U/ml; (FIG. 11G, FIG. 11H, and FIG. 11I) PolyIC 20 ug/ml; and (FIG. 11J, FIG. 11K, and FIG. 11L) PolyIC 2.5 ug/ml.

FIG. 14A, FIG. 14B, FIG. 14C, FIG. 14D, and FIG. 14E depict images and a graph showing that desaminotyrosine treatment increased crypt height and epithelial proliferation. (FIG. 14A, FIG. 14B, FIG. 14C, and FIG. 14D) Representative images of the crypt height for control (FIG. 14A), polyIC (FIG. 14B), deasminotyrosine, (FIG. 14C), and desaminotyrosine+polyIC (FIG. 14D) treated mice. FIG. 14E depicts a graph quantifying the crypt height after the various treatments relative to the control treated mice.

FIG. 16A depicts an image showing that DSS treatment damages ~90% of the distal colon. FIG. 16B depicts an image showing that desaminotyrosine treatment results in only minimal areas of damage in the distal colon. Specifically, ~8% of the distal colon is damaged.

(FIG. 18A and FIG. 18B) Kaplan-Meier survival analysis of groups of mice treated without antibiotics (FIG. 18A) or with a cocktail of broad spectrum antibiotics (FIG. 18B, VNAM) and then treated with or without desaminotyrosine prior to infection (n=30 mice/group from two experiments, inclusive of all groups but plotted separately for clarity). (FIG. 18C) Kaplan-Meier survival analysis of Ifnar$^{-/-}$ mice treated with or without DAT and infected with influenza (n=18-21 mice/group from two experiments). (FIG. 18E) Infectious viral load determined by plaque assay at day 5 postinfection for groups of mice from FIG. 18A and FIG. 18B (n=10 mice/group from two experiments). (FIG. 18F) Matrix viral RNA expression determined by qRT-PCR from lung homogenates of mice treated with or without desaminotyrosine as in C. (FIG. 18G, FIG. 18H, FIG. 18J, and FIG. 18K) Representative images of lung cross sections from mice treated with (FIG. 18H and FIG. 18K) or without desaminotyrosine (FIG. 18G and FIG. 18J) at 5 days postinfection. Boxed areas are magnified immediately below. (FIG. 18G and FIG. 18H) H+E stained sections. Bar=50 μm. (FIG. 18J and FIG. 18K) Sections stained for cleaved caspase 3 by immunohistochemistry. Bar=20 μm. (FIG. 18L) Percentage of airways positive for at least one cleaved caspase positive cell within an airway cross section (n=10 mice/group from two experiments for FIG. 18G, FIG. 18H, FIG. 18I, FIG. 18JK, and FIG. 18L). (FIG. 18D) Time course of quercetin degradation after incubation with control, mouse cecal contents, or single bacterial species (n=6 replicates/group from two experiments). (FIG. 18I) Kaplan-Meier survival analysis of VNAM pretreated mice gavaged twice with PBS, cecal contents, or single bacterial species and then infected with influenza (n=20 mice/group from two experiments for PBS, cecal contents, C. orbiscindens gavage or 10 mice/group for C. leptum or E. fecalis gavage). (FIG. 18M) Stool DAT levels measured by mass spectroscopy at time of infection in mice from FIG. 18I (n=10/group). Statistical significance per group is compared to PBS gavaged group. Graphs denote average with SEM displayed. *p<0.05, p<0.01, *p<0.001, ****p<0.0001 and ns denotes not statistically significant. Mantel-Cox test with or without Bonferroni-corrected threshold used in FIG. 18A, FIG. 18B, FIG. 18C, and FIG. 18I. Mann-Whitney test used in FIG. 18E, FIG. 18F and FIG. 18L. ANOVA used in FIG. 18D (F=50.8) and FIG. 18M (F=14.5) with Dunnett's multiple comparisons test.

(FIG. 19C and FIG. 19D) Stool (FIG. 19C) and serum (FIG. 19D) desaminotyrosine levels measured by mass spectroscopy in wild-type mice mock or treated with two weeks of antibiotics and then treated with 200 mM desaminotyrosine in drinking water for one week (n=5-13 per group from two experiments). (FIG. 19E, FIG. 19F, FIG. 19G, and FIG. 19H) Kaplan-Meier survival analysis of nonantibiotic and antibiotic-treated wild-type mice given control or desaminotyrosine in drinking water and then infected with H1N1 influenza strains PR8 (FIG. 19E and FIG. 19F) or Cali/09 (FIG. 19G and FIG. 19H) (n=10 mice per group). *p<0.05 by Mantel-Cox test. (FIG. 19I) Kaplan-Meier survival analysis of wild-type mice treated with indicated antibiotic(s) and then infected with influenza (n=20 mice per group from two experiments). *p<0.05, p<0.01, and p<0.0001 compared to mock treated infected mice by Mantel-Cox test with Bonferroni-corrected threshold. (FIG. 19J, FIG. 19K, FIG. 19L, FIG. 19M, and FIG. 19N) Fecal pellet weight (FIG. 19J), DNA content (FIG. 19K), and relative bacterial DNA by qRT-PCR for wild-type mice gavaged in FIG. 18I (n=20 samples per group for after VNAM treatment group and PBS, C. orbiscindens (FIG. 19L) and cecal gavaged groups from two experiments and n=10 samples per group for before VNAM treatment group and C. leptum (FIG. 19M) and E. fecalis gavaged groups (FIG. 19N)). **p<0.01 by Mann-Whitney test.

FIG. 20A, FIG. 20B, FIG. 20C, FIG. 20D, FIG. 20E, FIG. 20F, FIG. 20G, FIG. 20H, FIG. 20I, FIG. 20J, FIG. 20K, FIG. 20L, FIG. 20M, and FIG. 20N depict graphs showing that DAT enhances types I IFN in macrophages via type I IFN amplification. (FIG. 20A) Kaplan-Meier survival analysis of groups of mice with variations on the timing desaminotyrosine treatment with respect to infection. Control=no desaminotyrosine; desaminotyrosine continuous=one week pretreatment and continuous treatment postinfection; desaminotyrosine pretreatment=one week pretreatment only; desaminotyrosine day +2=treatment commenced 2 days postinfection (n=30 mice/group from two experiments). (FIG. 20B) Kaplan-Meier survival analysis of mice all treated with clodronate liposomes and either control or desaminotyrosine (n=18-20 mice/group from two experiments). (FIG. 20C) Kaplan-Meier survival analysis of infected wildtype and Irgm1$^{-/-}$ mice all treated with clodronate liposomes and either control or desaminotyrosine (n=9-13 mice/group from three experiments). (FIG. 20D, FIG. 20E, and FIG. 20F) Relative expression of matrix influenza mRNA from wildtype (FIG. 20D) and Ifnar$^{-/-}$ BMDMs (FIG. 20E) pretreated with or without desaminotyrosine and then infected (n=7 replicates/group from two experiments for wildtype BMDMs and 3 replicates/group from three experiments for Ifnar$^{-/-}$ BMDMs). (FIG. 20F) Matrix viral RNA expression determined by qRT-PCR from infected BMDMs from indicated genotypes (n=two to seven experiments). (FIG. 20G and FIG. 20H) Relative mRNA expression of Oas1 (FIG. 20G) and IP-10 (FIG. 20H) by qRT-PCR from wildtype and Ifnar$^{-/-}$ BMDMs pretreated with or without desaminotyrosine and then infected (n=7 replicates/group from two experiments for wildtype BMDMs and 3 replicates/group from three experiments for Ifnar$^{-/-}$ BMDMs). (FIG. 20I, FIG. 20J, and FIG. 20K) Relative mRNA expression of IP-10 by qRT-PCR from WT (FIG. 20I), Mavs$^{-/-}$ (FIG. 20J) and Stat1$^{-/-}$ (FIG. 20K) genotypes treated with polyIC and with or without desaminotyrosine (n=4). (FIG. 20L, FIG. 20M, and FIG. 20N) Relative mRNA expression of IP-10 by qRT-PCR from BMDMs from WT (FIG. 20L), Mavs$^{-/-}$ (FIG. 20M), and Stat1$^{-/-}$ (FIG. 20N) genotypes treated with type I IFN and with or without desaminotyrosine (n=4). Graphs denote average with SEM displayed. *p<0.05, p<0.01, *p<0.001, ****p<0.0001 and ns denotes not statistically significant. Mantel-Cox test used with or without Bonferroni-corrected threshold for statistical analysis in A, B, and C. Mann-Whitney test used in D-G. ANOVA in D (F=37.5) used Tukey's multiple comparisons test.

DETAILED DESCRIPTION OF THE INVENTION

Figure 1A:
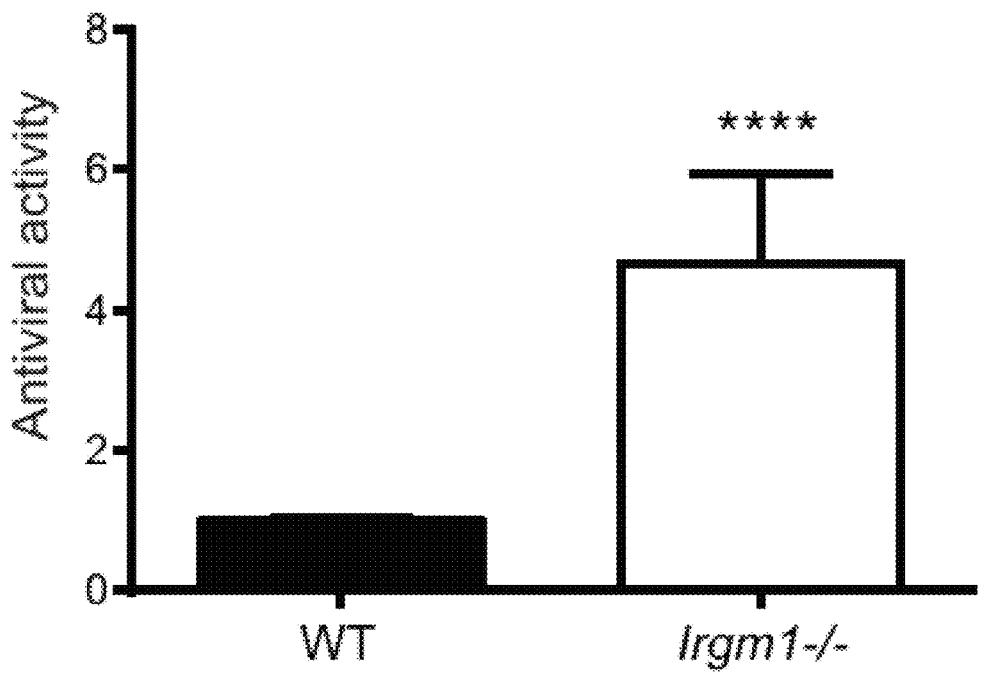
FIG. 1A, FIG. 1B, FIG. 1C, FIG. 1D, FIG. 1E, FIG. 1F, FIG. 1G, and FIG. 1H depict graphs showing that $Irgm1^{-/-}$ mice have elevated IFN in the lungs and are resistant to Influenza.

Provided herein is data showing that enhanced type I IFN signaling protects animals from Influenza-associated mortality. It is further discovered that desaminotyrosine can enhance type I IFN signaling and protect from Influenza infection. An examination of the effects of desaminotyrosine treatment revealed that desaminotyrosine promotes epithelial proliferation. Notably, desaminotyrosine repairs damaged intestinal epithelial. This discovery provides methods of promoting wound repair and treating inflammatory bowel diseases such as ulcerative colitis and Crohn's disease comprising administering desaminotyrosine. Various aspects of the disclosure are described in more detail below.

I. Compositions

In an aspect, a composition of the disclosure comprises desaminotyrosine or a desaminotyrosine derivative. Desaminotyrosine has the molecular formula $C_9H_{10}O_3$ and may also be referred to as phloretic acid, 3-(4-hydroxyphenyl) propanoic acid, hydro-p-coumaric acid, and phloretate. Desaminotyrosine has the chemical structure:

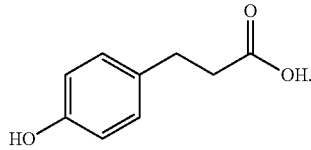 [SMILES: O=C(O)CCc1ccc(O)cc1]

Desaminotyrosine or desaminotyrosine derivatives may be modified to improve potency, bioavailability, solubility, stability, handling properties, or a combination thereof, as compared to an unmodified version. Thus, in another aspect, a composition of the disclosure comprises a modified desaminotyrosine or desaminotyrosine derivative. In still another aspect, a composition of the disclosure comprises a prodrug of a desaminotyrosine or desaminotyrosine derivative. In all instances, a desaminotyrosine derivative, a modified desaminotyrosine or a prodrug of desaminotyrosine functions as desaminotyrosine. For example, a desaminotyrosine derivative, a modified desaminotyrosine or a prodrug of desaminotyrosine enhances type I interferon stimulation and/or promotes epithelial proliferation. A skilled artisan would be able to determine if a desaminotyrosine derivative, a modified desaminotyrosine or a prodrug of desaminotyrosine behaves as desaminotyrosine. Desaminotyrosine derivatives are described in U.S. Pat. Nos. 5,099,060, 5,670,602, and RE37160 and are hereby incorporated by reference in their entirety.

A composition of the disclosure may optionally comprise one or more additional drug or therapeutically active agent in addition to the desaminotyrosine or desaminotyrosine derivative. A composition of the disclosure may further comprise a pharmaceutically acceptable excipient. The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising desaminotyrosine or a desaminotyrosine derivative is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of desaminotyrosine or a desaminotyrosine derivative in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, desaminotyrosine or a desaminotyrosine derivative may be selectively delivered to a cell by encapsulation in a liposome that fuses with the targeted cell's membrane.

Liposomes may be comprised of a variety of different types of phospholids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethyl indocarbocyanine perchloarate, 1,1'-dioleyl-3,3,3',3'-tetramethyl indo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying desaminotyrosine or a desaminotyrosine derivative may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211, and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration, and composition of lipid, concentration of multivalent cations, rate of mixing, presence of and concentration of solvent.

In another embodiment, a composition of the disclosure may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. Desaminotyrosine or a desaminotyrosine derivative may be encapsulated in a microemulsion by any method generally known in the art.

In yet another embodiment, desaminotyrosine or a desaminotyrosine derivative may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods

In an aspect, the disclosure provides a method to enhance type I interferon stimulation in a subject, the method comprising administering to the subject a composition comprising desaminotyrosine or a desaminotyrosine derivative. Methods to determine type I interferon stimulation are known in the art. For example, the activity of IFN-stimulated response elements (ISRE) may be measured. Accordingly, a desaminotyrosine derivative of the disclosure increases ISRE activity. The inventors have discovered that enhancing type I interferon stimulation in a subject prevents or reduces influenza-associated symptoms. Accordingly, the disclosure provides a method to prevent or reduce influenza-associated symptoms comprising enhancing type I interferon stimulation in a subject.

In another aspect, the disclosure provides a method to prevent or reduce influenza-associated symptoms in a subject, the method comprising administering to the subject a composition comprising desaminotyrosine or a desaminotyrosine derivative. Non-limiting examples of influenza-associated symptoms include fever, chills, cough, sore throat, runny or stuffy nose, muscle or body aches, headaches, fatigue, vomiting, and diarrhea. In certain embodiments, the composition comprising desaminotyrosine or a desaminotyrosine derivative is administered to the subject prior to infection with influenza. Accordingly, the composition comprising desaminotyrosine or a desaminotyrosine derivative is administered prophylactically to the subject. The subject may be a subject that is at risk of infection with influenza. Non-limiting examples of subjects at risk of infection with influenza include children and infants, pregnant women, seniors, people with health conditions, and travelers. Additionally, the subject may be subject that is at a high risk for complications from influenza. Non-limiting examples of a subject that is at a high risk for complications form influenza include a subject with asthma, a subject with an endocrine disorder (such as diabetes), a subject with heart disease (such as congenital heart disease, congestive heart failure and coronary artery disease), a subject who has had a stroke, a subject 65 years or older, a pregnant subject (or up to two weeks postpartum), a subject younger than 5 years, especially younger than 2 years, a subject that is a resident of a nursing home or other long-term care facility, a subject that is American Indian or Alaskan Native, a subject with neurological and neurodevelopmental conditions (including disorders of the brain, spinal cord, peripheral nerve, and muscle such as cerebral palsy, epilepsy, stroke, intellectual disability, moderate to severe developmental delay, muscular dystrophy, or spinal cord injury), a subject with chronic lung disease (such as chronic obstructive pulmonary disease [COPD] and cystic fibrosis), a subject with a blood disorder (such as sickle cell disease), a subject with a kidney disorder, a subject with a liver disorder, a subject with a metabolic disorder (such as inherited metabolic disorders and mitochondrial disorders), a subject with a weakened immune system due to disease or medication (such as a subject with HIV or AIDS, or cancer, or a subject on chronic steroids), a subject younger than 19 years of age who is receiving long-term aspirin therapy, and a subject with extreme obesity (body mass index [BMI] of 40 or more).

In still another aspect, the disclosure provides a method to promote epithelial tissue proliferation in a subject, the method comprising administering to the subject a composition comprising desaminotyrosine or a desaminotyrosine derivative. Epithelial tissues line the cavities and surfaces of blood vessels and organs throughout the body. In certain embodiments, the epithelial tissue includes the skin, mouth, esophagus, lungs, gastrointestinal tract, reproductive tract, urinary tract, exocrine glands, and endocrine glands. In a specific embodiment, the epithelial tissue is the gastrointestinal tract. The gastrointestinal tract includes the esophagus, stomach, small intestines (i.e., duodenum, jejunum, and ileum) and large intestine (also referred to as the colon and includes cecum, rectum, anal canal, and appendix). Specifically, the epithelial tissue may be the colon. When the epithelial tissue is the colon, desaminotyrosine or a desaminotyrosine derivative restores or increases crypt height. Epithelial tissue proliferation may be measured by methods known in the art such as visual and microscopic examination or measuring cellular markers for proliferation such as Ki-67.

In still yet another aspect, the disclosure provides a method to promote wound repair in a subject, the method comprising administering to the subject a composition comprising desaminotyrosine or a desaminotyrosine derivative. The wound is a wound that would benefit from epithelial proliferation. The wound may be found at a mucosal site. Non-limiting examples of mucosal sites include the bronchial mucosa and the lining of vocal folds, endometrium, esophageal mucosa, gastric mucosa, intestinal mucosa, nasal mucosa, olfactory mucosa, oral mucosa, penile mucosa, and vaginal mucosa. The wound may include a denuded epithelium or an epithelium with altered structure. The wound may be due to surgery, injury, and/or inflammation. Specifically, the wound may be located in the gastrointestinal tract. Specifically, when the wound is located in the gastrointestinal tract, desaminotyrosine or a desaminotyrosine derivative may restore the normal structure of the epithelium (i.e. restore crypt presence and height).

In a different aspect, the disclosure provides a method to treat colitis in a subject, the method comprising administering to the subject a composition comprising desaminotyrosine or a desaminotyrosine derivative. The colitis may be due to infection, inflammatory bowel disease (e.g., Crohn's disease or ulcerative colitis), ischemic colitis, allergic reactions, and/or microscopic colitis. Specifically, the colitis is inflammatory bowel disease. Accordingly, the disclosure provides a method to treat inflammatory bowel disease in a subject, the method comprising administering to the subject a composition comprising desaminotyrosine or a desaminotyrosine derivative. The inflammatory bowel disease may be ulcerative colitis or Crohn's disease. The term "treat," "treating," or "treatment" as used herein refers to administering desaminotyrosine or a desaminotyrosine derivative for prophylactic and/or therapeutic purposes. The term "prophylactic treatment" refers to treating a subject who is not yet symptomatic, but who is susceptible to, or otherwise at a risk of symptoms. The term "therapeutic treatment" refers to administering treatment to a subject already suffering from symptoms of colitis. The term "treat," "treating," or "treatment" as used herein also refers to administering an agent in order to: (i) reduce or eliminate either colitis or one or more symptoms of colitis, or (ii) retard the progression of colitis or of one or more symptoms of colitis, or (iii) reduce the severity of colitis or of one or more symptoms of colitis, or (iv) suppress the clinical manifestation of colitis, or (v) suppress the manifestation of adverse symptoms of colitis.

The subject may or may not be diagnosed with colitis. The subject may not be diagnosed with colitis but suspected of having colitis based on symptoms. Non-limiting examples of symptoms of colitis include abdominal pain, cramping, bloating, diarrhea with or without blood in the stool, fever, chills, fatigue, dehydration, eye inflammation, joint swelling, canker sores, and skin inflammation. In other embodiments, the subject may not be diagnosed with colitis but is at risk of having colitis. Non-limiting examples of risk factors for colitis are known to those of skill in the art and may include living in Western countries, age, smoking, appendectomy, family history, parasite exposure, medication, diet, ethnicity, and bacteria in the colon. In other embodiments, the subject has no symptoms and/or no risk factors for colitis. Methods of diagnosing colitis are known to those of skill in the art and may include blood and fecal matter tests, endoscopy, sigmoidoscopy, colonoscopy, biopsy, and chromoendoscopy.

Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. In a preferred embodiment, the subject is human.

In certain aspects, a pharmacologically effective amount of desaminotyrosine or a desaminotyrosine derivative may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, topical, transdermal, intramuscular, intranasal, oral, buccal, sublingual, or suppository administration. Local administration, including directly into the central nervous system (CNS) includes but is not limited to via a lumbar, intraventricular or intraparenchymal catheter or using a surgically implanted controlled release formulation. In certain embodiments, desaminotyrosine or a desaminotyrosine derivative is administered orally.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the compounds useful in this discovery, making them more lipophilic, for example, by encapsulating them in liposomes or by blocking polar groups.

A therapeutically effective amount of desaminotyrosine or a desaminotyrosine derivative is administered to a subject. A "therapeutically effective amount" is an amount of the therapeutic composition sufficient to produce a measurable biological response (e.g., type I interferon stimulation, reduction in symptoms associated with influenza infection, epithelial proliferation, wound repair, reduction in symptoms associated with colitis). Actual dosage levels of active ingredients in a therapeutic composition of the disclosure can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, colitis symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In certain embodiments, the dose may range from about 0.01 g to about 10 g. For example, the dose may range from about 0.1 g to about 5 g, or from about 0.5 g to about 5 g, or from about 1 g to about 10 g, or from about 1 g to about 5 g. Additionally, the dose may be about 0.01 g, about 0.05 g, about 0.1 g, about 0.2 g, about 0.3 g, about 0.4 g, about 0.5 g, about 0.6 g, about 0.7 g, about 0.8 g, about 0.9 g, about 1 g, about 1.1 g, about 1.2 g, about 1.3 g, about 1.4 g, about 1.5 g, about 1.6 g, about 1.7 g, about 1.8 g, about 1.9 g, about 2 g, about 2.1 g, about 2.2 g, about 2.3 g, about 2.4 g, about 2.5 g, about 2.6 g, about 2.7 g, about 2.8 g, about 2.9 g, about 3 g, about 3.1 g, about 3.2 g, about 3.3 g, about 3.4 g, about 3.5 g, about 3.6 g, about 3.7 g, about 3.8 g, about 3.9 g, about 4 g, about 4.1 g, about 4.2 g, about 4.3 g, about 4.4 g, about 4.5 g, about 4.6 g, about 4.7 g, about 4.8 g, about 4.9 g, about 5 g, about 6 g, about 6.5 g, about 7 g, about 7.5 g, about 8 g, about 8.5 g, about 9 g, about 9.5 g, about 10 g, or more than 10 g.

The frequency of dosing may be once, twice or three times or more daily or once, twice, three times or more per week or per month, as needed as to effectively treat the symptoms. For example, the frequency of dosing may be once, twice, or three times daily for one week, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, 12 months, 2 years, 3 years, 4 years, 5 years, or more than 5 years. Additionally, the frequency of dosing may be once daily for one week, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, 12 months, 2 years, 3 years, 4 years, 5 years, or more than 5 years. In certain embodiments, the duration of treatment could range from a single dose administered on a one-time basis to a life-long course of therapeutic treatments.

The timing of administration of the treatment relative to the disease itself and duration of treatment will be determined by the circumstances surrounding the case. Treatment could begin immediately. Treatment could begin in a hospital or clinic itself, or at a later time after discharge from the hospital or after being seen in an outpatient clinic.

Although the foregoing methods appear the most convenient and most appropriate and effective for administration of desaminotyrosine or a desaminotyrosine derivative, by suitable adaptation, other effective techniques for administration, such as intravenous administration, intraventricular administration, and transdermal administration may be employed provided proper formulation is utilized herein.

In addition, it may be desirable to employ controlled release formulations using biodegradable films and matrices, or osmotic mini-pumps, or delivery systems based on dextran beads, alginate, or collagen.

In certain aspects, the methods of the disclosure may further comprise administering therapy standard for the treatment of colitis. Suitable therapy for colitis is known in the art, and will depend upon the type and symptoms of colitis. Non-limiting examples of therapy for colitis include rehydration, medication, antibiotics if a specific bacteria is isolated and treatment is known to shorten the course of the infectious colitis, and diet changes.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 1B:
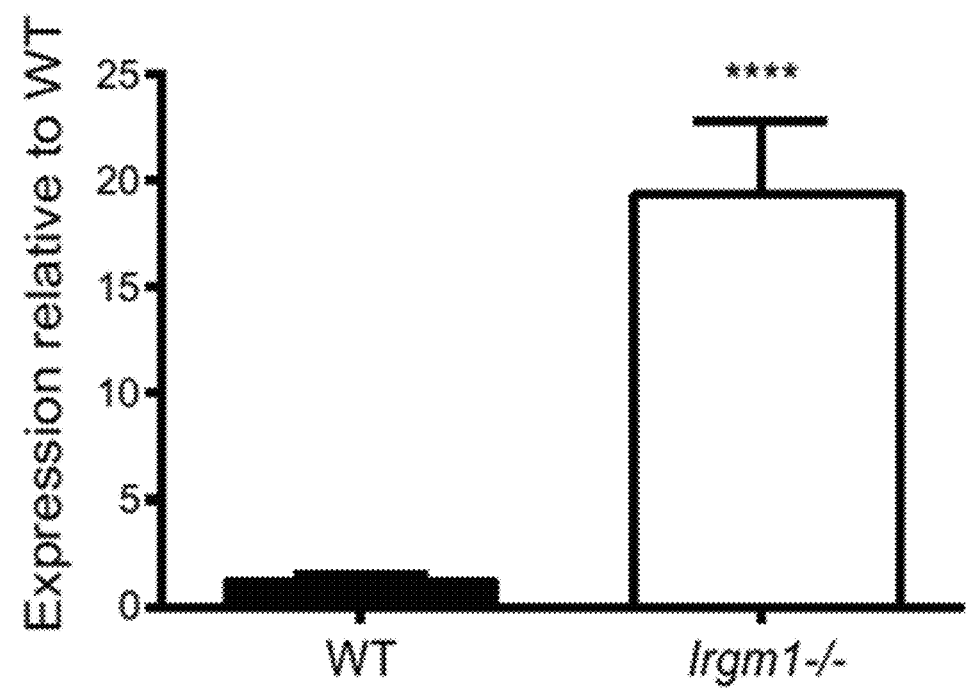
Figure 1C:
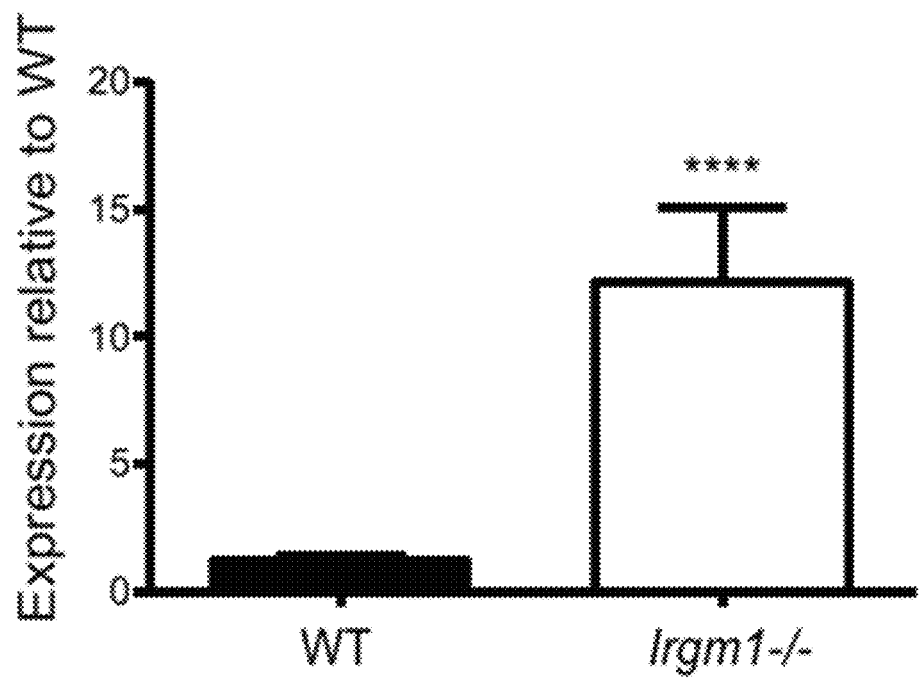

Example 1. Genetically and Environmentally Enhanced Type I Interferon Protects from Influenza To test the hypothesis that enhanced type I IFN signaling alters the severity of the host response to Influenza infection, Irgm1 mice were utilized, a model with elevated systemic IFNα activity. This model mimics the effects of chronic viral infection in multiple organs.[12] Here, multiple assays were utilized that demonstrated the lungs of Irgm1$^{-/-}$ mice had elevated type I IFNs. First, a bioassay of whole lung tissue homogenate showed elevated type I IFN activity of Irgm1$^{-/-}$ mice as compared to material from littermate controls (FIG. 1A). Second, qRT-PCR analysis of classic Type I IFN responsive transcripts, Oas2 and Mx2, showed enrichment in the lung tissue of Irgm1$^{-/-}$ mice (FIG. 1B and FIG. 1C). Third, analysis of total RNA sequencing of control and Irgm1$^{-/-}$ lungs from adult mice confirmed a robust signature for elevated type I IFN signaling (Table 1).

Figure 1D:
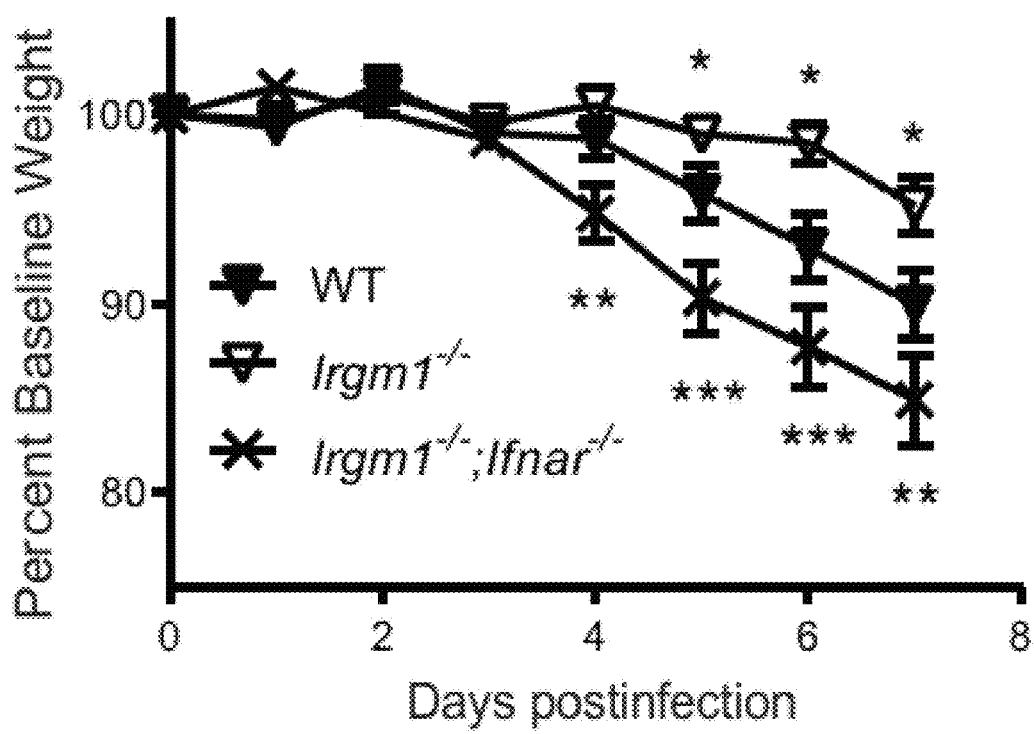
Figure 1E:
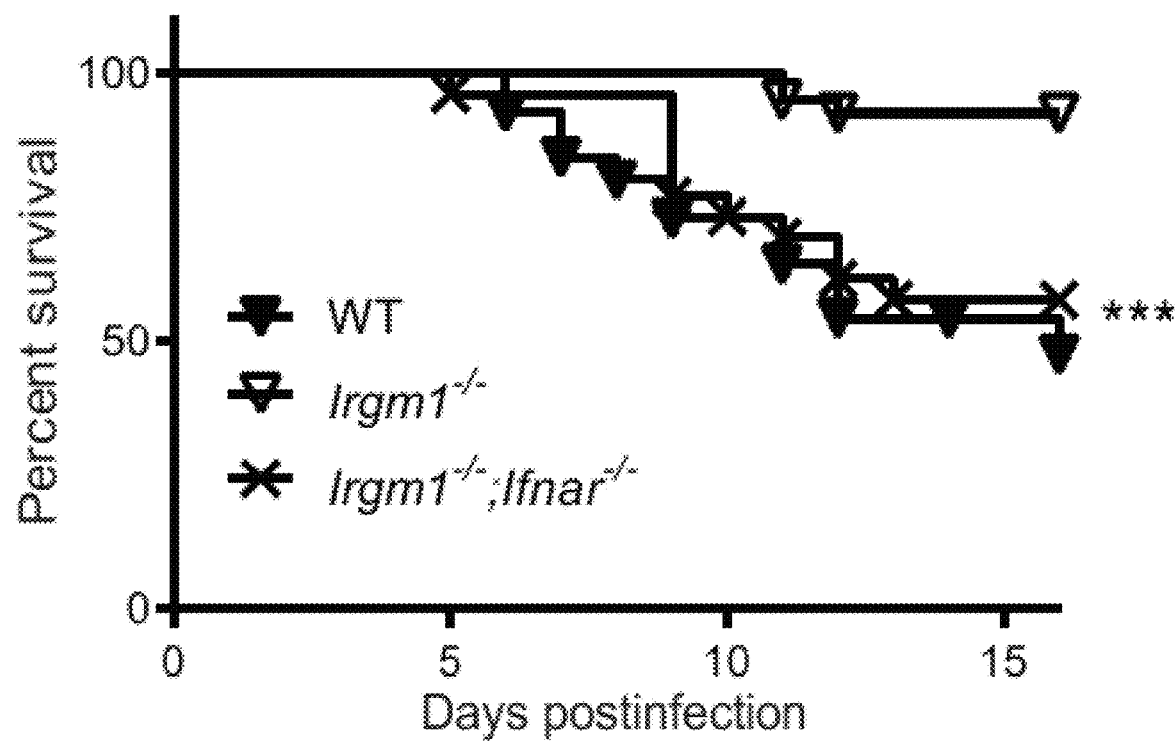
Figure 1F:
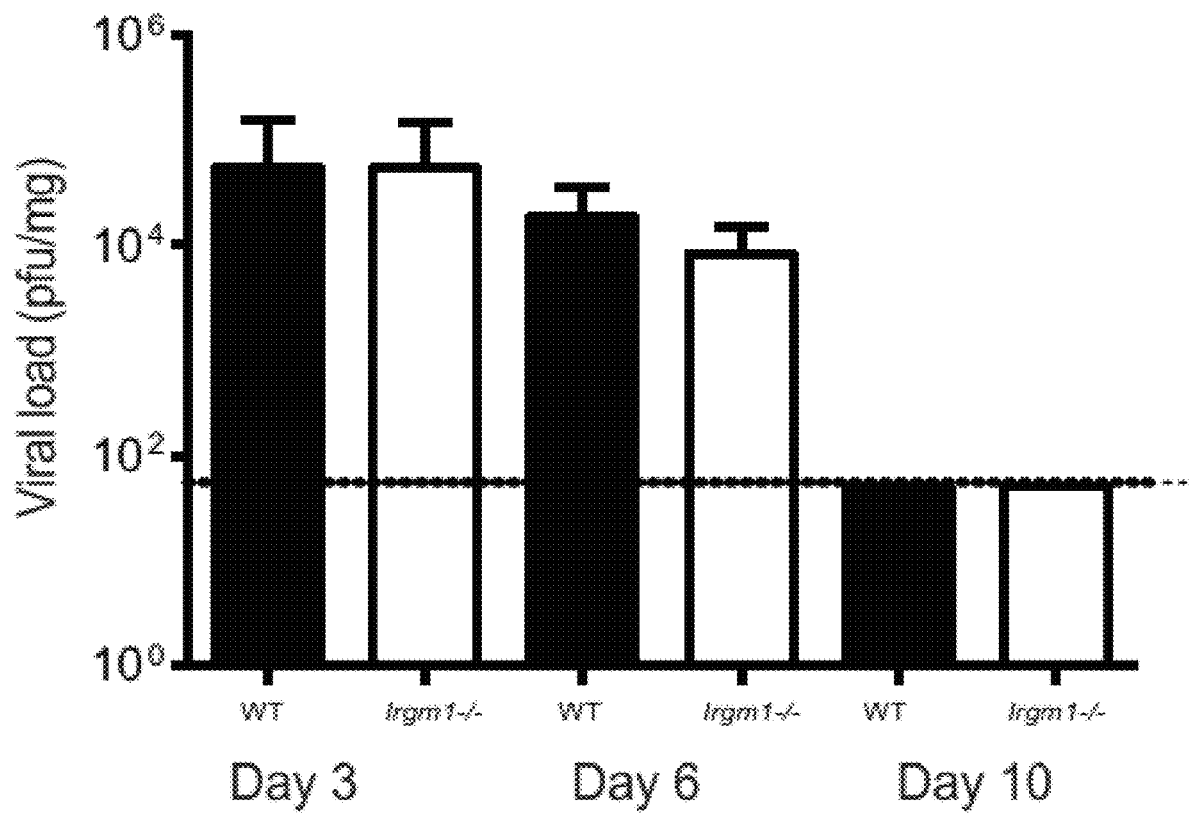
Figure 1G:
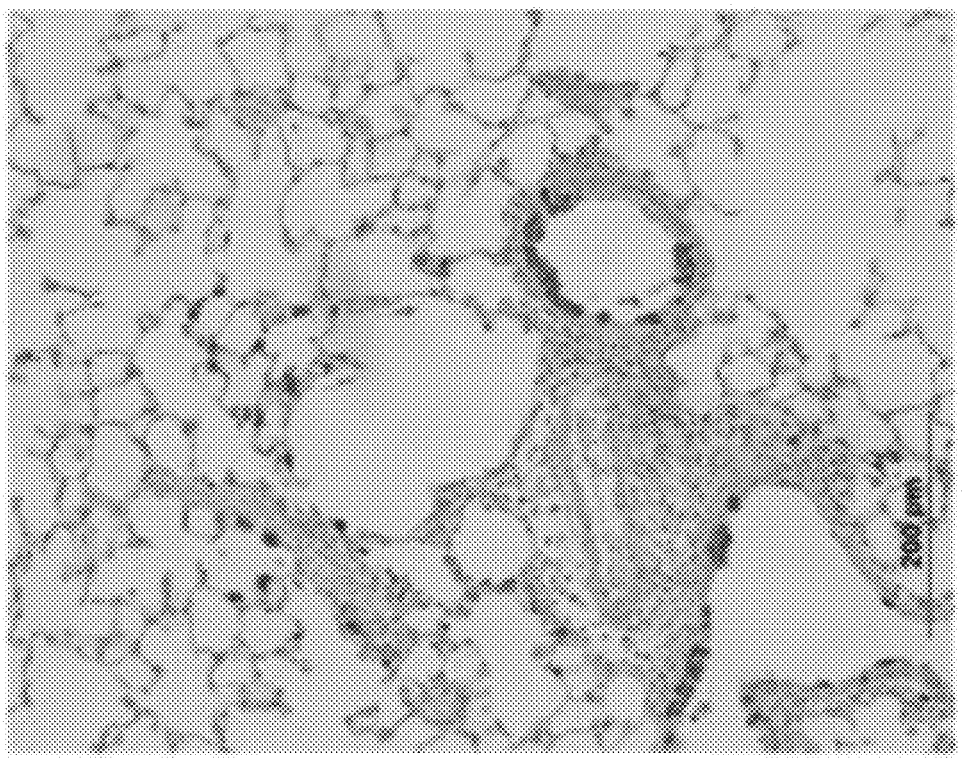
Figure 1H:
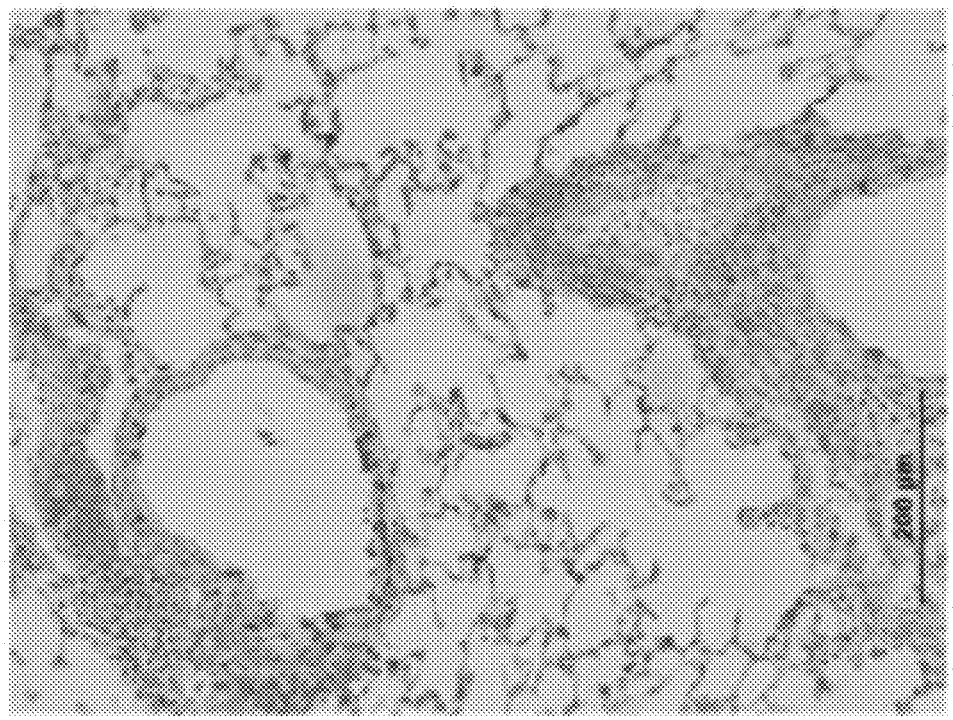
Figure 5A:
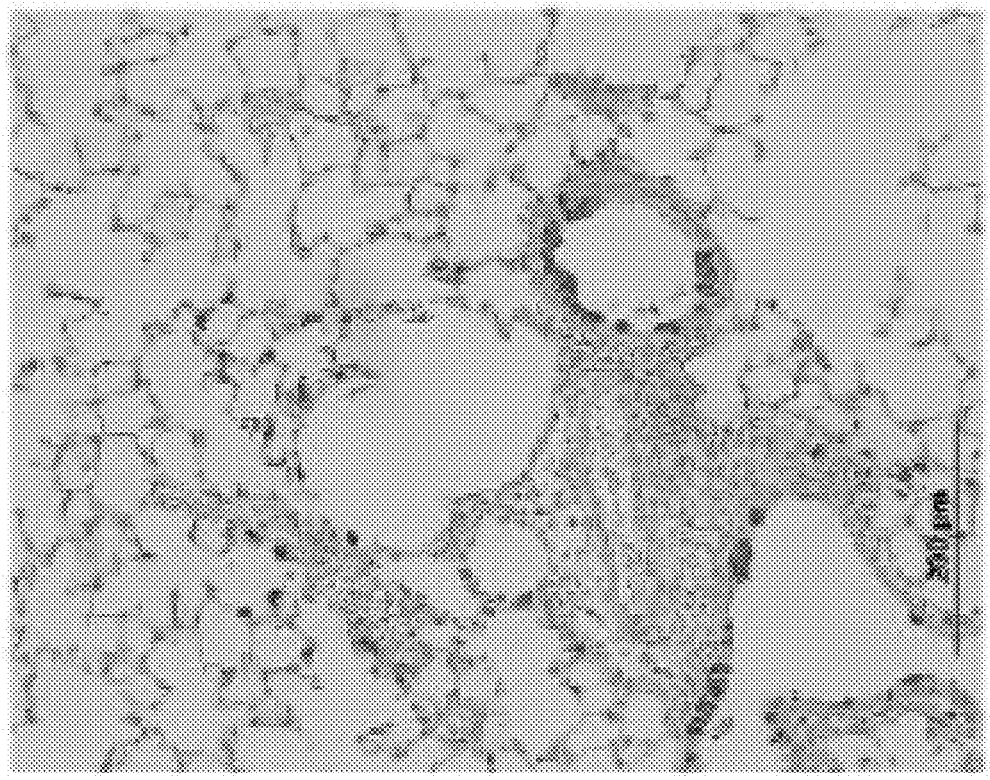
FIG. 5A and FIG. 5B depict images showing that Irgm1$^{-/-}$ (FIG. 5B) and littermate control (FIG. 5A) mice have similar viral location as shown by Influenza H1N1 immunohistological staining of infected littermate control and Irgm1$^{-/-}$ lung cross sections 6 days postinfection.
Figure 5B:
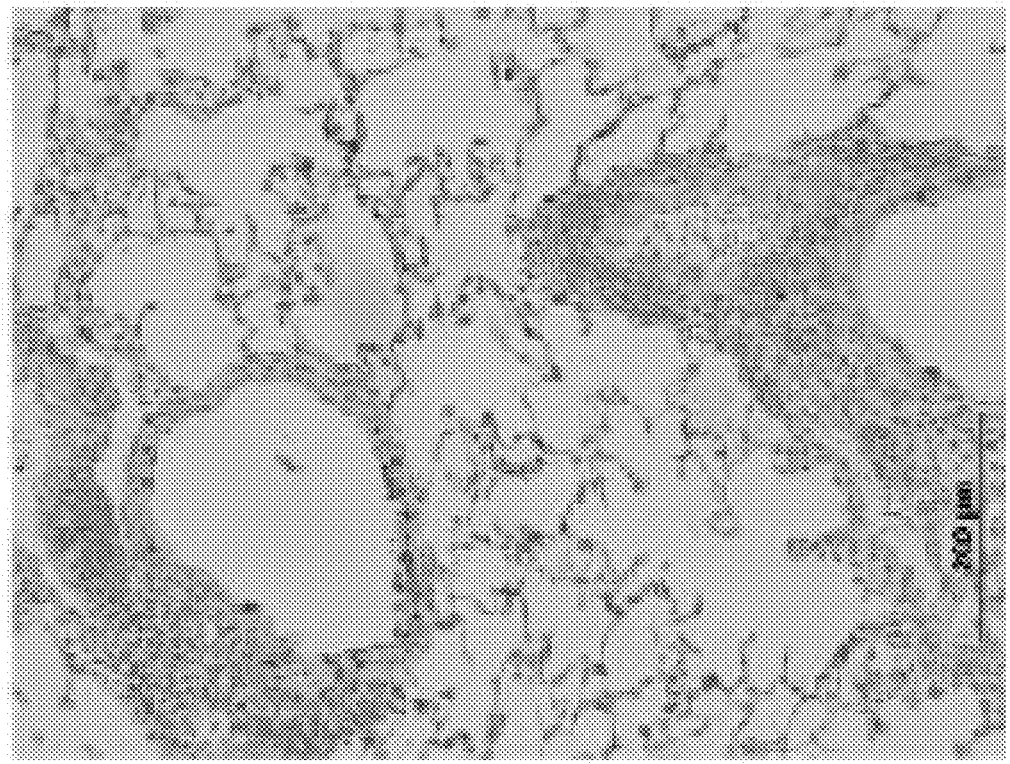
Figure 6A:
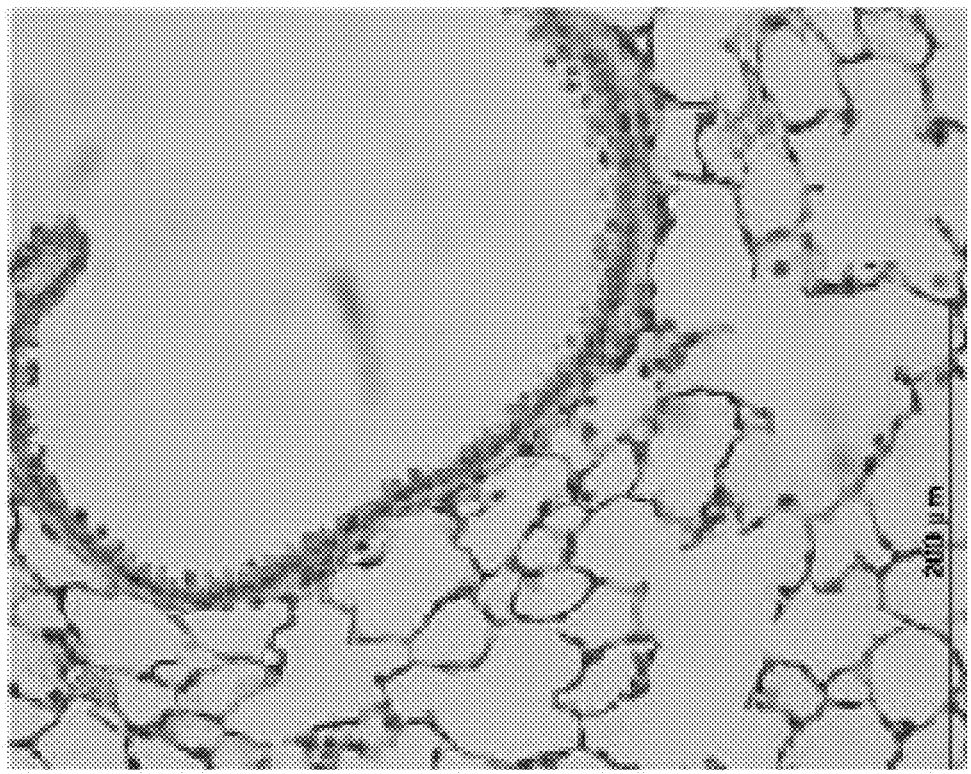
FIG. 6A and FIG. 6B depict images showing that uninfected Irgm1$^{-/-}$ mice have lung aggregates. Higher magnification of representative images of uninfected lung cross sections from littermate control (FIG. 6A) and Irgm1$^{-/-}$ (FIG. 6B) mice.
Figure 6B:
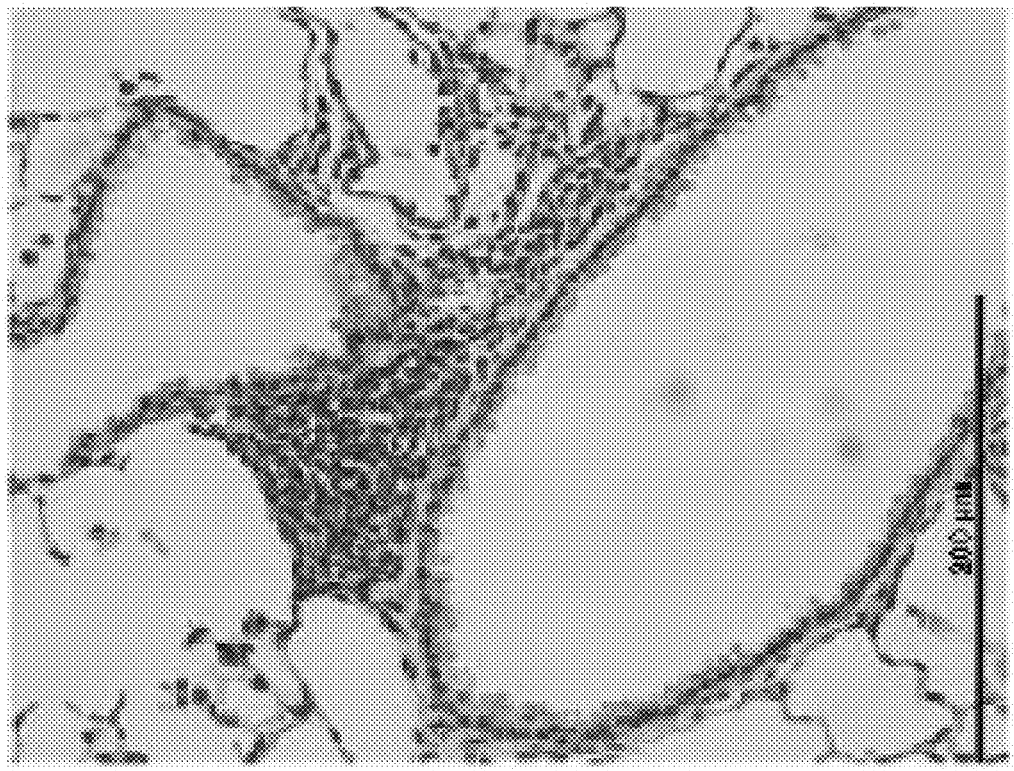
Figure 24:
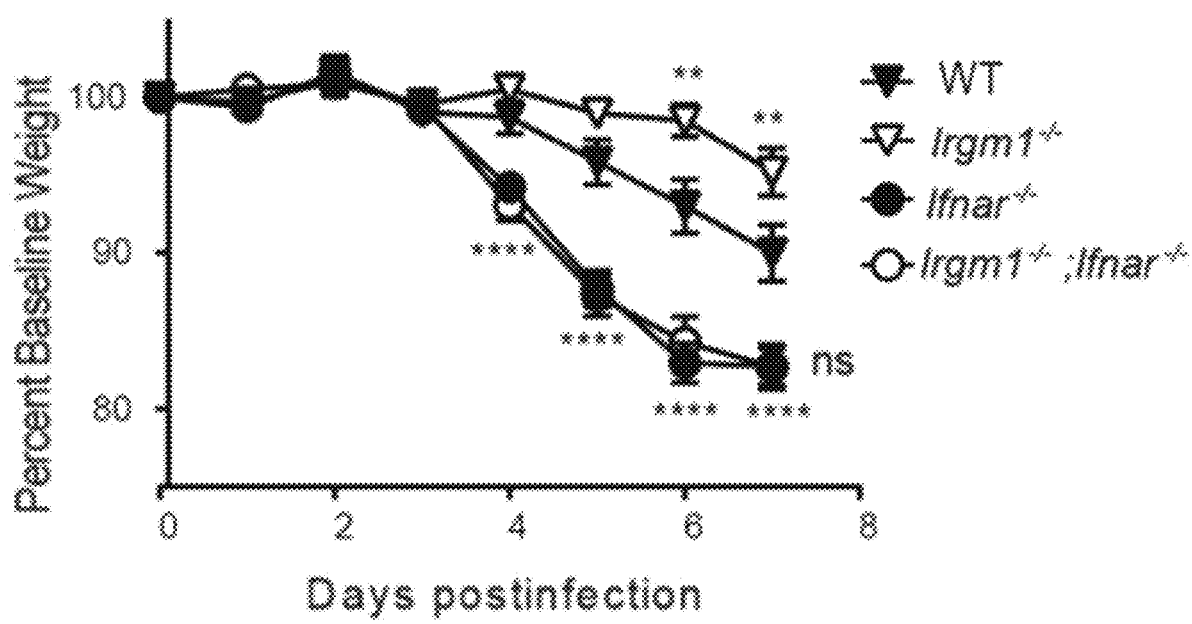
FIG. 24 depicts a graphs showing percent weight loss from baseline of infected control, Irgm1$^{-/-}$, Ifnar$^{-/-}$, and Irgm1$^{-/-}$;Ifnar$^{-/-}$ mice. (n=18-40 mice per group from three to five experiments). Asterisk on top represents significance between wild-type (WT) and Irgm1$^{-/-}$ mice, and asterisk on bottom represents significance between Irgm1$^{-/-}$ and Irgm1$^{-/-}$;Ifnar$^{-/-}$ mice. ns denotes nonsignificance between Ifnar$^{-/-}$ and Irgm1$^{-/-}$;Ifnar$^{-/-}$ mice. p<0.01, **p<0.0001 by ANOVA with Tukey's multiple comparisons.

As type I IFN activity was elevated in the lung tissue of Irgm1$^{-/-}$ mice, the effect of Influenza (strain A H1N1) infection was tested. As a readout of morbidity in these experiments, it was found that weight loss was greater during the first week postinfection in control littermate mice as compared to Irgm1$^{-/-}$ mice (FIG. 1D). Ultimately, a dosage of Influenza that caused a 50% mortality of littermate control mice showed minimal mortality in Irgm1$^{-/-}$ mice indicating that Irgm1 deficiency was protective during Influenza infection (FIG. 1E). Intriguingly, lungs of Irgm1$^{-/-}$ mice had similar viral titers, kinetics, and viral antigen location as controls suggesting that Irgm1 deficiency does not alter infectivity or virus propagation (FIG. 1F, FIG. 5A, and FIG. 5B). To verify the role of Type I IFN signaling in this model, a double knockout strain of Irgm1$^{-/-}$; Ifnar$^{-/-}$ mice was created. Influenza resulted in similar mortality and enhanced weight loss compared to controls (FIG. 1D, FIG. 1E, and FIG. 24). These experiments established that the elevated Type I IFNs in Irgm1$^{-/-}$ mice were associated with protection from Influenza infection in a type I IFN-dependent mechanism.

Figure 2A:
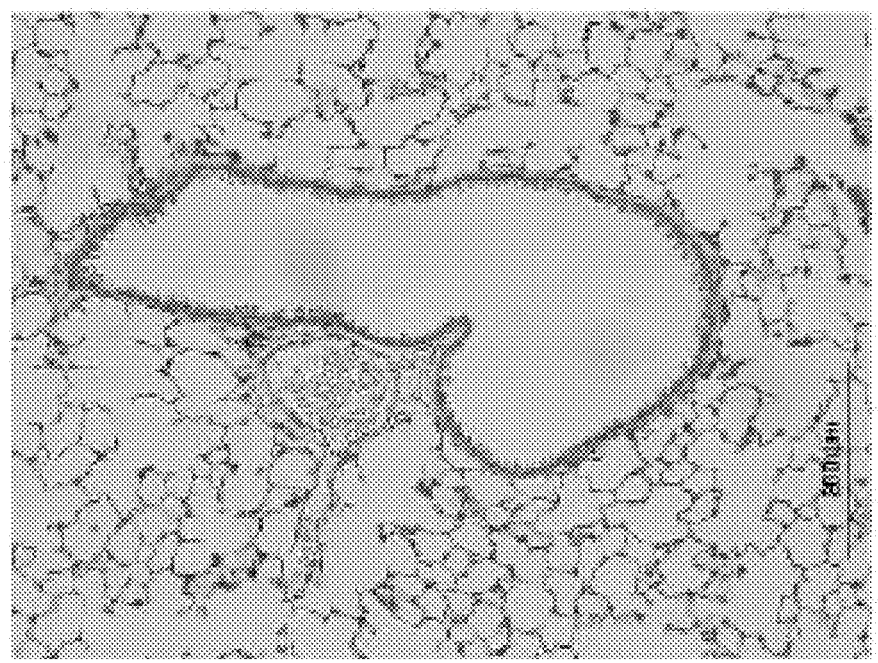
Figure 2B:
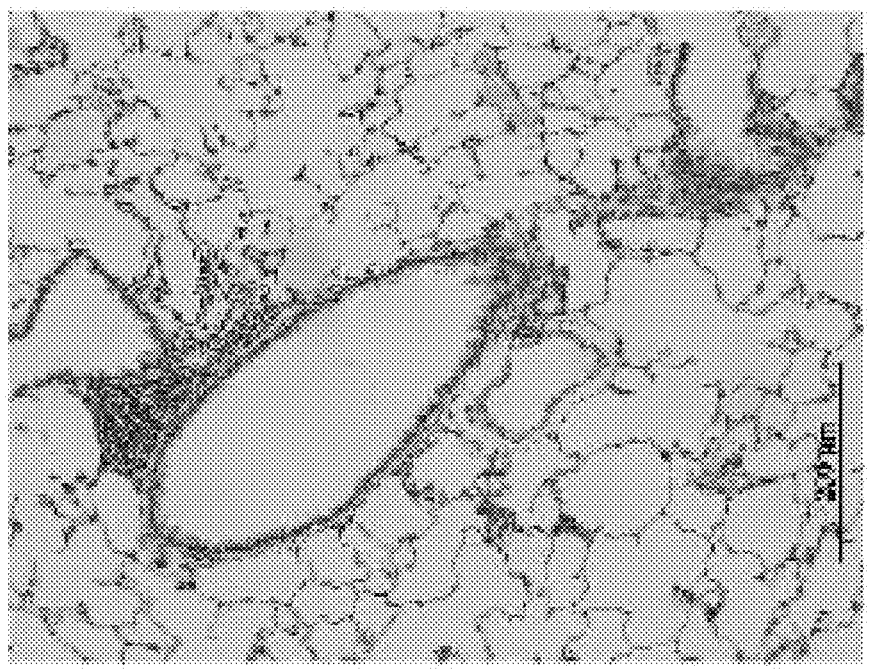
Figure 2C:
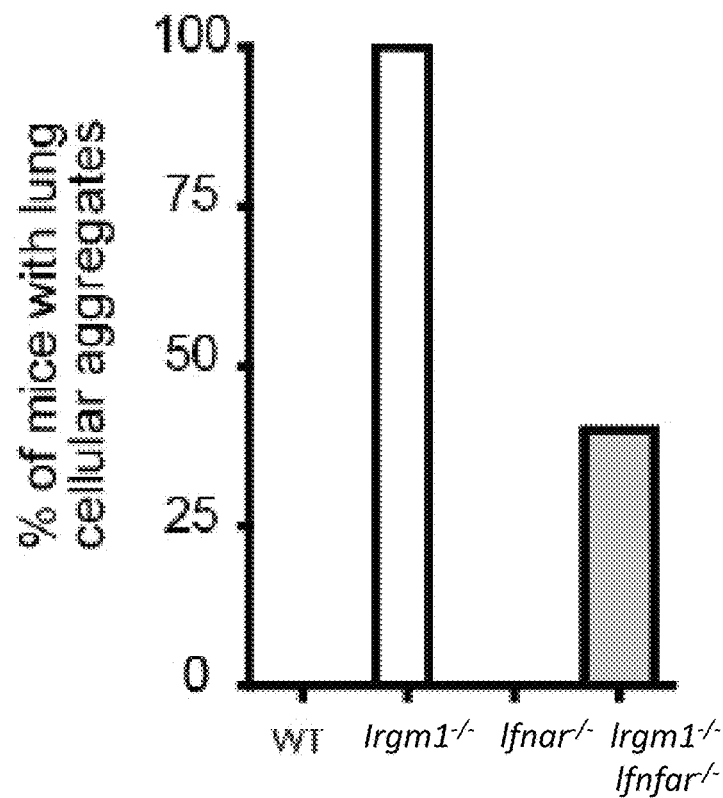
Figure 2D:
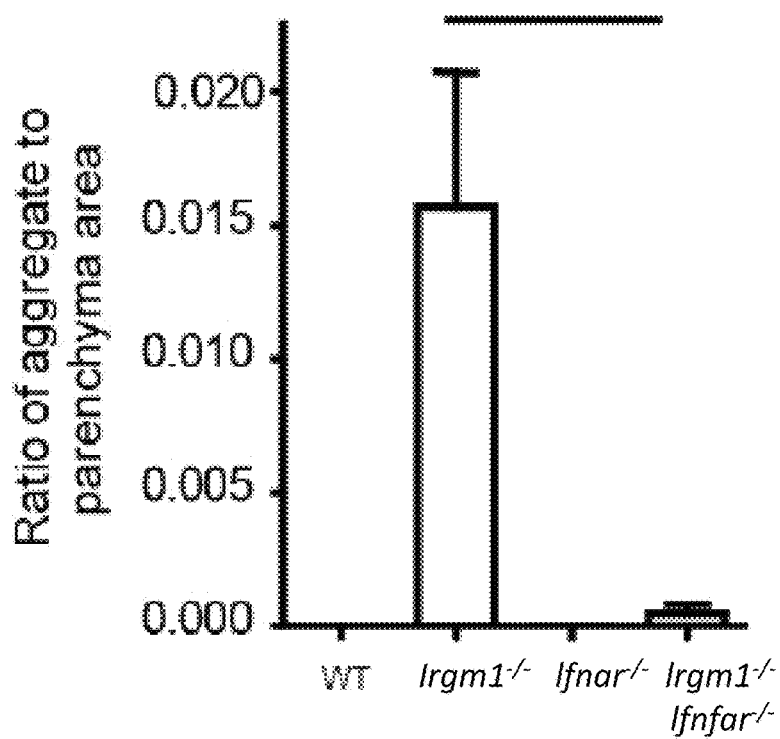
Figure 2E:
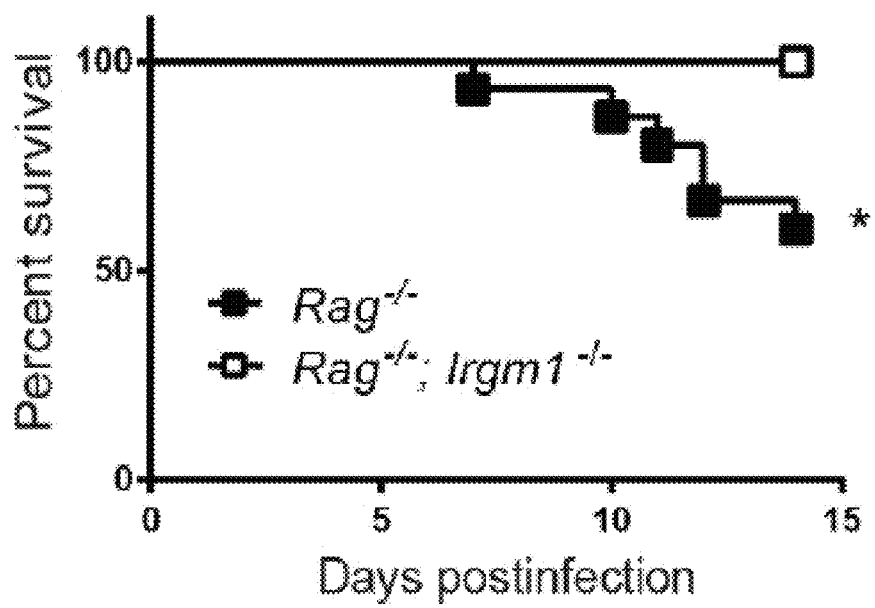
Figure 7A:
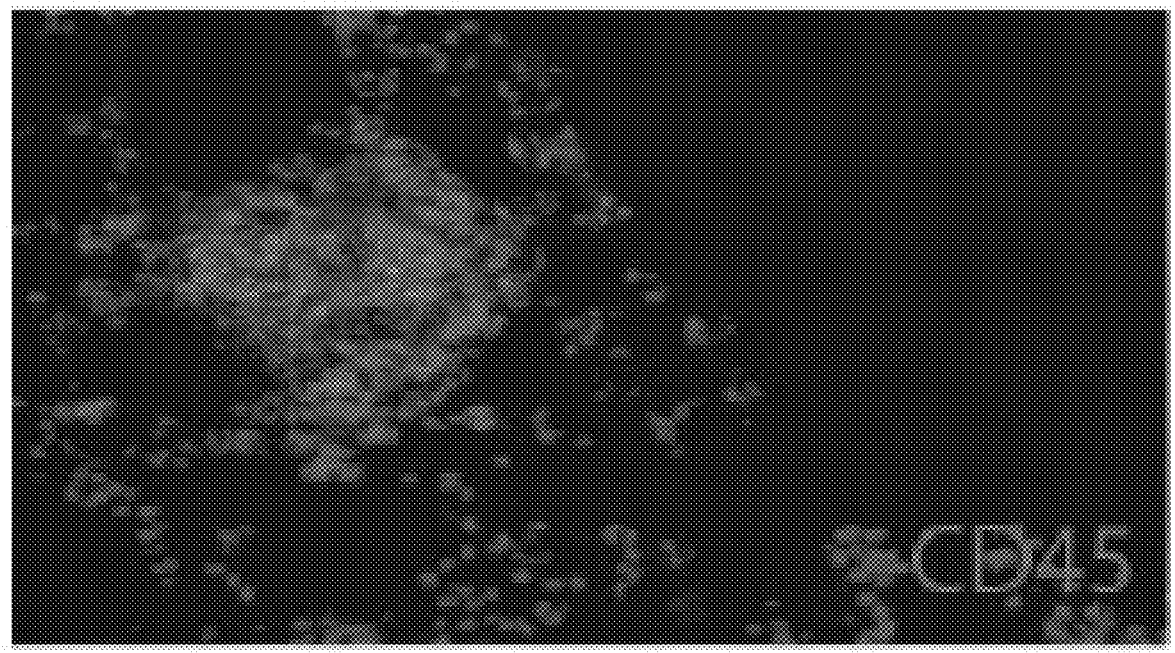
FIG. 7A, FIG. 7B, and FIG. 7C depicts images showing that lung aggregates in Irgm1$^{-/-}$ mice were composed of a mixed lymphocyte population. Representative immunofluorescence images of lung aggregates in Irgm1$^{-/-}$ mice.
Figure 7B:
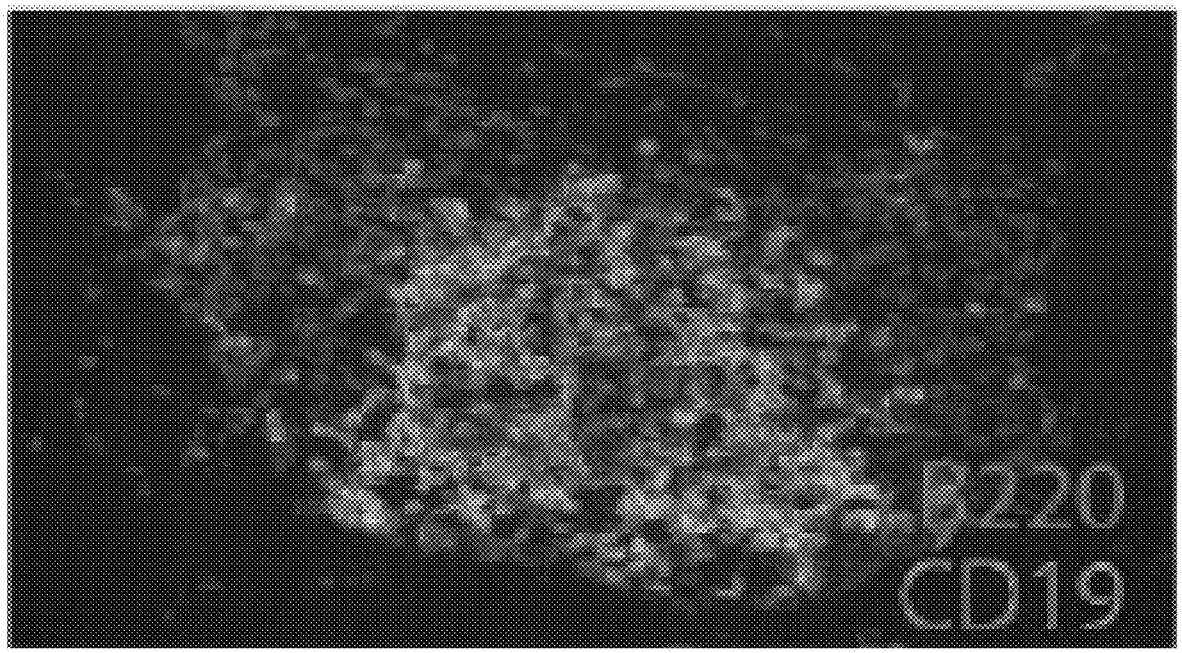
Figure 7C:
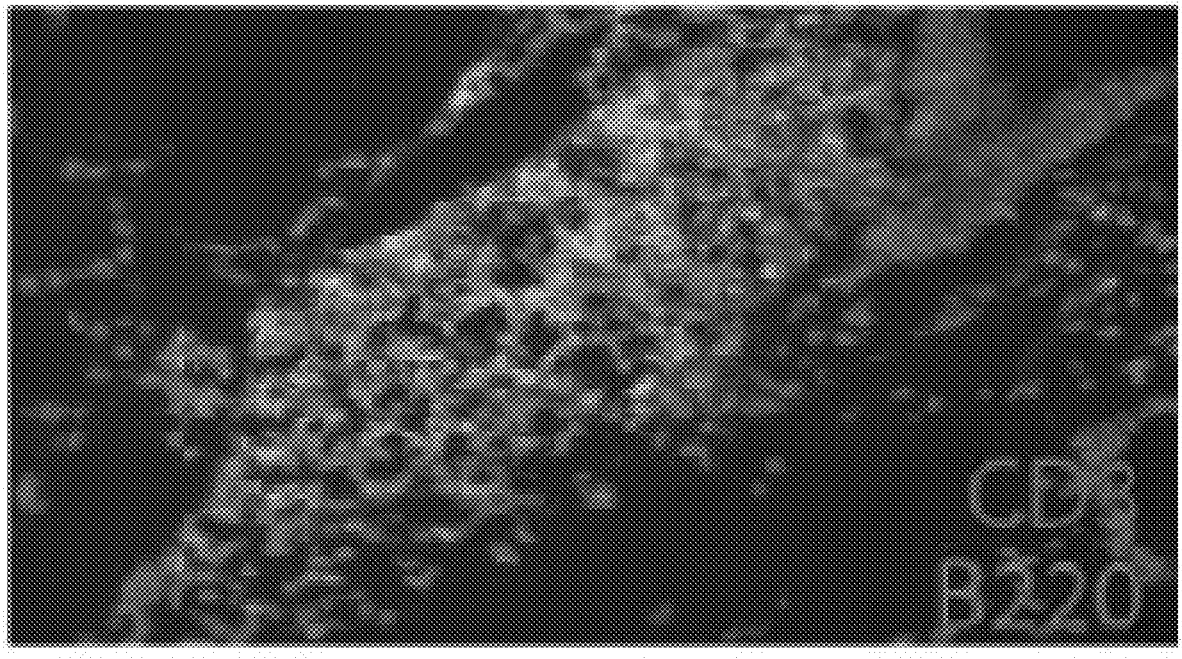
Figure 8:
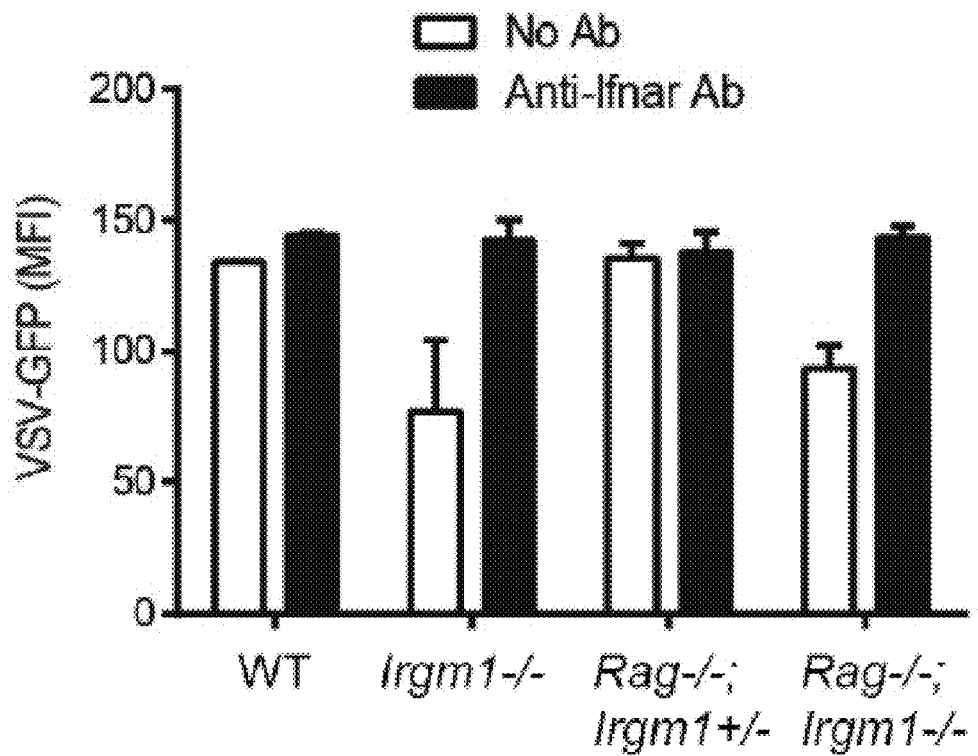
FIG. 8 depicts a graph showing that T and B cells were not required for elevated Type I IFN production in Irgm1$^{-/-}$ mice. VSV infectivity in the serum of indicated mice. Specificity for Type I IFN is shown by the addition of anti-Ifnar antibody (Ab). n=2-3 mice per group.

Histological analysis of lungs from uninfected Irgm1$^{-/-}$ mice showed the presence of robust bronchus associated lymphoid tissue (BALT) (FIG. 2A, FIG. 2B, FIG. 6A, and FIG. 6B). These cellular aggregates were found in all Irgm1$^{-/-}$ mice but were absent in all control littermates (FIG. 2C). The presence of BALT was largely dependent on Type I IFN as Irgm1$^{-/-}$;Ifnar$^{-/-}$ mice had greatly reduced or absent BALT (FIG. 2C and FIG. 2D). The BALT in Irgm1$^{-/-}$ mice was primarily composed of lymphocytes, specifically a core of B-cells surrounded by T-cells (FIG. 7A, FIG. 7B, and FIG. 7C). Based on these findings, the role of the adaptive immune system was tested in the resistant of Irgm1$^-$ mice to Influenza. Rag1$^{-/-}$ mice, lacking mature B and T cells, showed enhanced mortality 14 days after infection compared to Influenza-infected Irgm1$^{-/-}$; Rag1$^{-/-}$ (FIG. 2E). Since Irgm1$^{-/-}$; Rag1$^{-/-}$ mice maintained elevated levels of type I IFN as compared to controls (FIG. 8), without being bound by theory, it was concluded that type I IFN-dependent alterations to innate immunity contribute to protection from Influenza A virus infection.

Figure 2F:
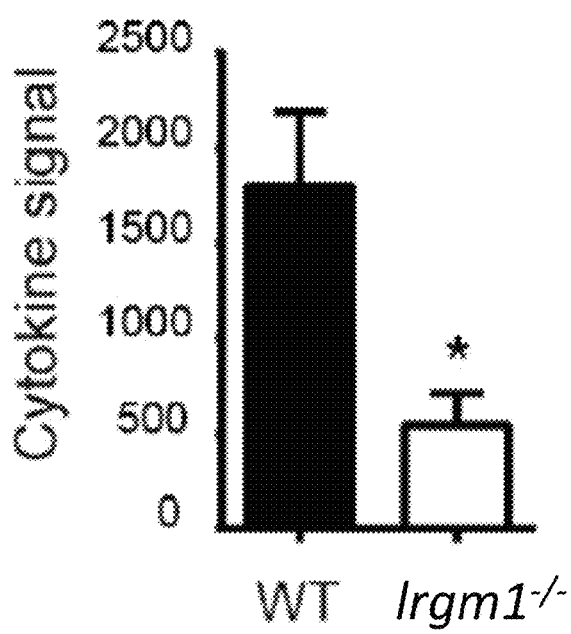
Figure 2G:
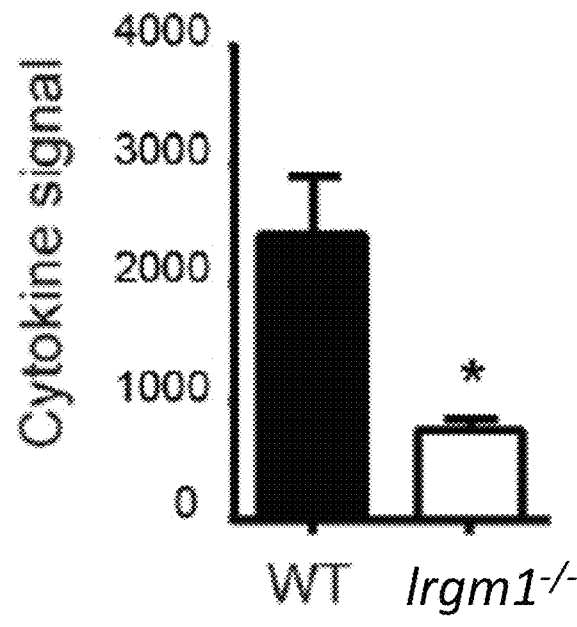
Figure 2K:
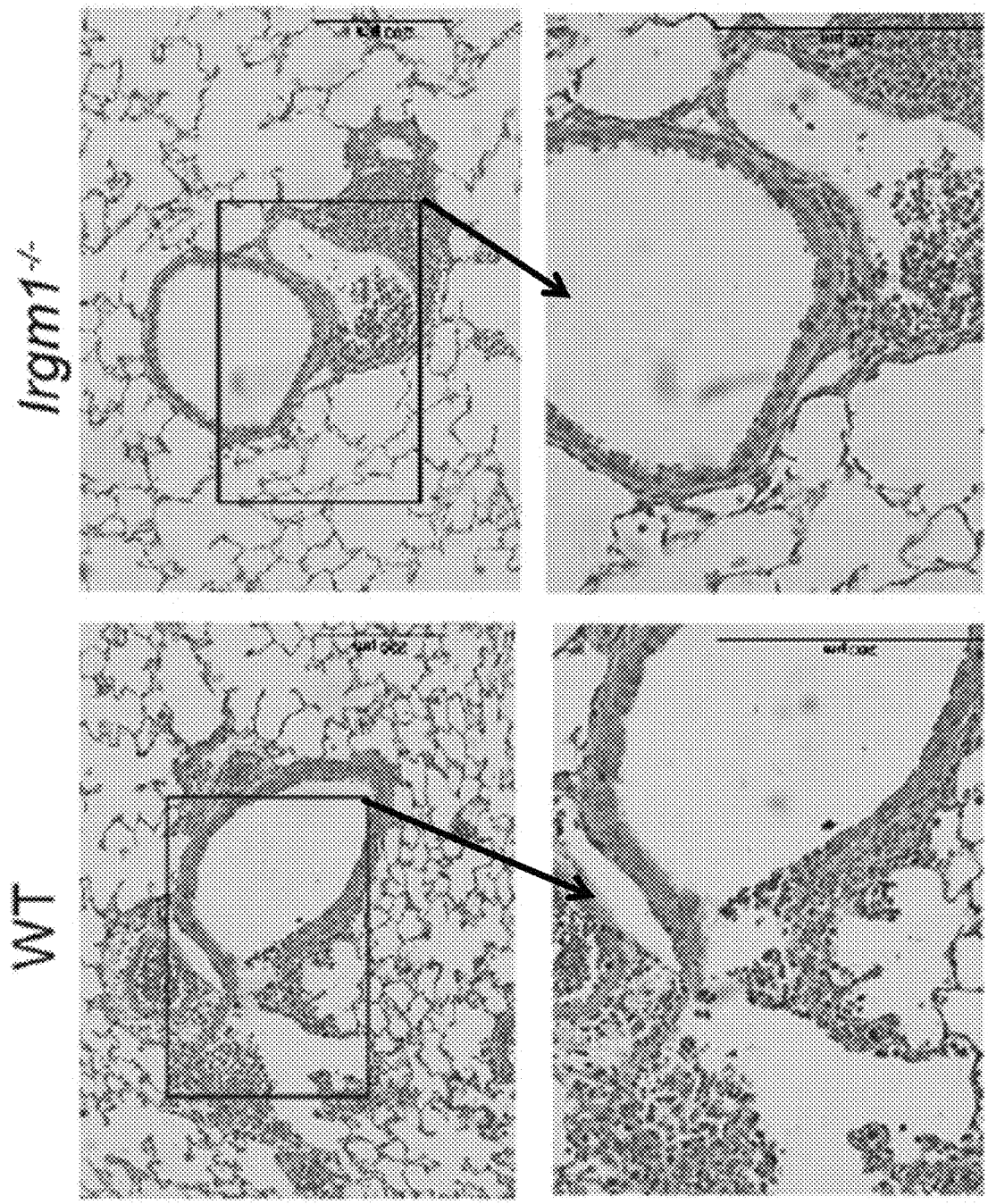
Figure 2L:
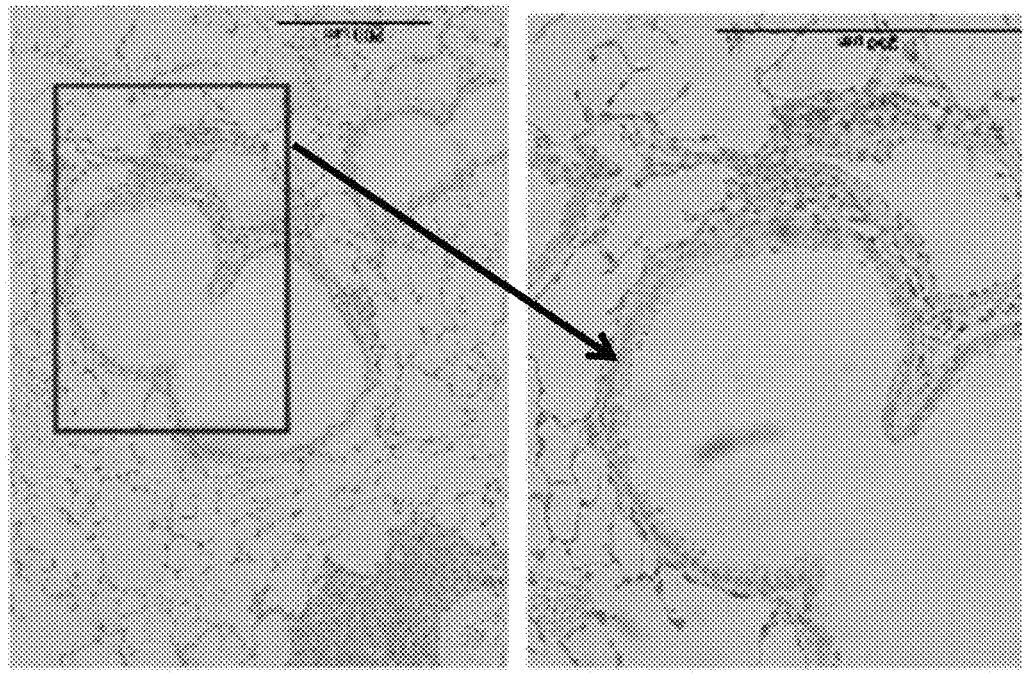
Figure 2L:
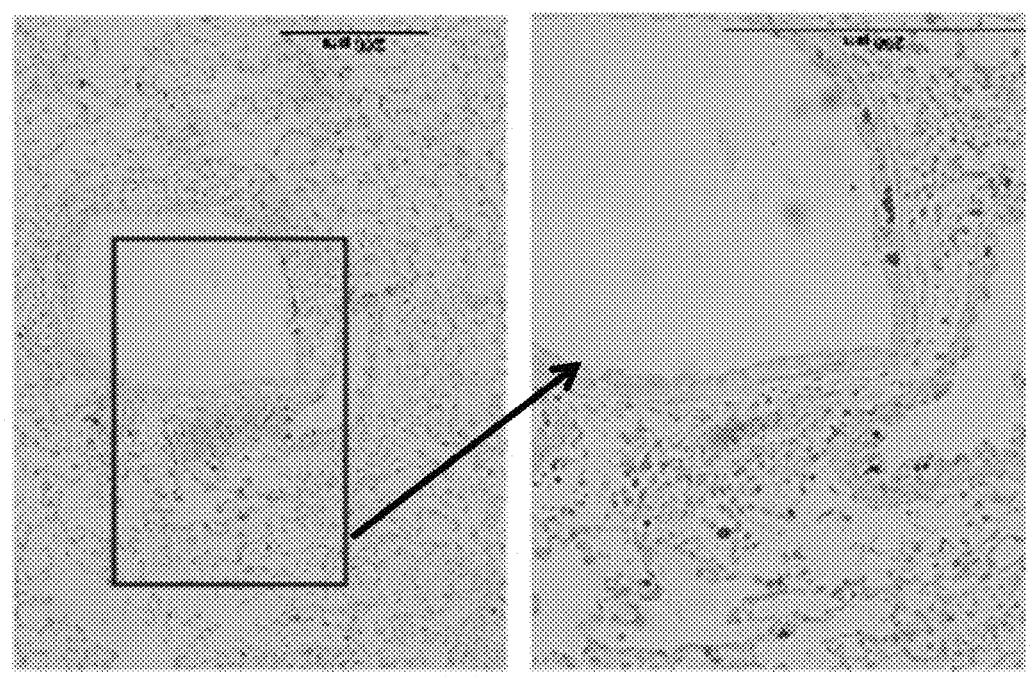
Figure 2M:
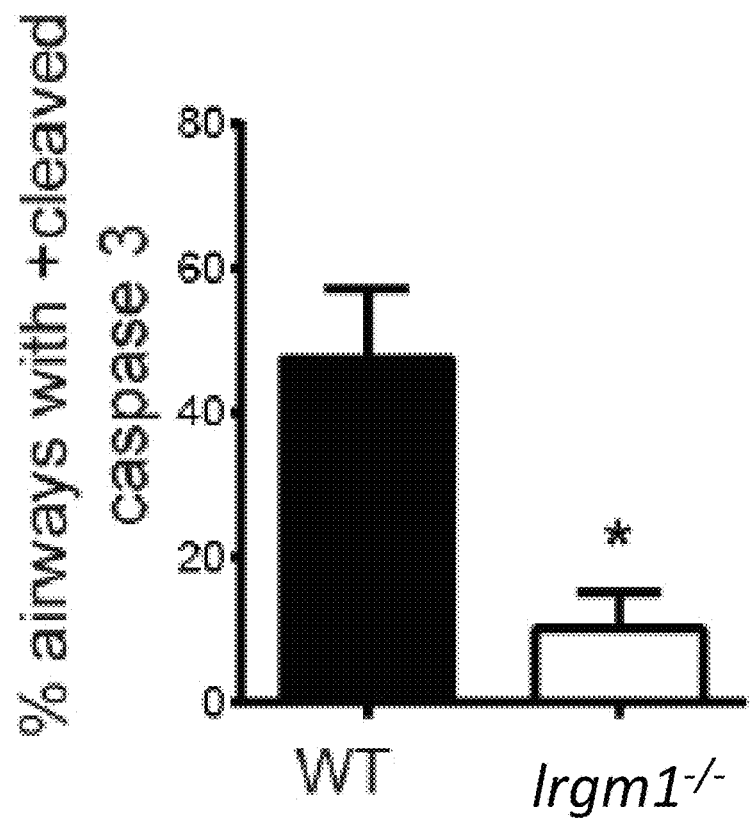
Figure 2N:
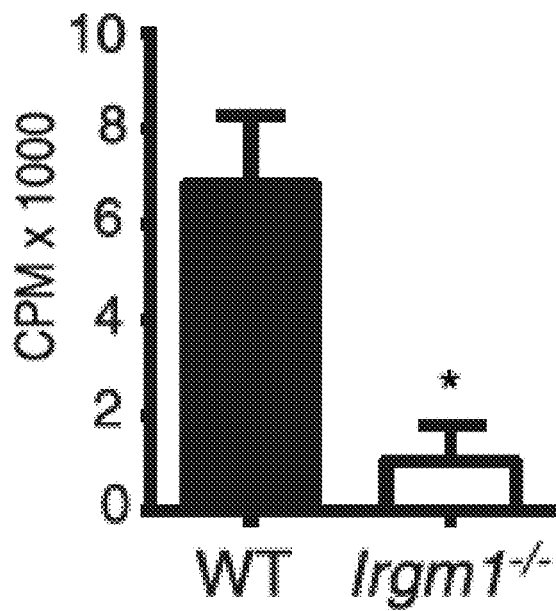
Figure 2O:
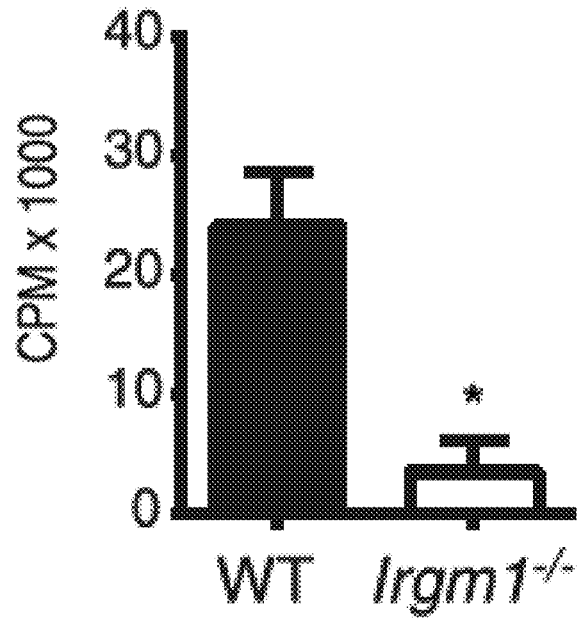
Figure 2P:
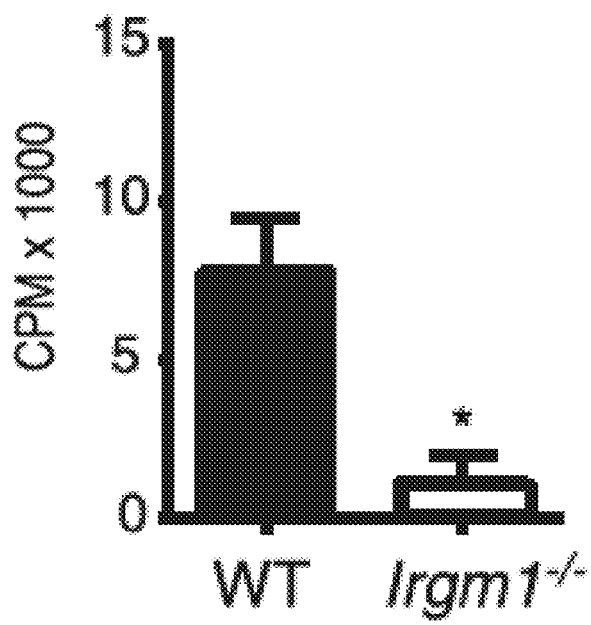
Figure 2Q:
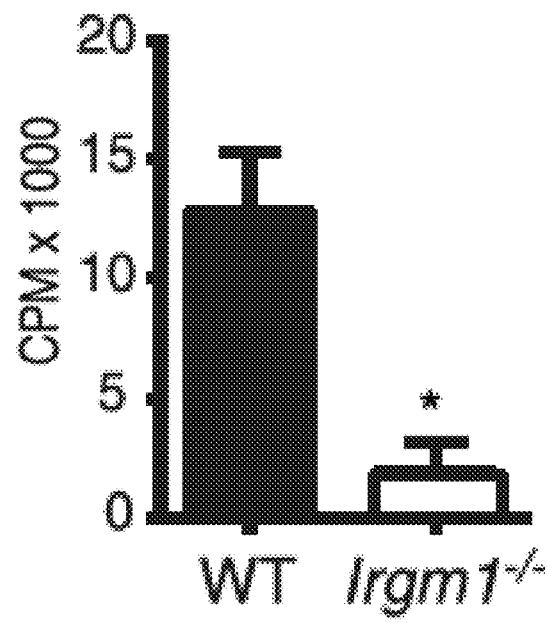
Figure 2R:
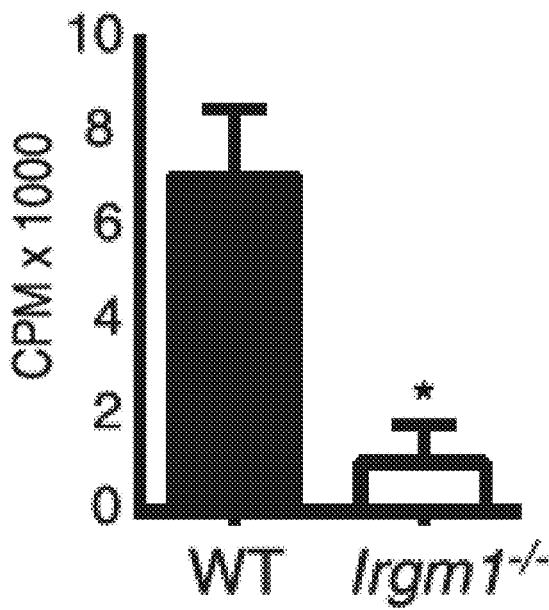
Figure 2S:
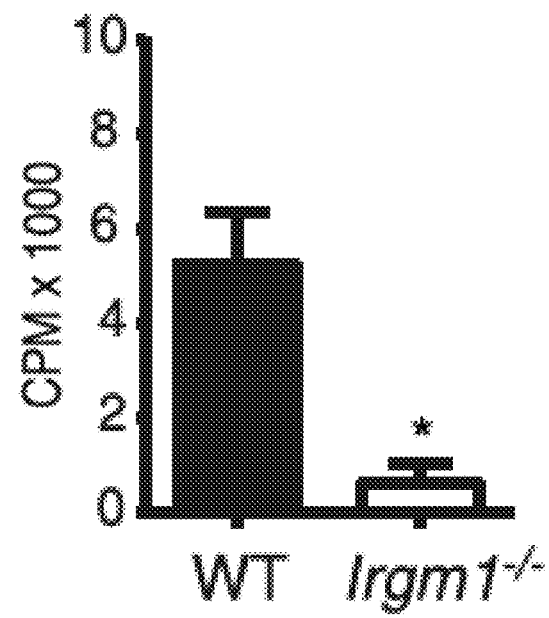
Figure 2T:
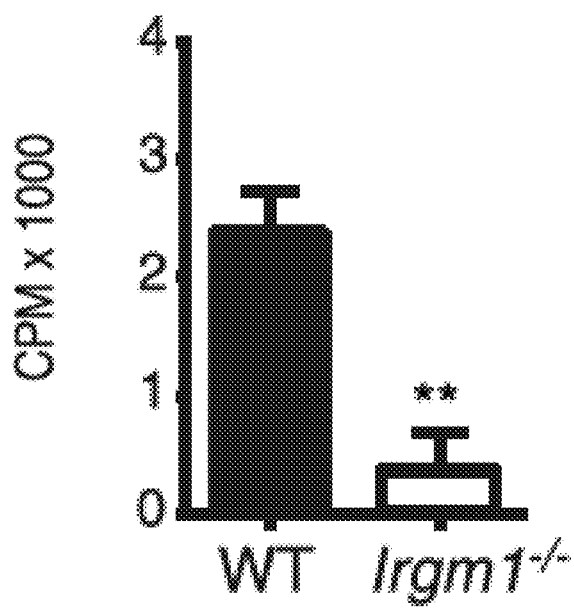
Figure 2U:
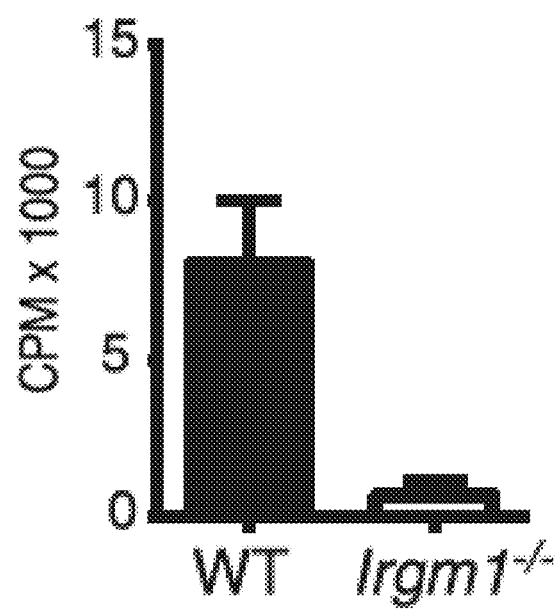

It was hypothesized that if innate immunity was critical for the protection of Irgm1$^{-/-}$ mice, then a decrease in inflammatory response to Influenza infection would be observed. Indeed, infected Irgm1$^{-/-}$ mice displayed reduced tissue levels of cytokines and chemokines previously associated with severe influenza in humans including TNFα (FIG. 2F), MIP-1 (FIG. 2G), IL-10 (FIG. 2H), MCP-1 (FIG. 2I), and IL-1Rα (FIG. 2J). Analysis of RNA sequencing of whole lung tissue showed that infected controls demonstrated enhanced enrichment scores for pathways associated with pro-inflammatory innate immune responses and cell death compared to infected Irgm1$^{-/-}$ mice (Table 2). Histopathological analysis confirmed greater airway epithelial damage, inflammation, and cell death in control lungs (FIG. 2K, FIG. 2L, FIG. 19A, and FIG. 19B). Quantification of the percentage of airways containing apoptotic epithelial cells, a known mechanism of cell death during Influenza infection, showed greater numbers in control mice (FIG. 2M). Collectively, these data suggest that Irgm1 deficiency mediates protection from Influenza infection by suppressing host pro-inflammatory innate immune responses and reducing collateral tissue injury.

Figure 3A:
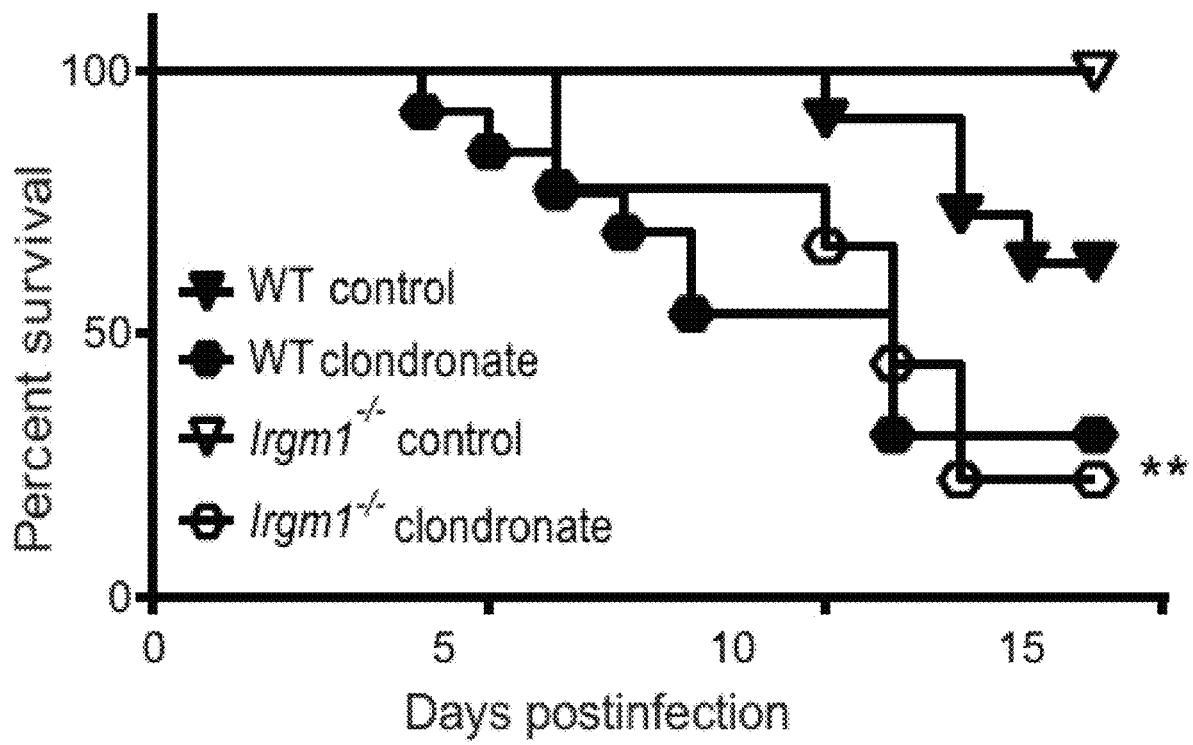
FIG. 3A, FIG. 3B, FIG. 3C, and FIG. 3D depicts graphs showing that Irgm1$^{-/-}$ macrophages are crucial for the protection.
Figure 9:
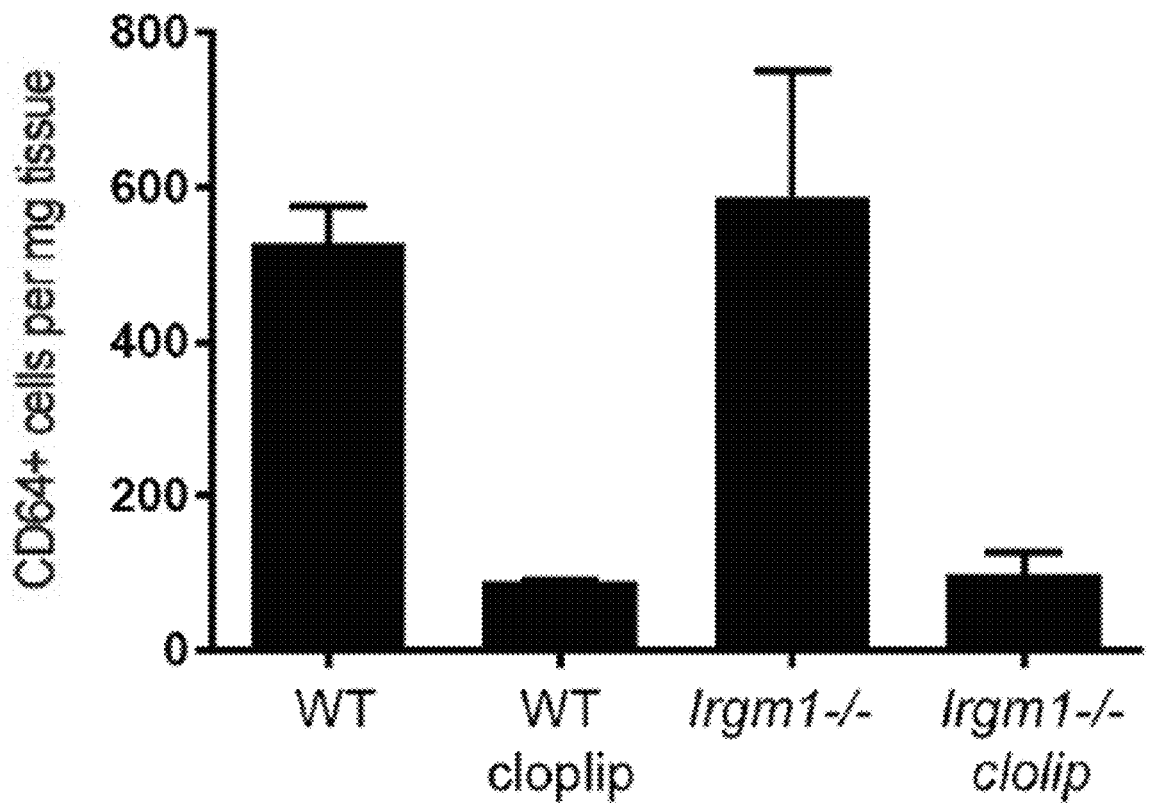
FIG. 9 depicts a graph showing that clondronate depletes macrophages in infected Irgm1$^{-/-}$ and littermate control mice. Quantification by flow cytometry of lung macrophages from littermate control and Irgm1$^{-/-}$ mice injected intraperitoneally with control liposomes or clodronate liposomes 2 days prior to infection, infected with 5,000 pfu of WSN, injected again with control liposomes or clodronate liposomes on days 0 and postinfection, and sacrificed for analysis on day 5 postinfection. Lung cells were analyzed by including live cells by forward/side scatter properties, doublets excluded, immune cells included by CD45+ staining, B-cells excluded by CD19+ staining, and gating on the macrophage population by CD64+ staining. n=3-4 mice per group from 2 independent experiments. Similar results were seen on day 7 postinfection.

Within the lung, macrophages have been implicated as essential mediators of innate immune responses to bacterial and viral pathogens. To determine whether Irgm1 mediates protection from Influenza infection through a macrophage dependent mechanism, macrophages were depleted using clodronate liposomes in infected control and Irgm1$^{-/-}$ mice (FIG. 9). Consistent with our prior observations, Kaplan-Meier survival analysis revealed that non-macrophage-depleted Irgm1$^{-/-}$ mice displayed marked reductions in mortality compared to wild type mice that also received control liposomes (FIG. 3A). In contrast, wild type and Irgm1$^{-/-}$ mice that received liposomal clodronate displayed indistinguishably high mortality rates. These findings indicate that macrophages are required for protection from Influenza infection.

Figure 3B:
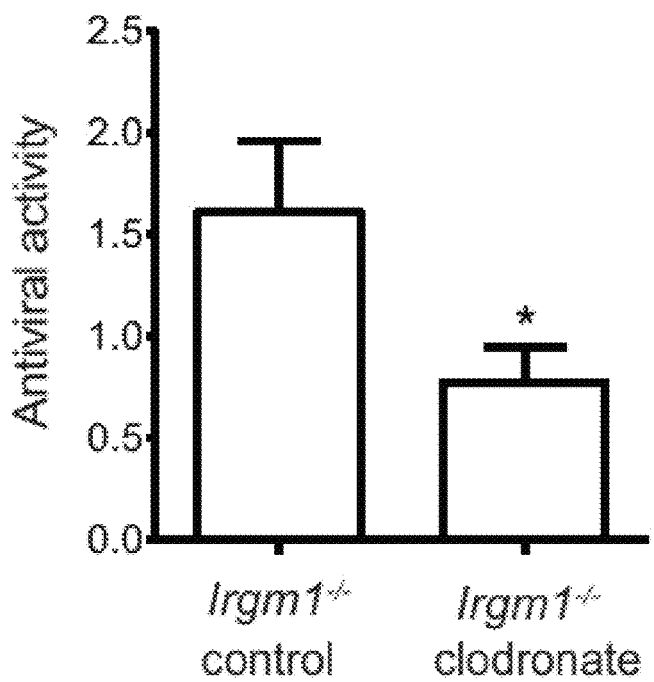
Figure 3C:
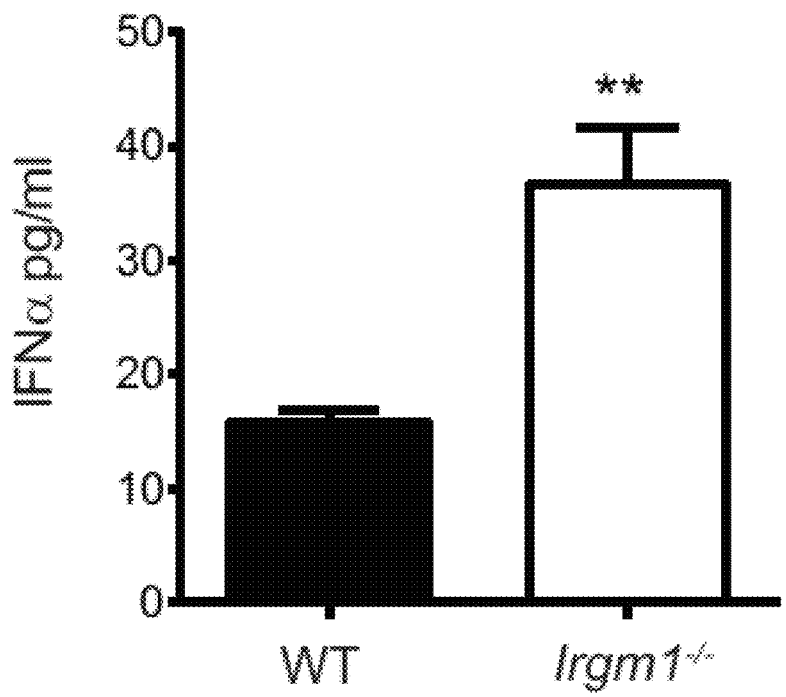
Figure 3D:
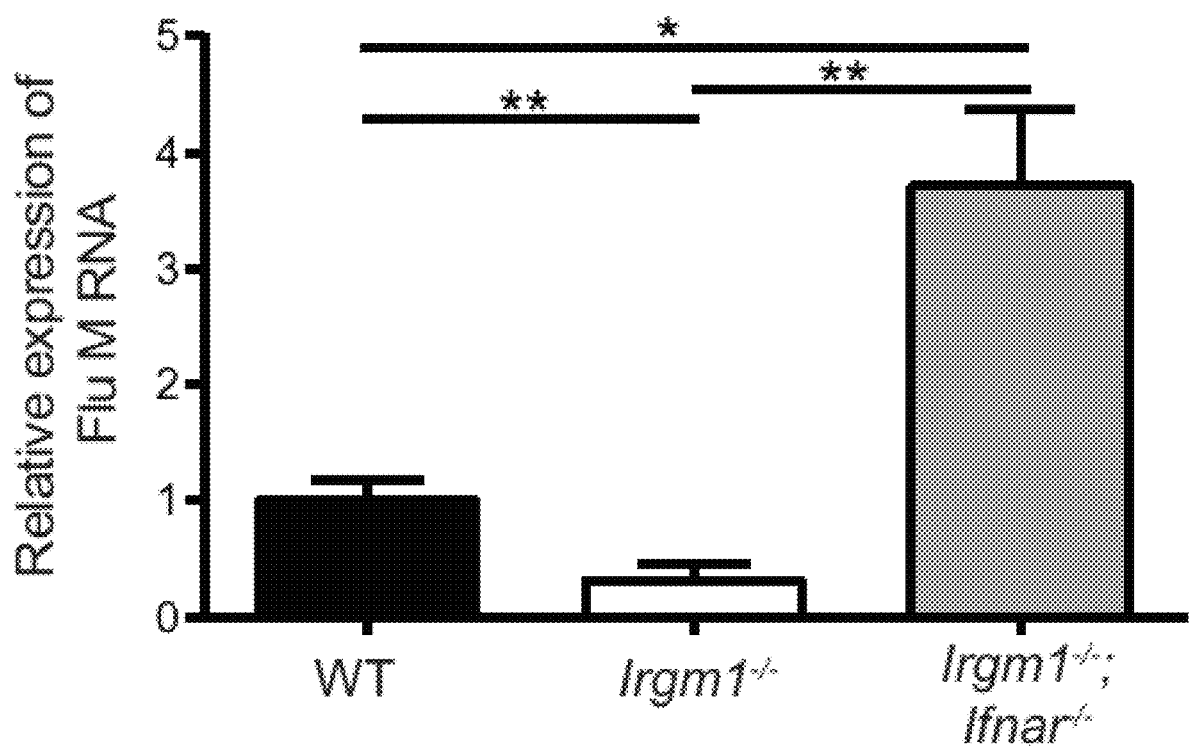

This approach also established that macrophages were the source of type I IFN as uninfected, macrophage-depleted Irgm1 mice demonstrated reductions in type I IFN activity (FIG. 3B). Consistent with this conclusion, bone marrow derived macrophages derived from Irgm1$^{-/-}$ mice produced increased levels of IFNα compared to bone marrow derived macrophages derived from control mice following in vitro Influenza infection (FIG. 3C). Importantly, bone marrow derived macrophages from Irgm1$^{-/-}$ mice had decreased Influenza RNA as compared to cells derived from controls, a finding dependent on Type I IFN signaling (FIG. 3D). This finding underlies a host difference in abortive infection as infectious virus was not recovered from any cell culture conditions. Taken together, the findings in Irgm1$^{-/-}$ mice demonstrate that type I IFNs protect from Influenza through actions on macrophages.

Given that the above findings are in a genetically altered model, it was next sought if there were more general elements within the environment, including the microbiome, that could drive this phenotype. There is emerging evidence that the microbiome can regulate host immune responses including type I IFN signaling.[13] The microbiome also controls the response to Influenza as multiple studies have documented that disruption of the microbiome through either antibiotic therapy or production of germ-free animals results in worsened outcomes following Influenza infection.[14-16] Therefore, it was hypothesized that the microbiome protects from Influenza infection through augmentation of type I IFN signaling.

Figure 4A:
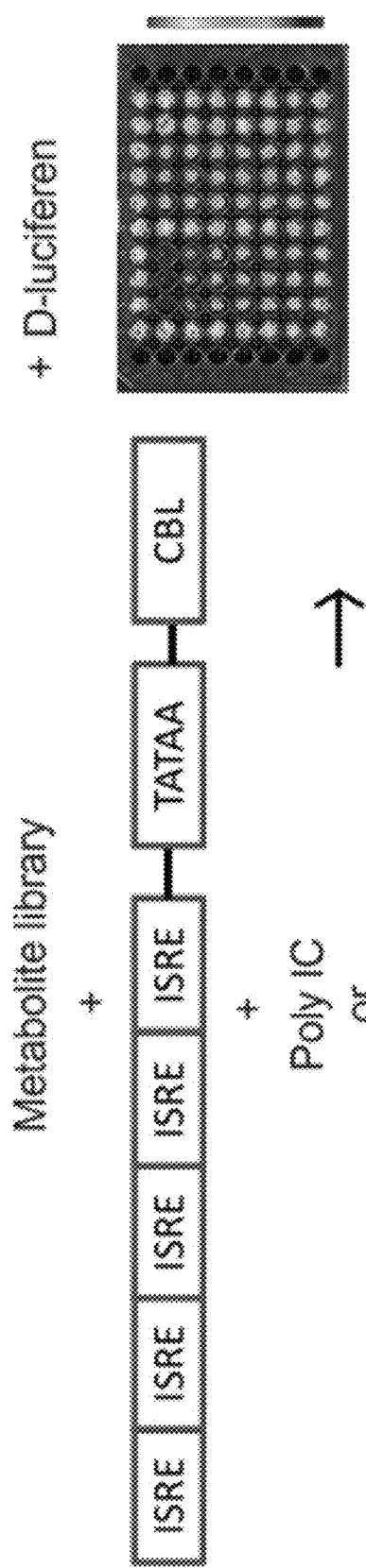
Figure 4B:
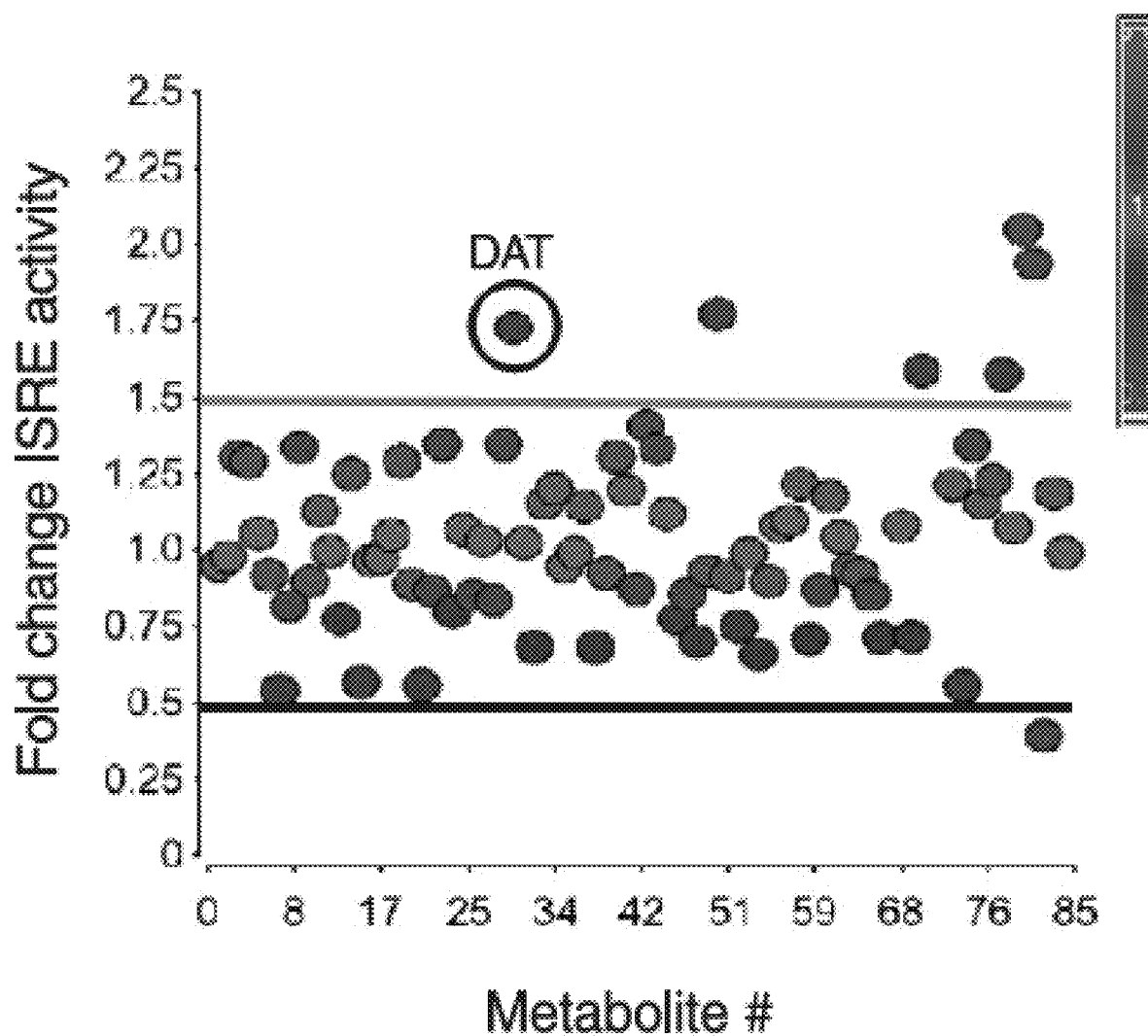
Figure 4C:
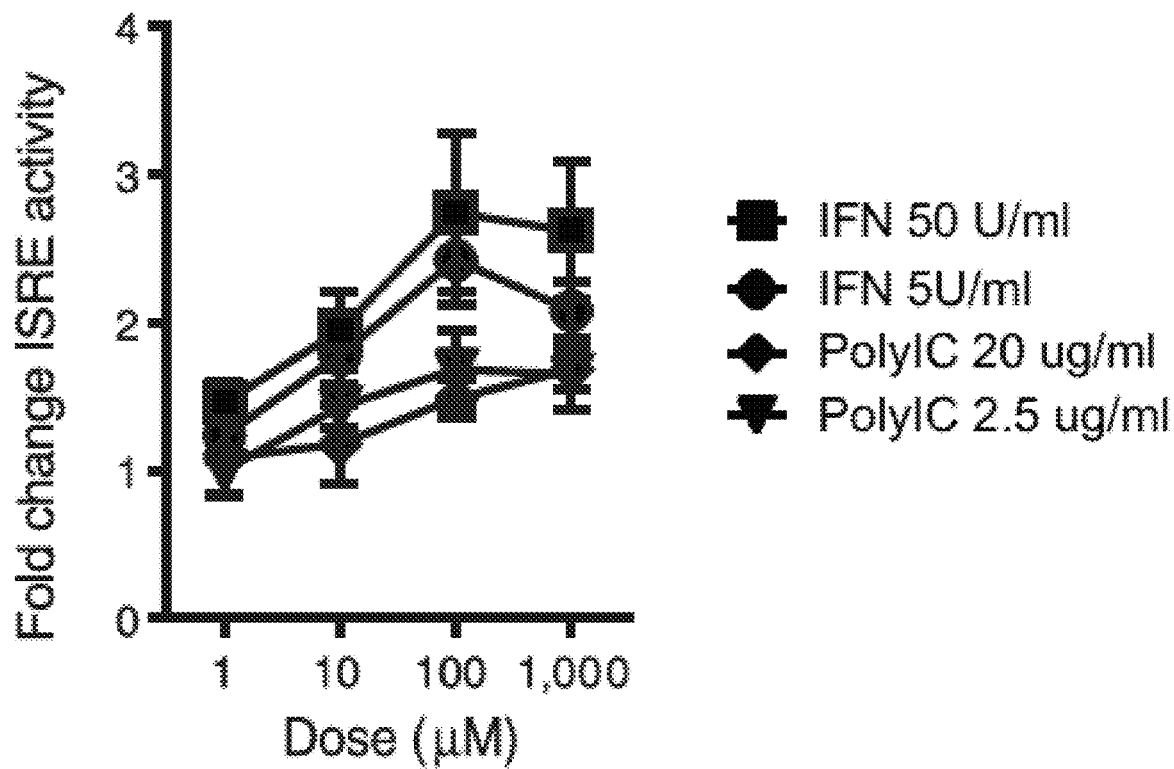
Figure 10:
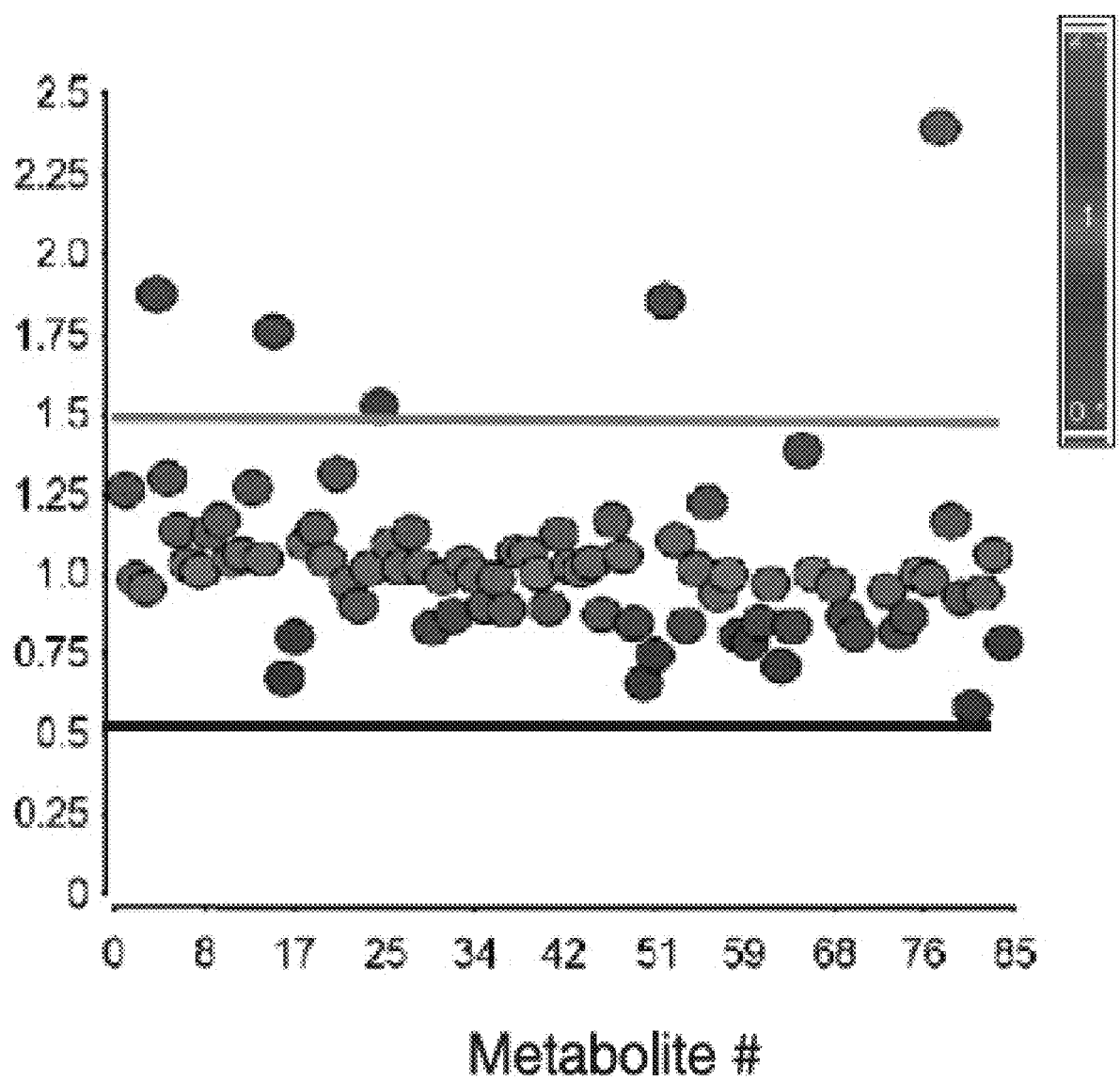
FIG. 10 depicts a scatter plot displaying fold-change in luminescence for 100 μM metabolite screen with 10 U/ml Type I IFN treatment. n=2/metabolite.
Figure 11A:
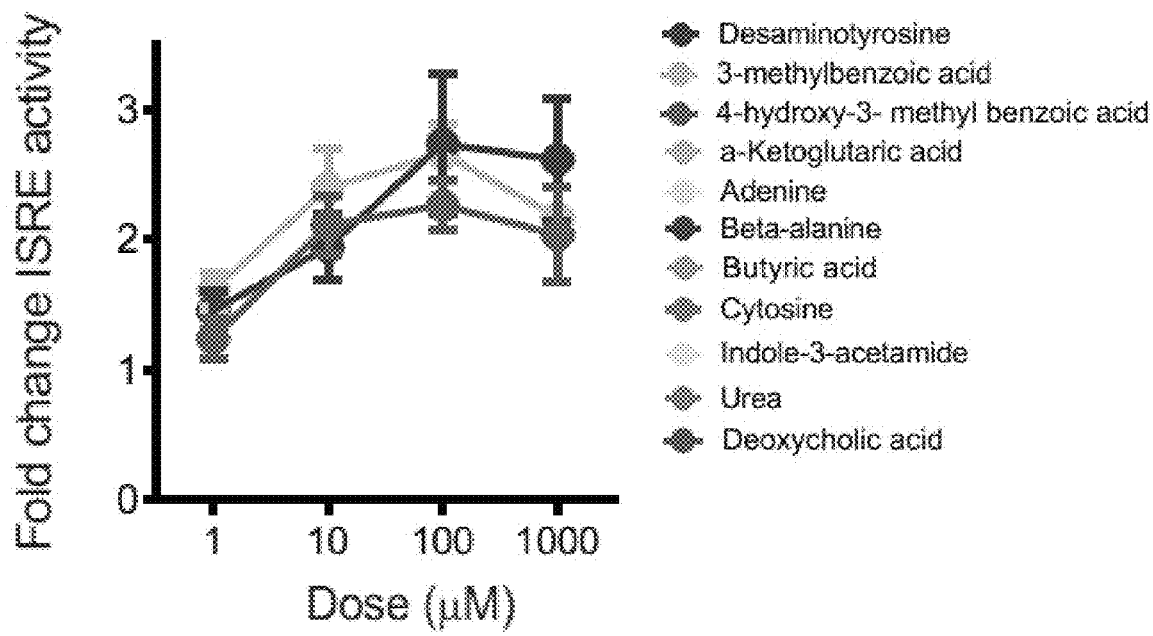
FIG. 11A, FIG. 11B, FIG. 11C, FIG. 11D, FIG. 11E, FIG. 11F, FIG. 11G, FIG. 11H, FIG. 11I, FIG. 11J, FIG. 11K, and FIG. 11L depict graphs showing the fold increase in luminescence for selected metabolites at indicated doses with Type I IFN and polyIC. n=3-4 independent experiments.
Figure 11B:
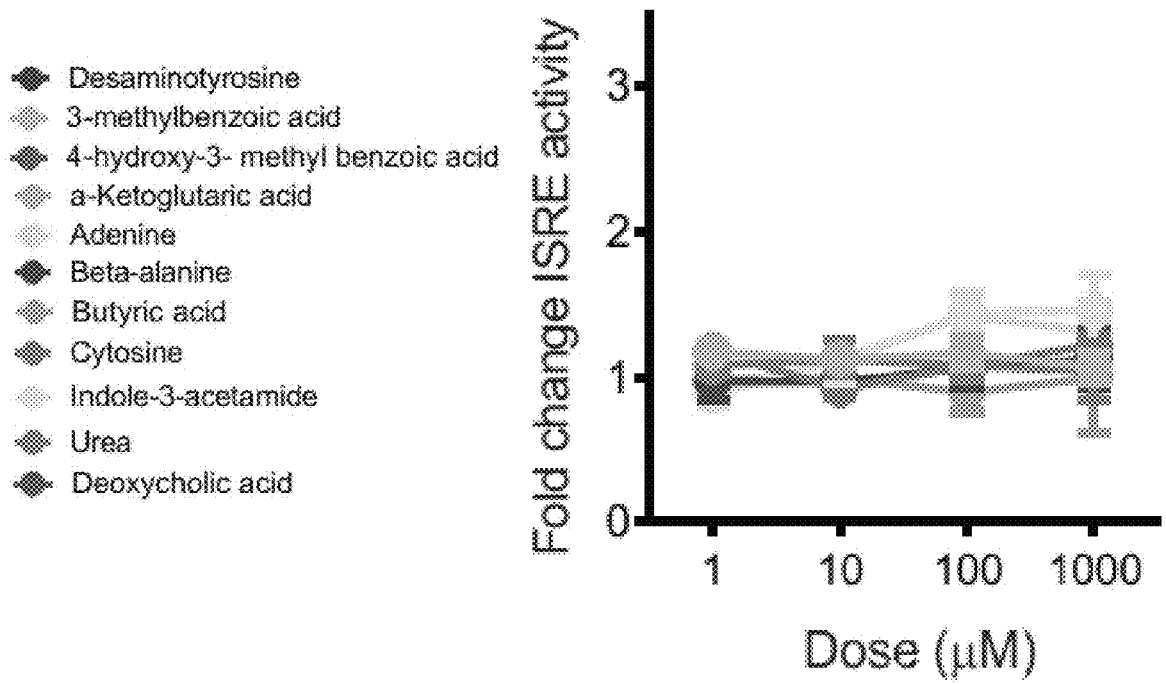
Figure 11C:
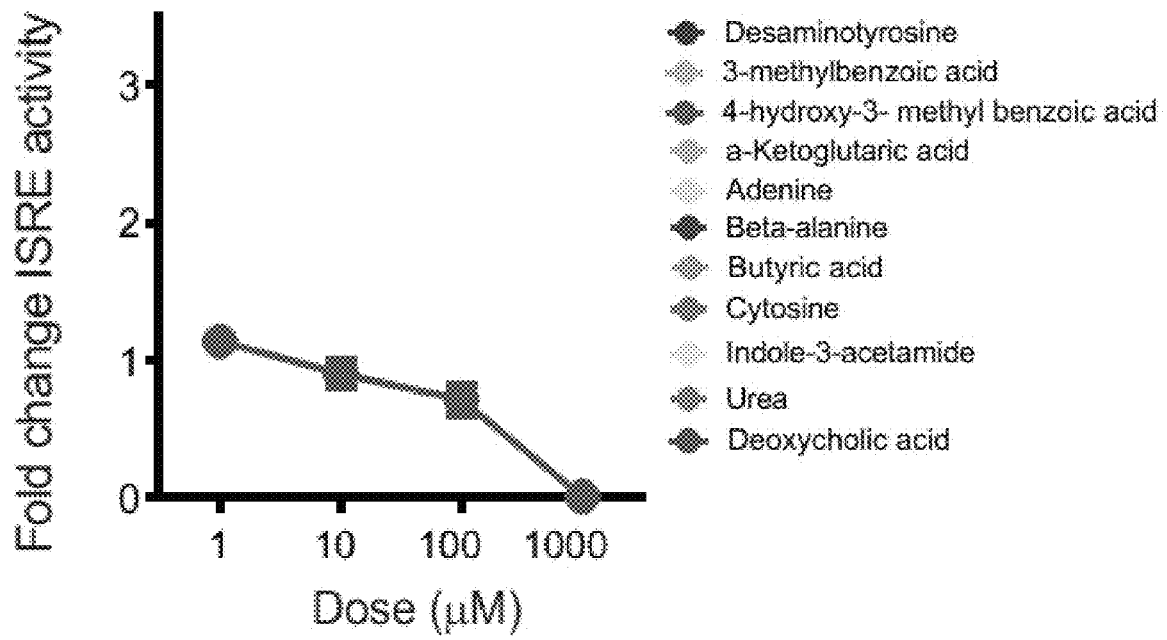
Figure 11D:
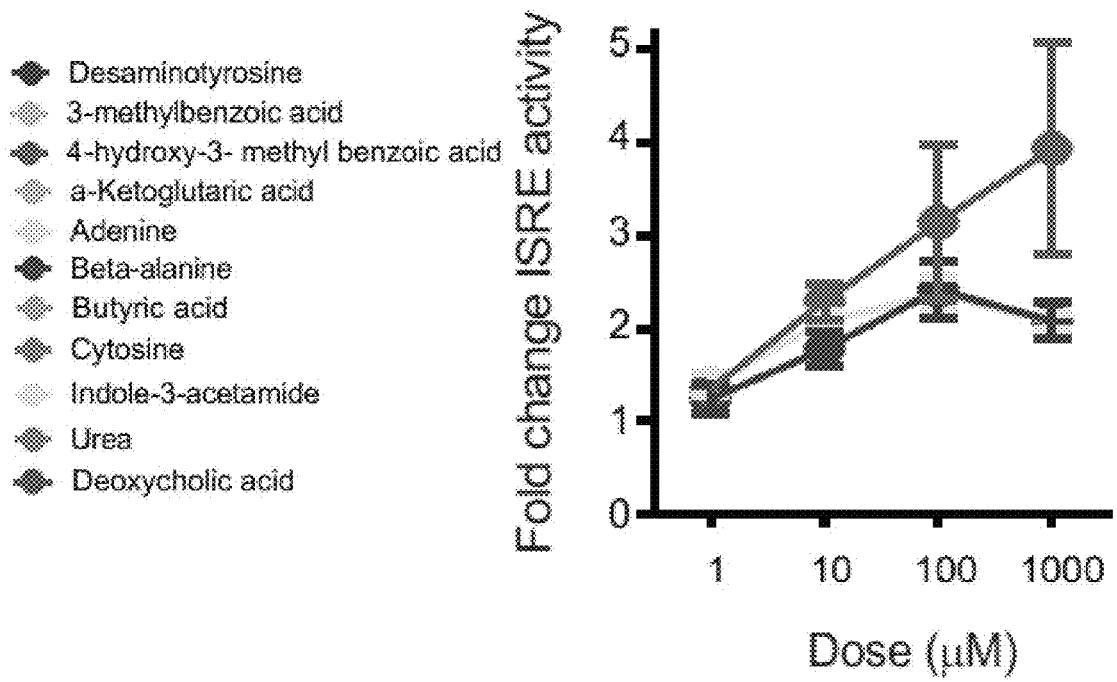
Figure 11E:
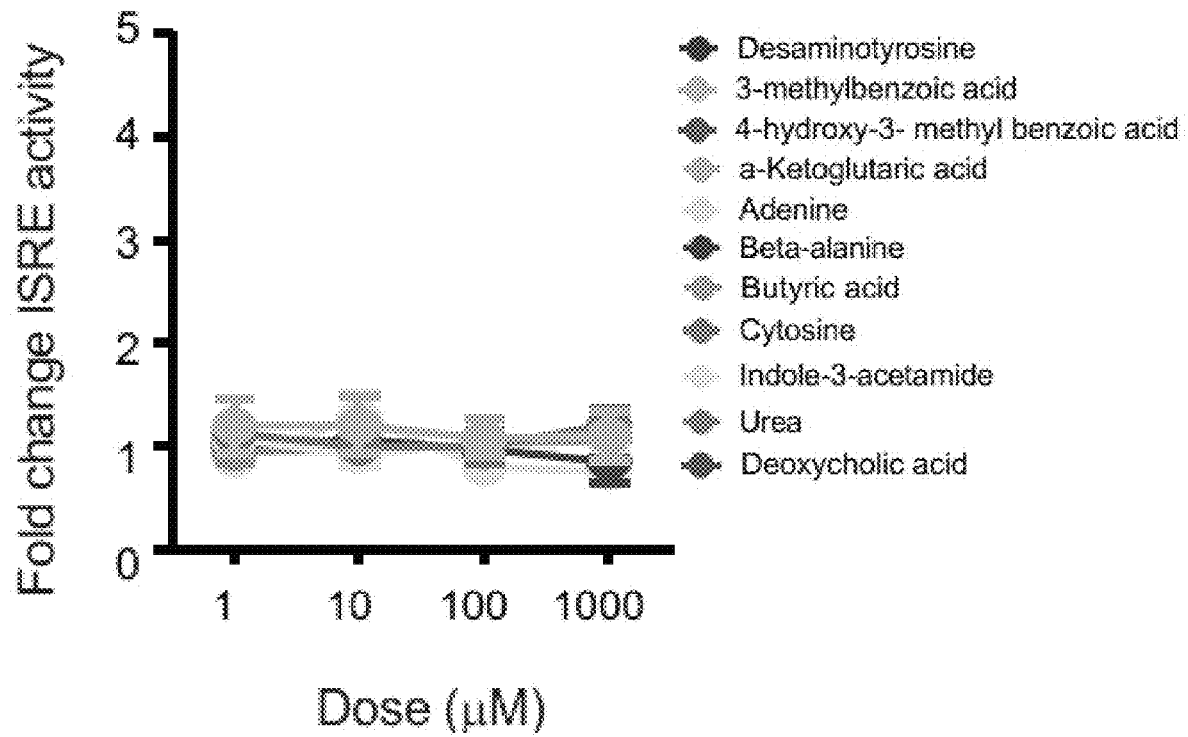
Figure 11F:
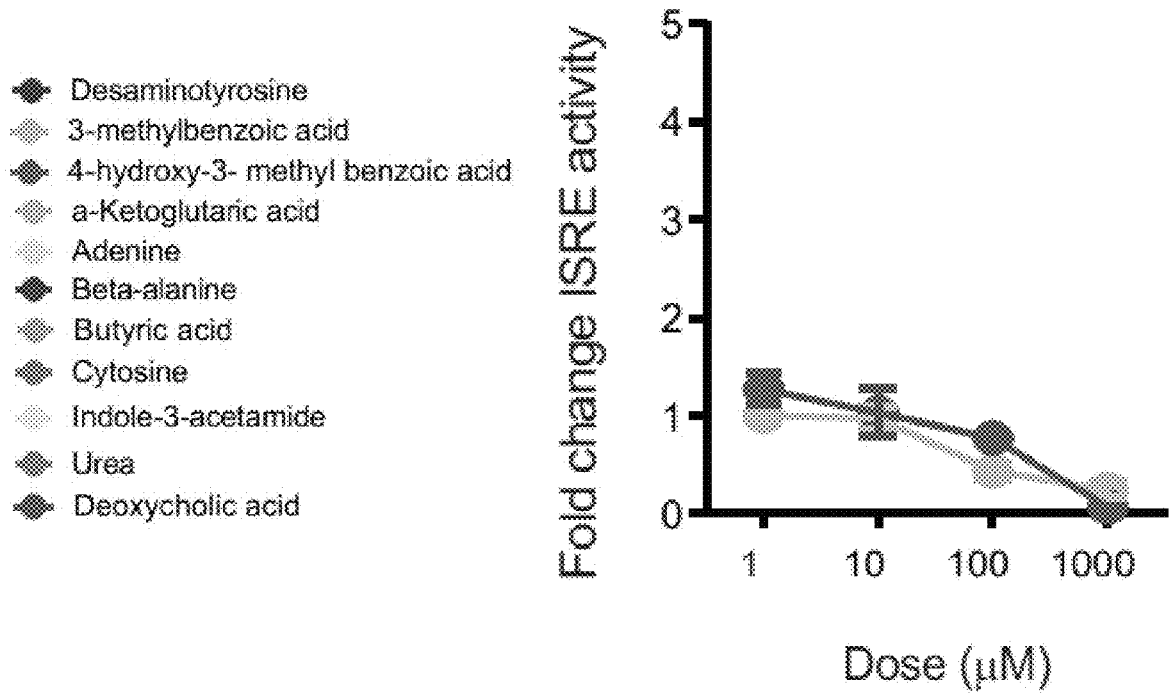
Figure 11G:
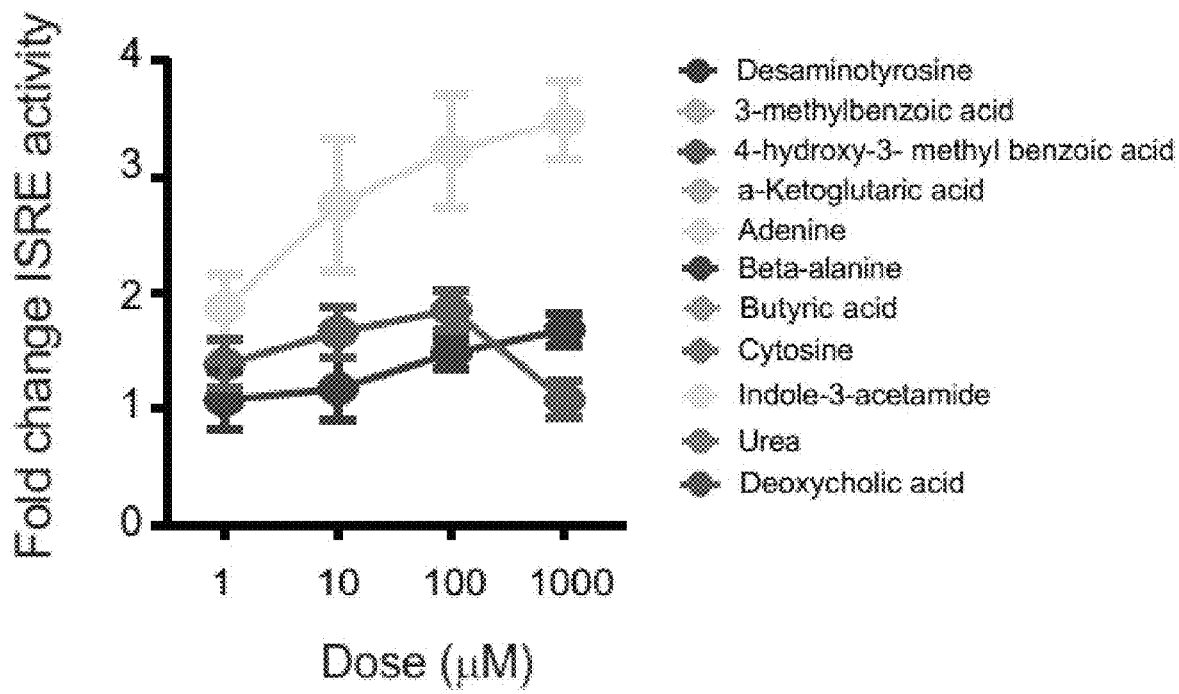
Figure 11H:
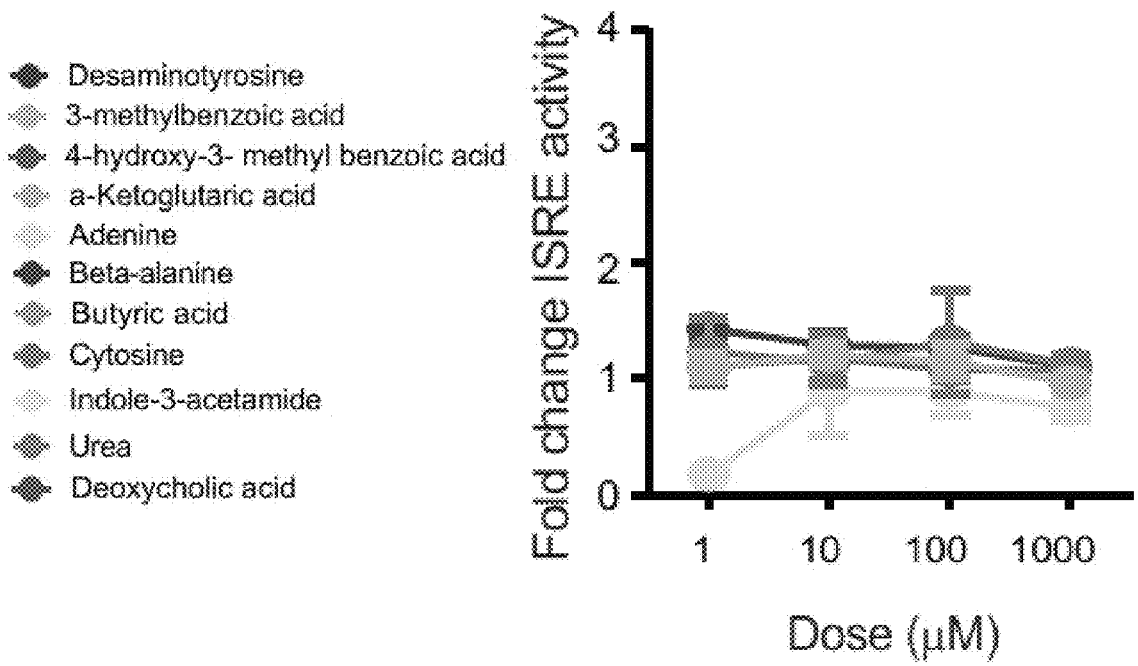
Figure 11I:
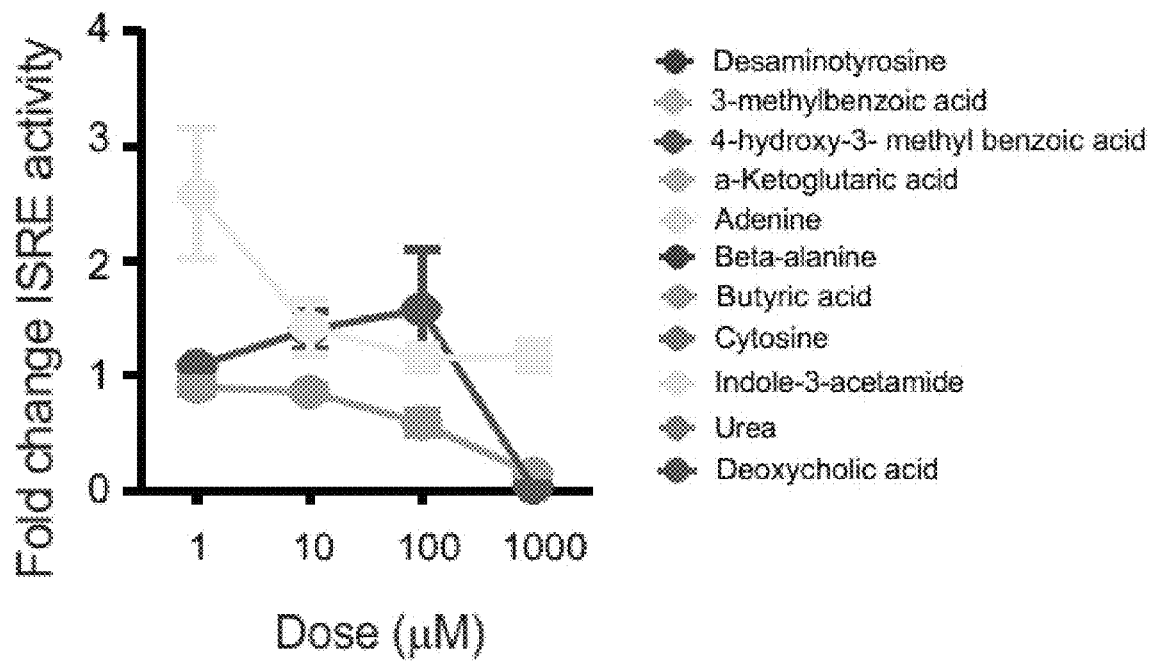
Figure 11J:
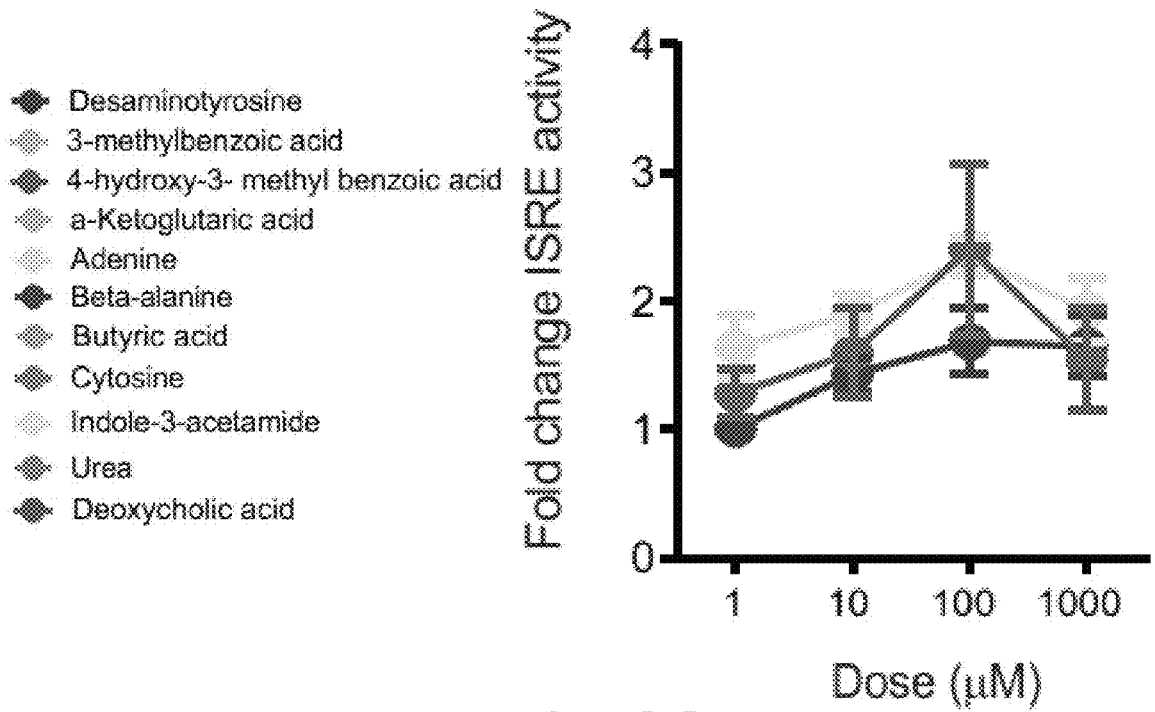
Figure 11K:
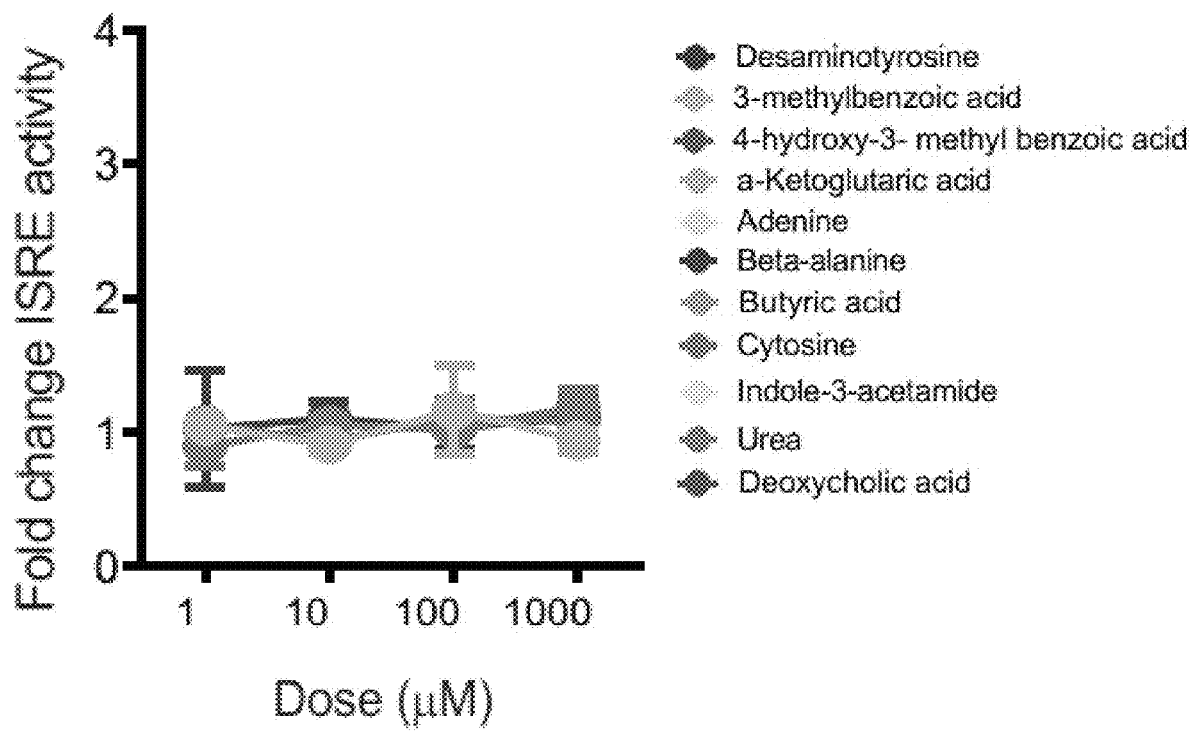
Figure 11L:
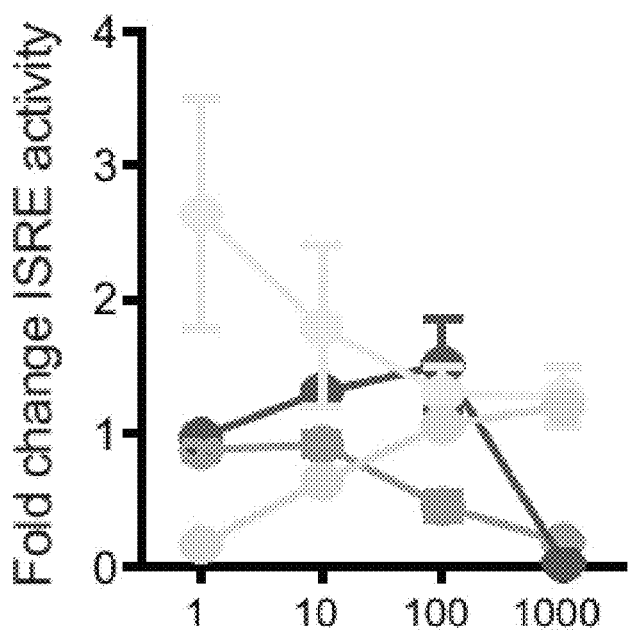

Microbial metabolites modulate a variety of important systemic phenotypes.[17-20] This emerging paradigm suggests the possibility that specific microbial metabolites mediate the protective effect of the microbiome. Therefore, a library of microbiome associated metabolites was screened for the ability to enhance type I IFN signaling.[21] A reported cell line that harbors multiple type I IFN response elements (ISREs) driving firefly luciferase was utilized.[22] Each metabolite was screened for the ability to enhance reporter activity in the background of type I IFN or polyIC (an inducer of type I IFN production) treatment (schematic FIG. 4A). Using this methodology, 11 metabolites were identified that increased reporter activity following polyIC co-stimulation (FIG. 4B) and 5 metabolites that increased ISRE reporter activity with type I IFN co-stimulation (FIG. 10). Among the metabolites subjected to secondary validation, desaminotyrosine enhanced type I IFN signaling in a dose-dependent manner following both type I IFN and polyIC co-treatment (FIG. 4C, FIG. 11A, FIG. 11B, FIG. 11C, FIG. 11D, FIG. 11E, FIG. 11F, FIG. 11G, FIG. 11H, FIG. 11I, FIG. 11J, FIG. 11K, and FIG. 11L).

Figure 4D:
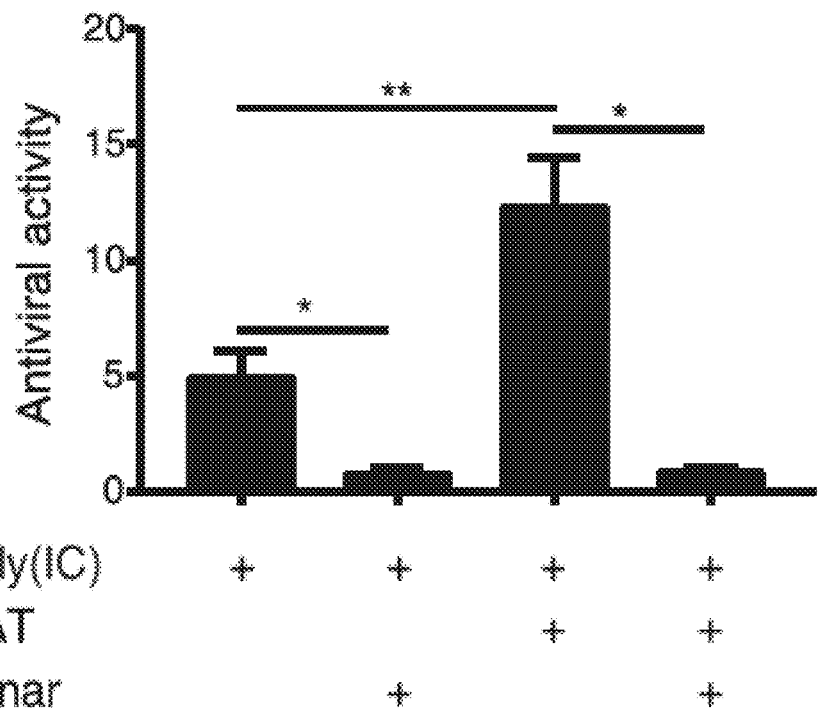
Figure 4E:
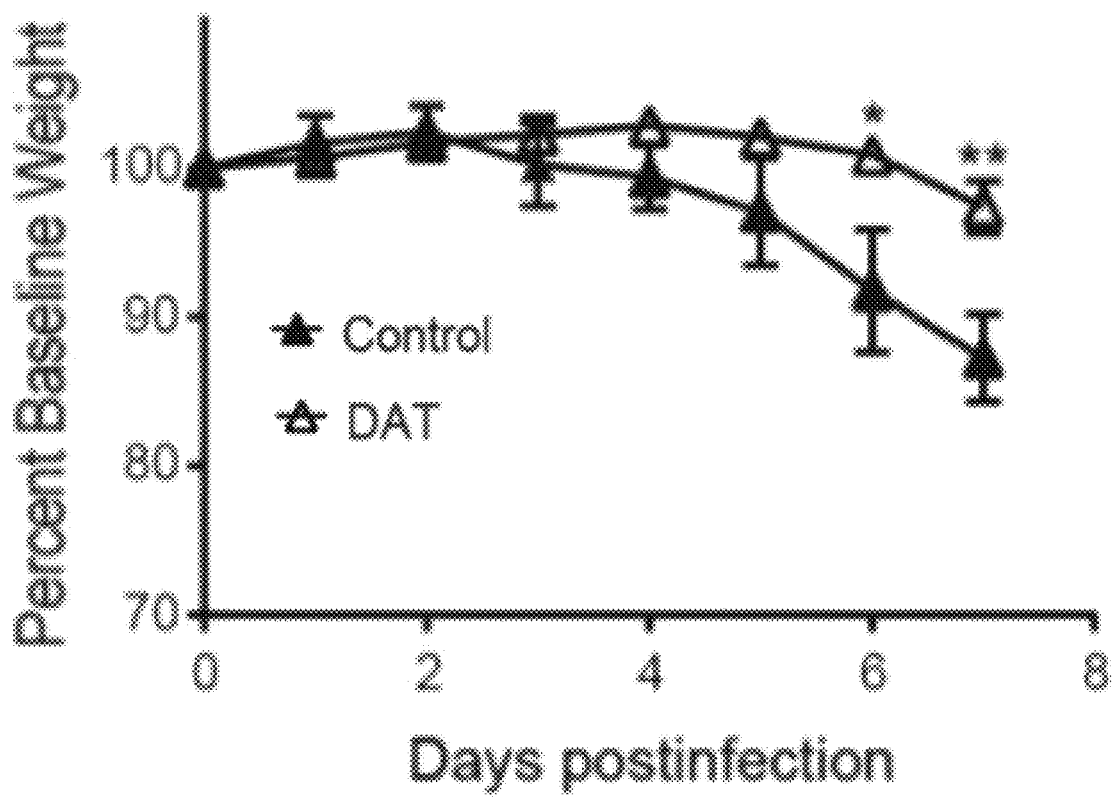
Figure 4F:
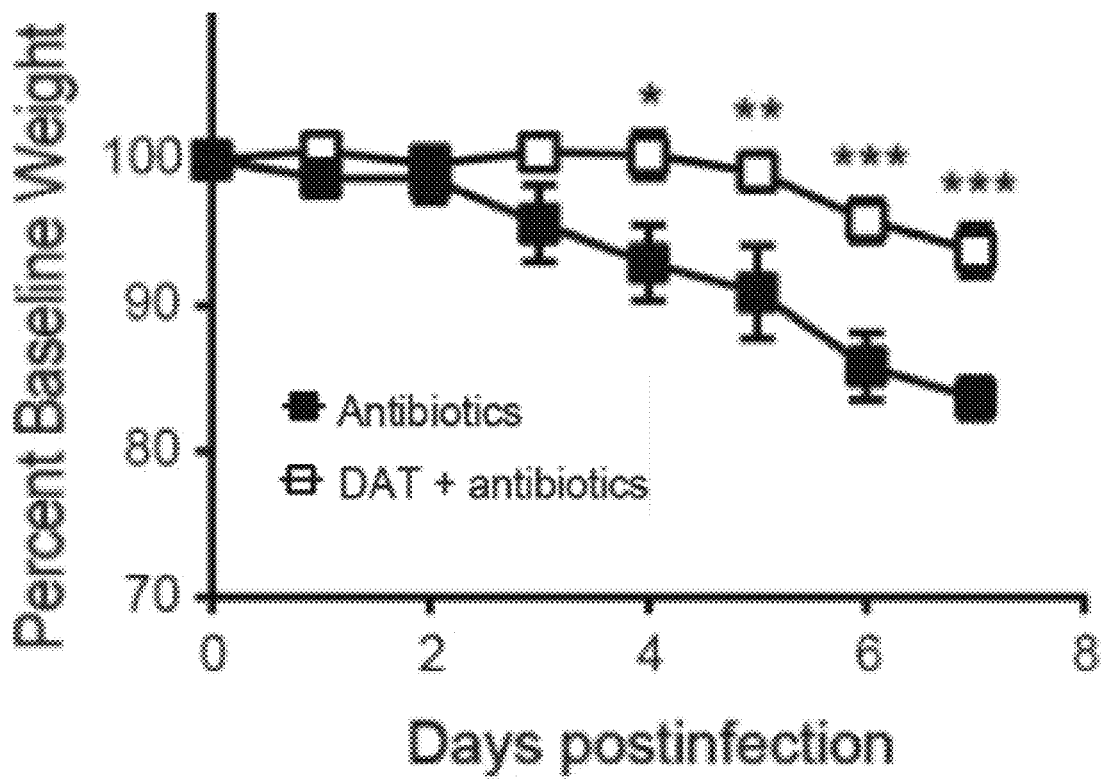
Figure 4G:
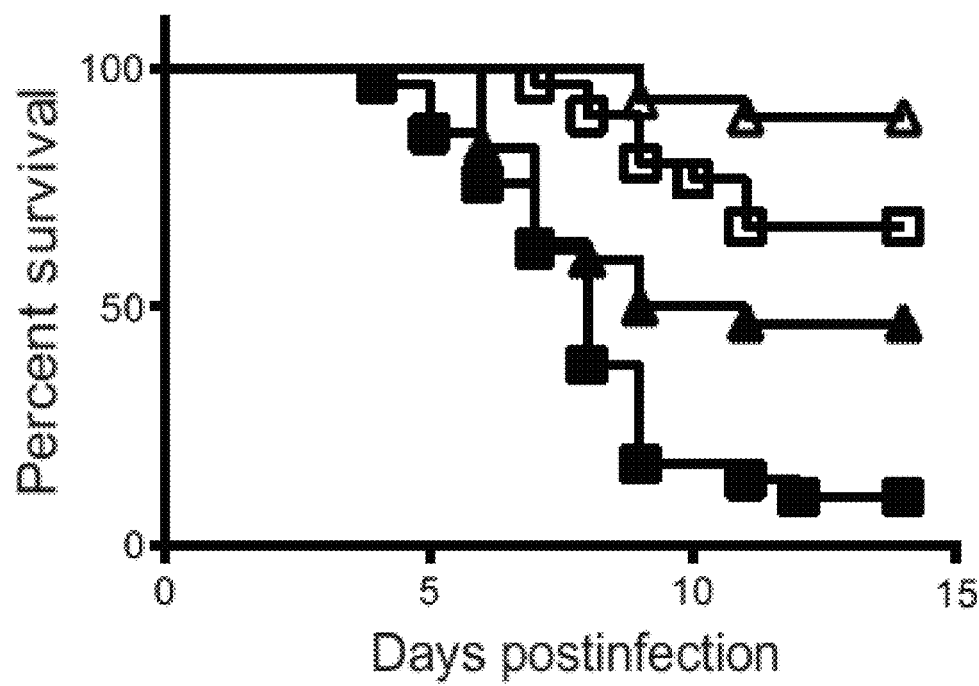
Figure 4H:
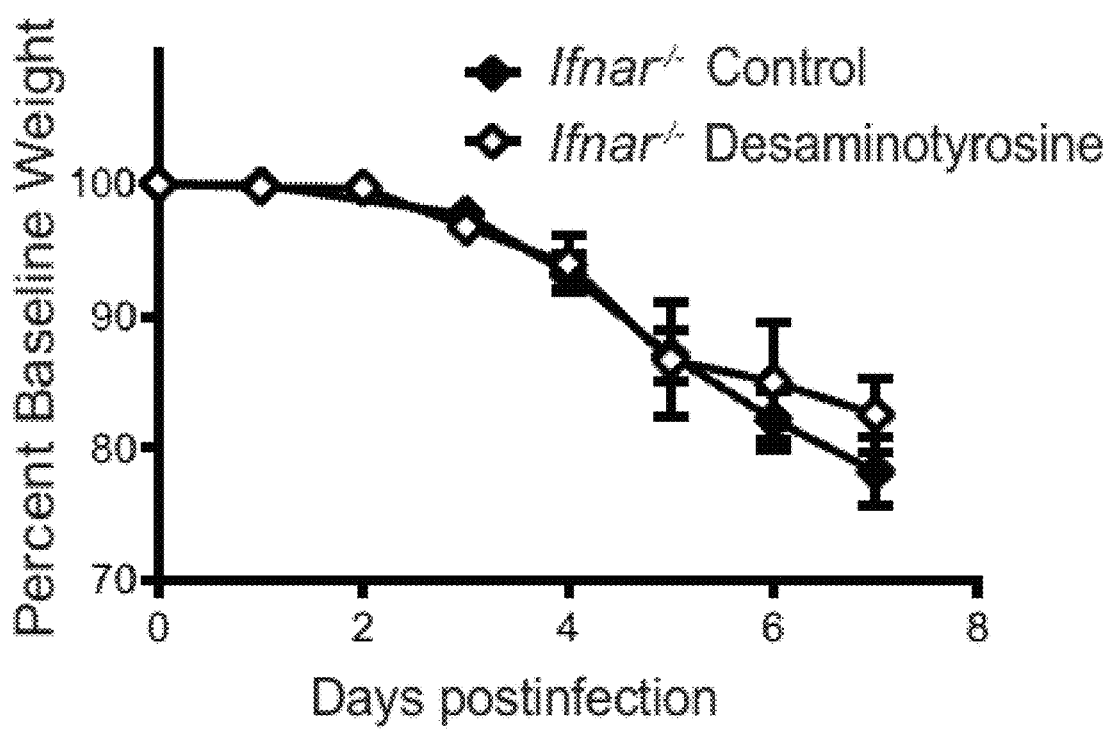
Figure 4I:
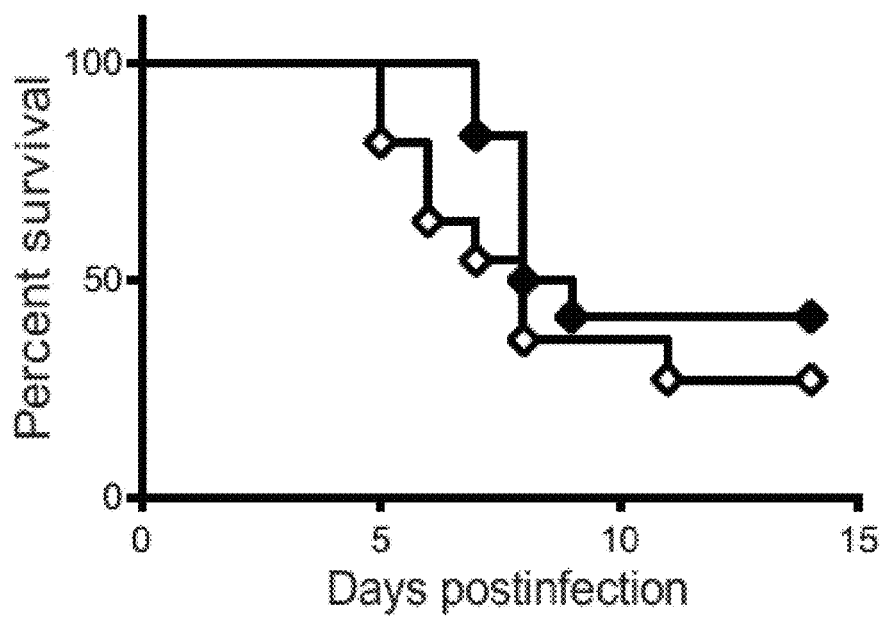
Figure 4J:
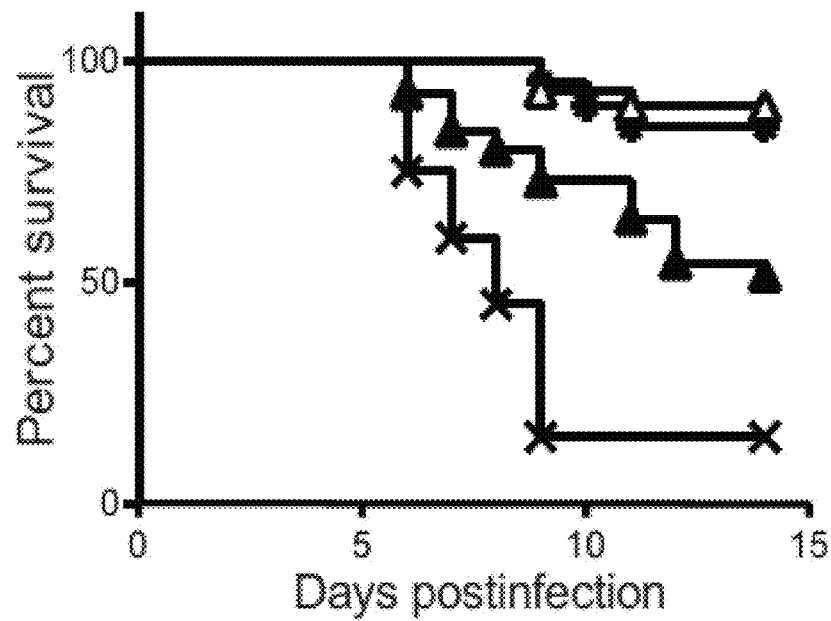
Figure 4N:
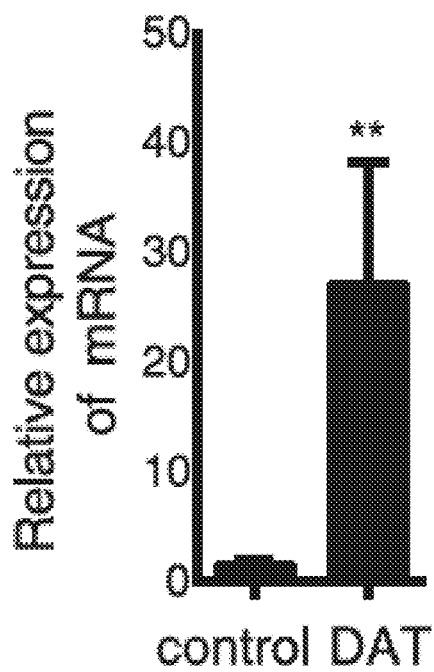
Figure 4O:
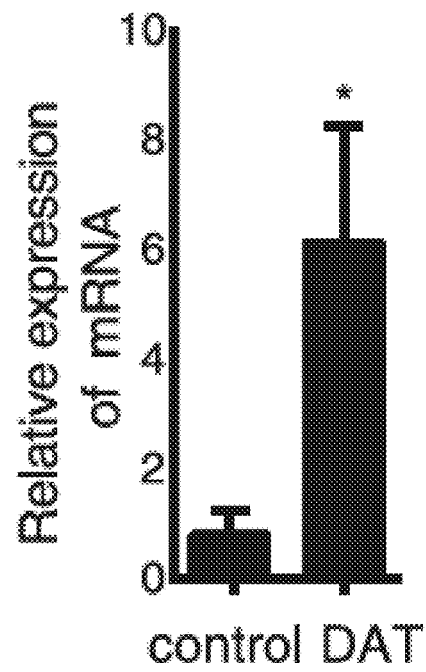
Figure 4P:
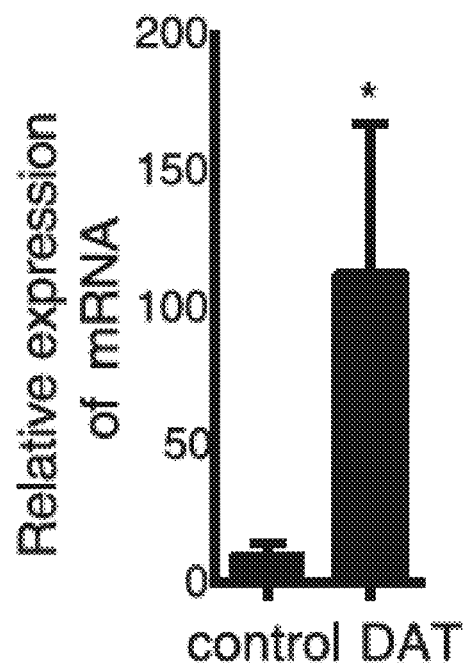
Figure 12:
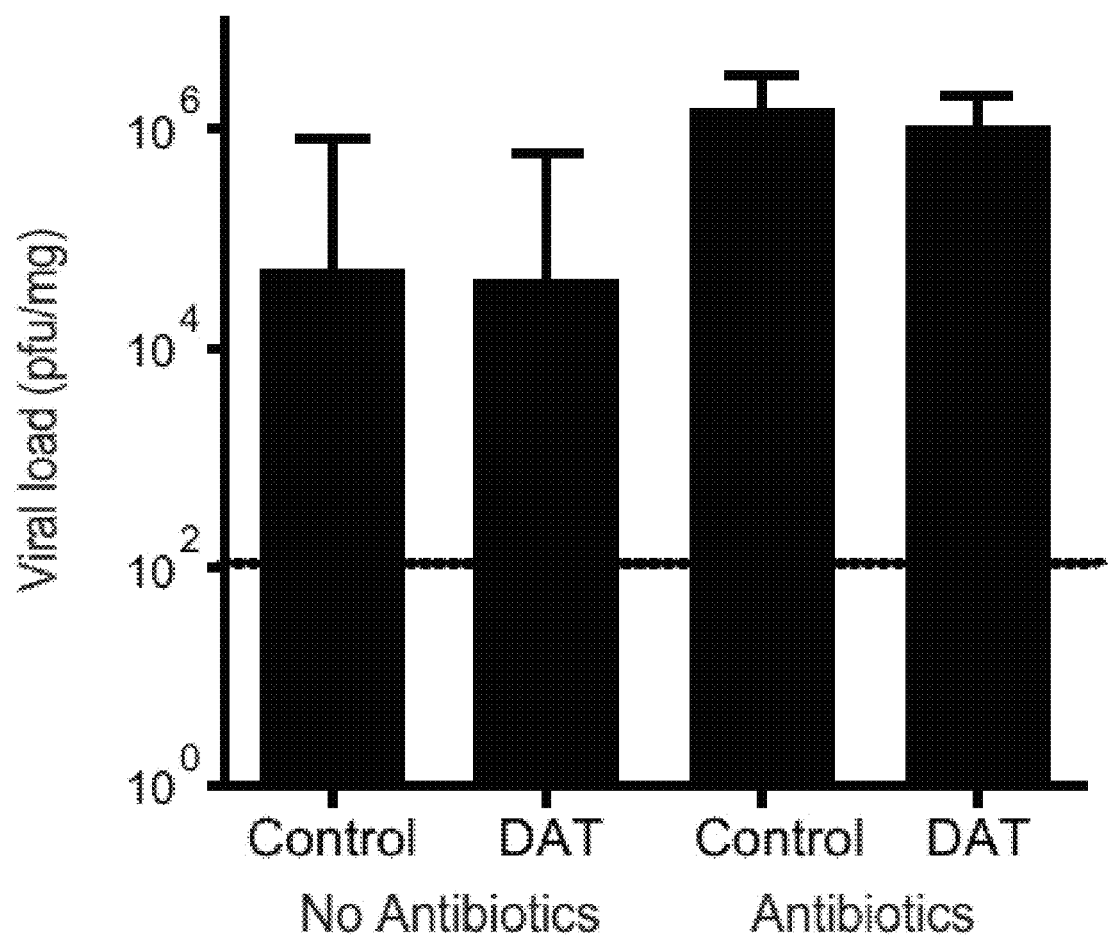
FIG. 12 depicts a graph showing that viral titers are not altered by desaminotyrosine treatment. Infectious viral load by plaque assay 5 days postinfection for mice infected treated with or without antibiotics and then with or without desaminotyrosine and subsequently infected with 5,000 pfu of Influenza H1N1. n=5 mice per group.

To further delineate whether microbiome-associated metabolites are sufficient to augment type I IFN activity and influence anti-viral responses, desaminotyrosine was chosen. After a 2-week antibiotic course, treated mice with desaminotyrosine orally or vehicle control and polyIC injections and were found to have increased type I IFN activity in the serum compared to mice treated with polyIC alone (FIG. 4D). To determine whether desaminotyrosine constituted the relevant metabolite by which the microbiome protects from Influenza infection, control or antibiotic (VNAM) treated mice that received either vehicle control or desaminotyrosine in the drinking water beginning 7 days prior to Influenza infection and continuing through infection were compared. Consistent with prior literature, antibiotic treated mice demonstrated increased morbidity and mortality compared to controls. Strikingly, desaminotyrosine treatment not only resulted in marked reductions in Influenza associated mortality and weight loss compared to vehicle treated controls, but also, recused the phenotypes associated with antibiotic treatment (FIG. 4E, FIG. 4F, and FIG. 4G). This protection was not associated with a difference in viral titers 5 days postinfection (FIG. 12). Consistent with our hypothesis that desaminotyrosine protects from Influenza infection by enhancing type I IFN signaling, desaminotyrosine had no effect on survival in Ifnar animals (FIG. 4H and FIG. 4I). The effect of desaminotyrosine timing on protection from influenza was investigated. Pretreating mice with the desaminotyrosine for only 1 week prior to infection and then stopping treatment protected the animals from mortality in a similar manner to pretreatment for 1 week and then continuing the metabolite during infection (FIG. 4J). However, if desaminotyrosine was administered starting 2 days after infection, the animals were not protected; in fact, their mortality outcomes were markedly worse than animals who never received the metabolite (FIG. 4J). Mechanistically, 24 hours of desaminotyrosine pretreatment decreased influenza RNA in bone marrow derived macrophages in an IFN-dependent manner (FIG. 4K). Collectively, these experiments demonstrate that augmentation of type I IFN signaling by bacterially-derived metabolites constitutes a critical mechanism by which the microbiome protects from Influenza infection.

Here it was demonstrated that conditioning of the host to type I IFN prior to infection results in dramatic protection from Influenza infection. Surprisingly, this exposure does not ultimately impact viral infectivity or replication, but instead, alters the host response to Influenza infection. Moreover, it was shown that microbially-associated metabolites can enhance IFN signaling, and one metabolite, desaminotyrosine, is sufficient to promote favorable outcomes in the face of lethal viral infection. These findings demonstrate that manipulation of IFN signaling can be readily achieved and that the enteric microbiome may impact responses to serious viral threats via its effects on this important signaling pathway.

Figure 18A:
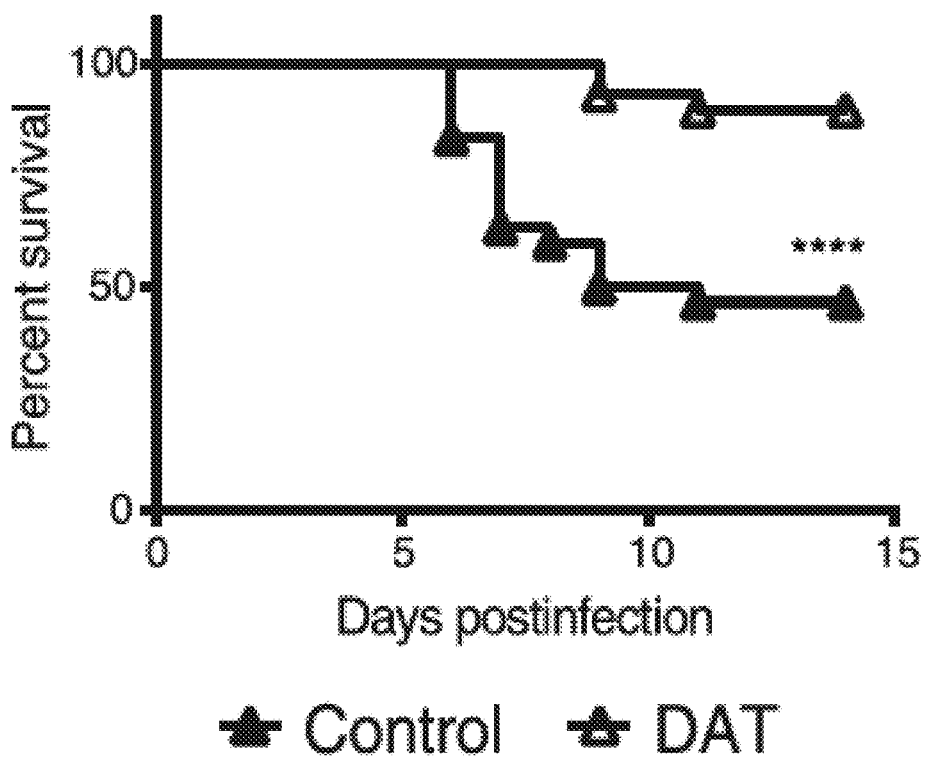
FIG. 18A, FIG. 18B, FIG. 18C, FIG. 18D, FIG. 18E, FIG. 18F, FIG. 18G, FIG. 18H, FIG. 18I, FIG. 18J, FIG. 18K, FIG. 18L, and FIG. 18M depict graphs and representative images that show desaminotyrosine protects from influenza via type I IFN signaling.
Figure 18B:
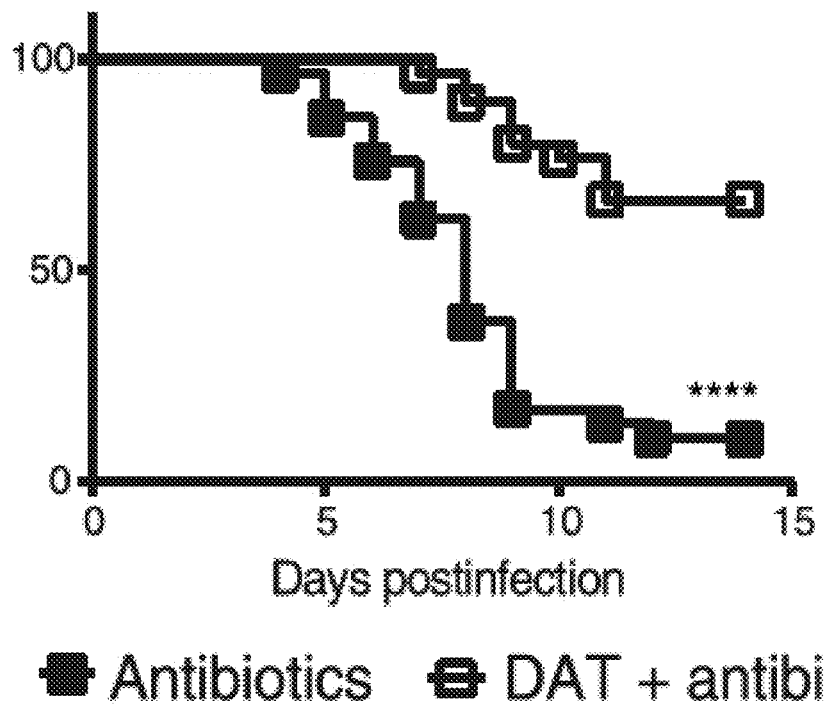
Figure 18C:
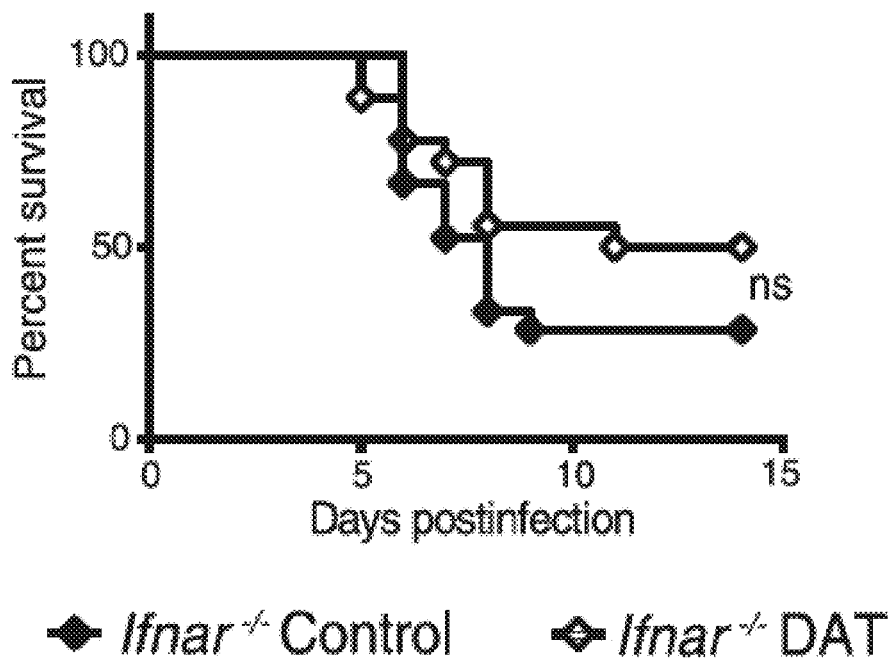

Groups of mice with or without VNAM pretreatment were given 200 mM desaminotyrosine or vehicle in drinking water 7 days prior to influenza infection and throughout infection for 14 days. Consistent with prior finding,[14-16] antibiotic treated mice showed increased mortality and weight loss compared with non-antibiotic treated mice (FIG. 18A, FIG. 18B, FIG. 4E, and FIG. 4F). Influenza-associated mortality and weight loss were less in desaminotyrosine-treated mice compared with controls (FIG. 18A, FIG. 18B, FIG. 4E, FIG. 4F, FIG. 19C, and FIG. 19D). Consistent with our hypothesis that desaminotyrosine protects from influenza infection by enhancing type I IFN signaling prior to infection, desaminotyrosine conferred no beneficial effect on weight loss or survival in Ifnar$^{-/-}$ animals (FIG. 18C and FIG. 4H). Desaminotyrosine protection was not H1N1 strain specific as mice infected with PR8 and California/09 were protected by desaminotyrosine (FIG. 19E, FIG. 19F, FIG. 19G, and FIG. 19H).

Figure 18D:
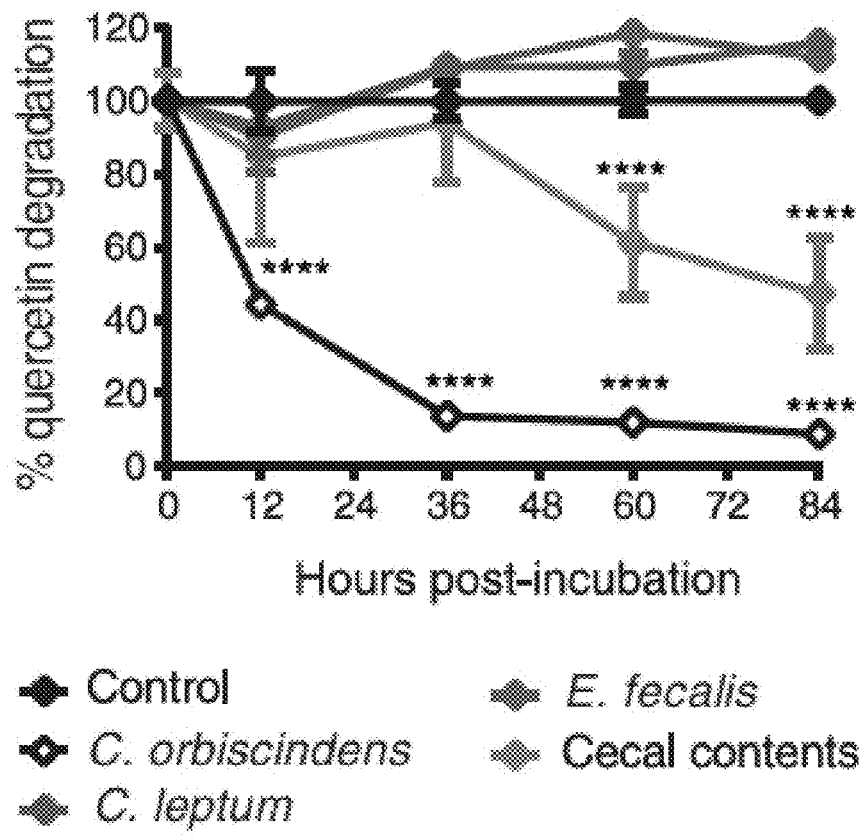
Figure 18E:
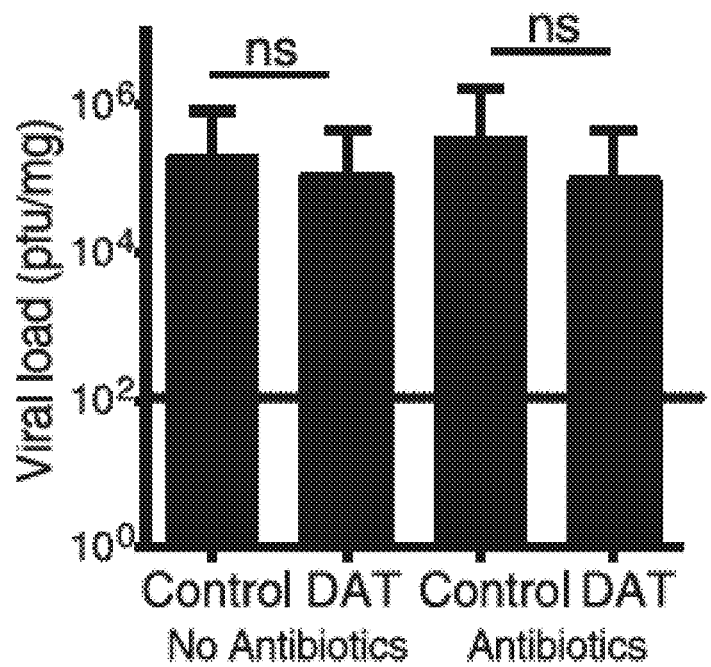
Figure 18F:
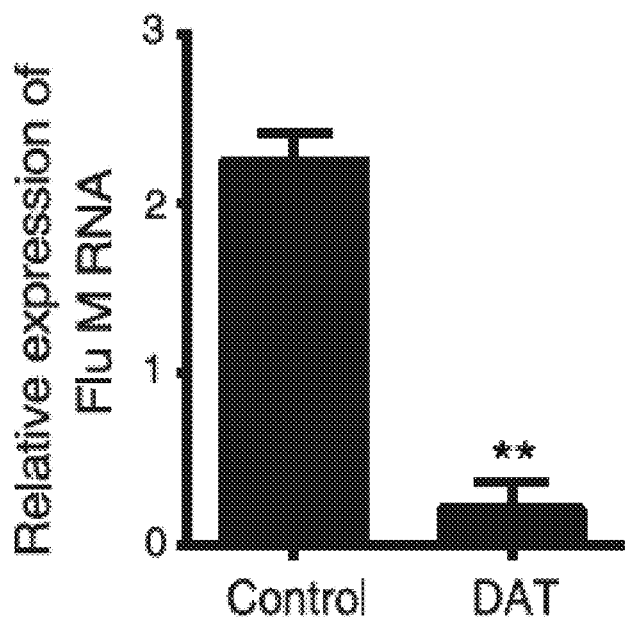
Figure 18H:
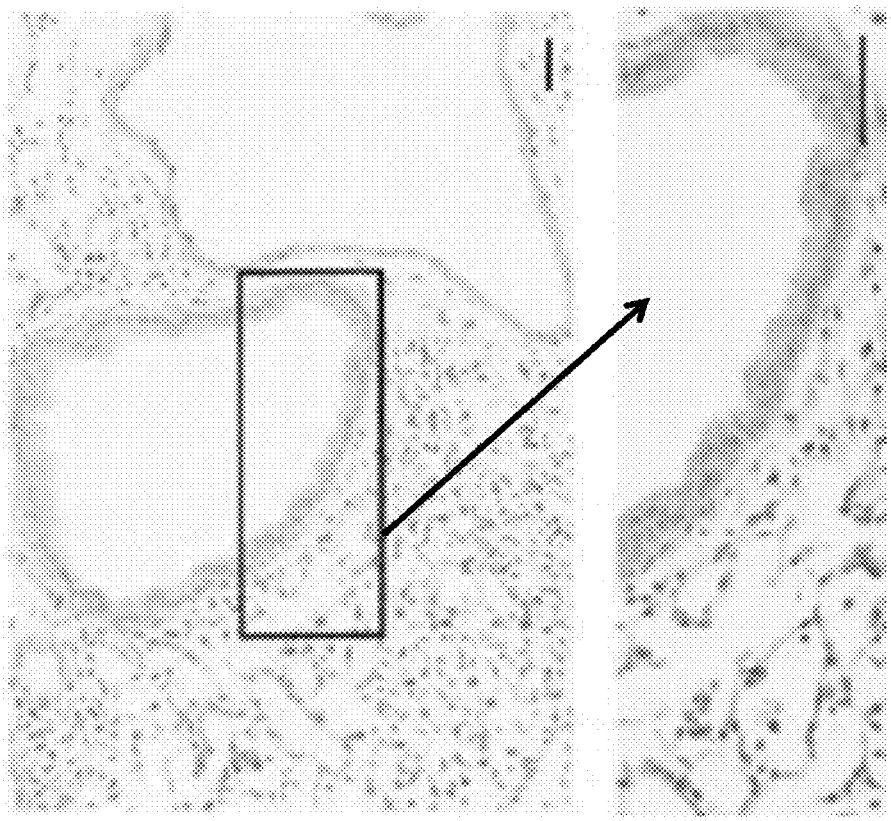
Figure 18G:
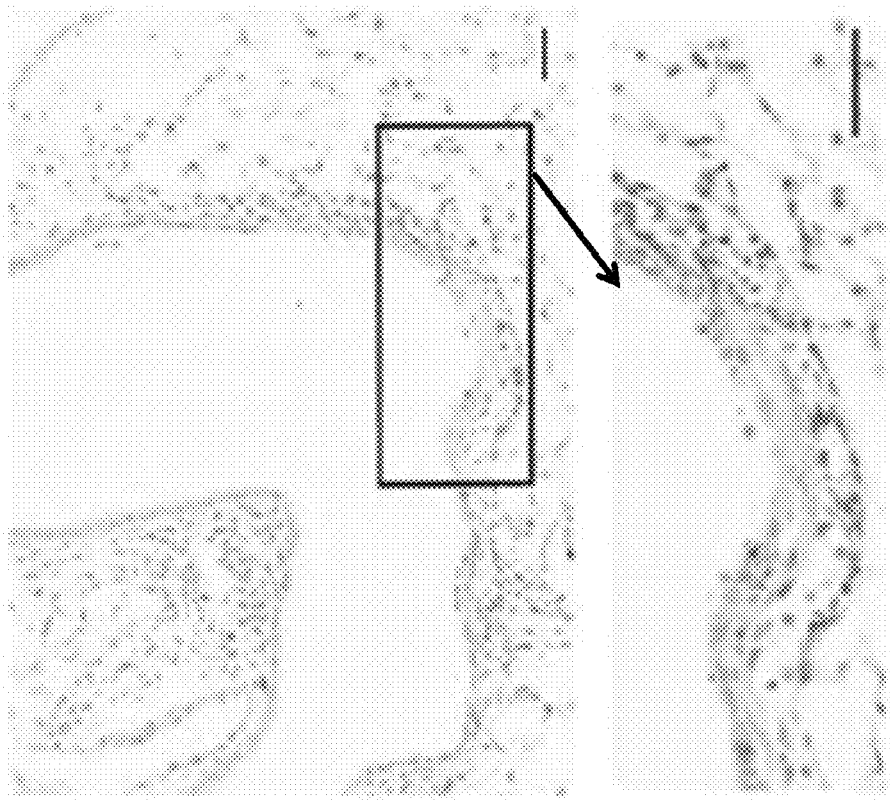

It was hypothesized that augmentation of type I IFN activity by desaminotyrosine protects mice via a similar mechanism as found in the Irgm1$^{-/-}$ mice. Indeed, desaminotyrosine protection was not associated with a difference in viral titers 5 days postinfection (FIG. 18E), but less viral RNA was found in the lungs of mice treated with desaminotyrosine than controls (FIG. 18F). Similar to our findings in the Irgm1$^{-/-}$ gain of function model, greater airway epithelial damage and apoptosis were observed in control lungs than in desaminotyrosine-treated mice (FIG. 18G, FIG. 18H, FIG. 18I, FIG. 18J, FIG. 18K, FIG. 18L, FIG. 19J, FIG. 19K, FIG. 19L, FIG. 19M, and FIG. 19N). These findings show that desaminotyrosine also dampens host damage associated with influenza infection.

Figure 18I:
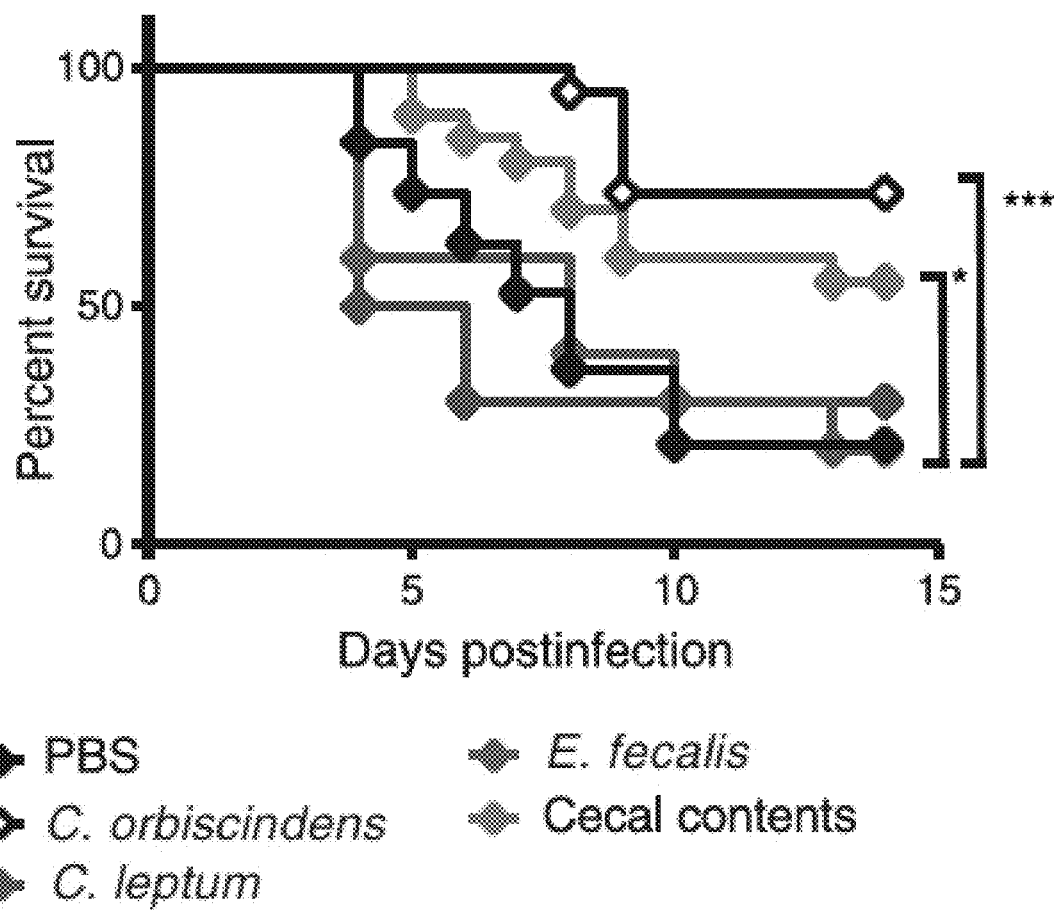
Figure 18K:
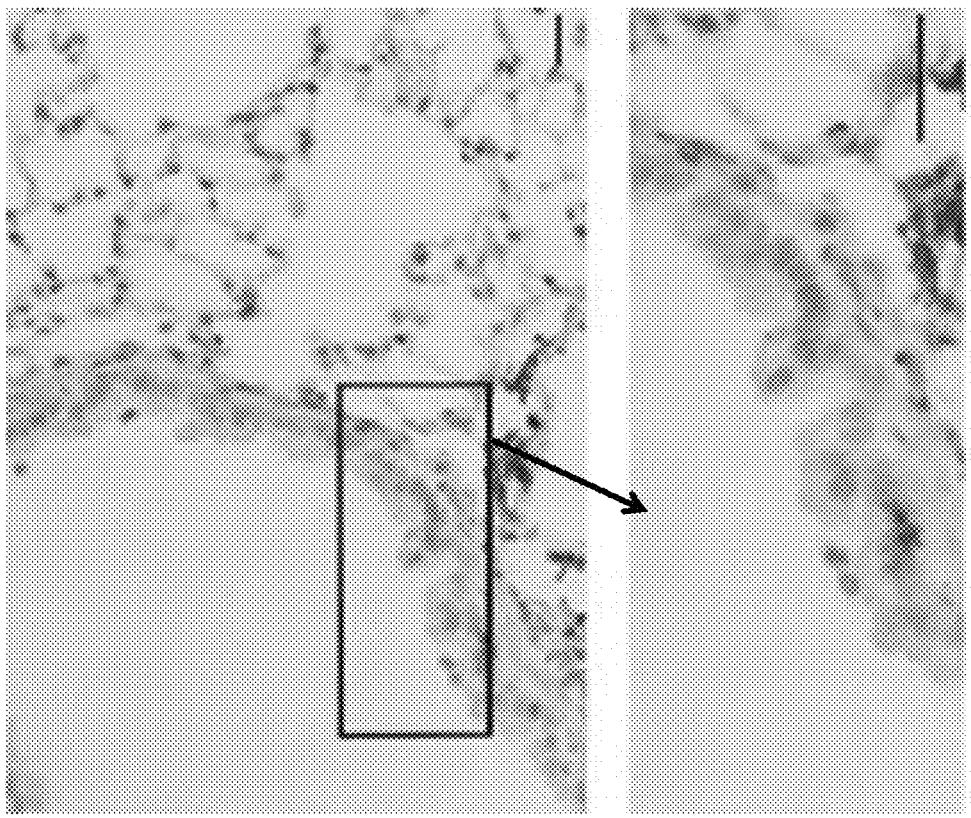
Figure 18J:
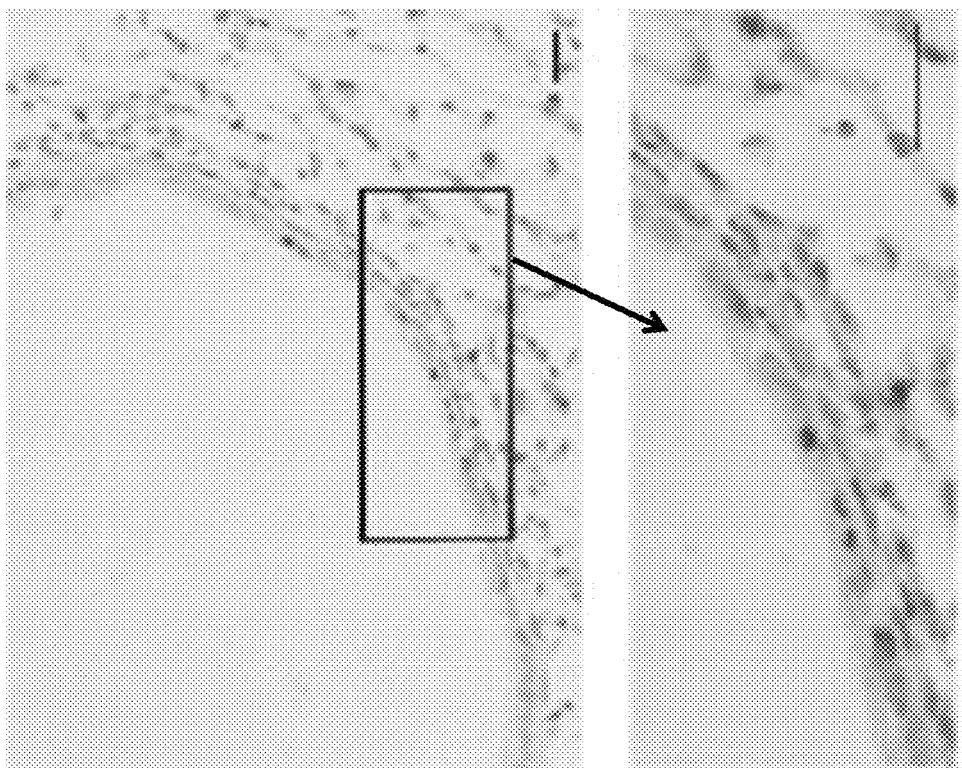
Figure 18L:
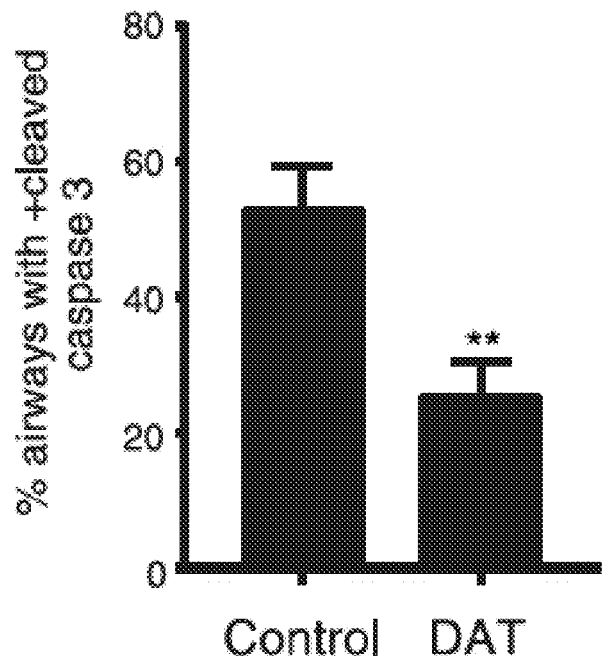
Figure 18M:
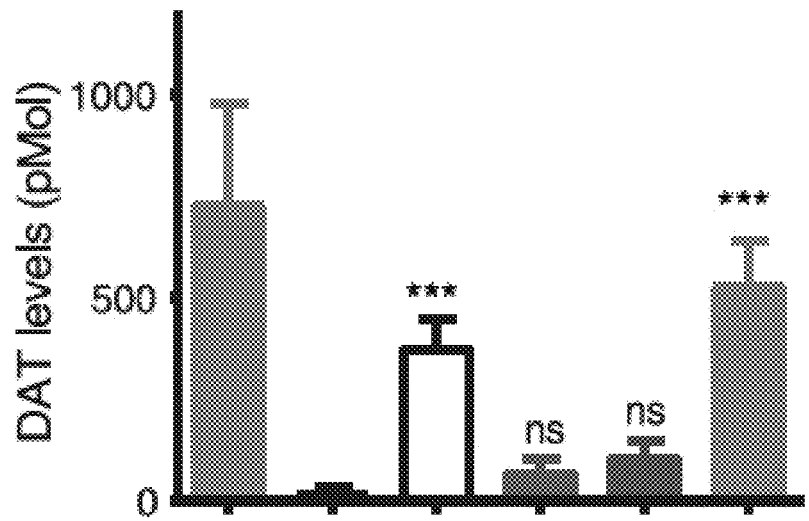
Figure 19A:
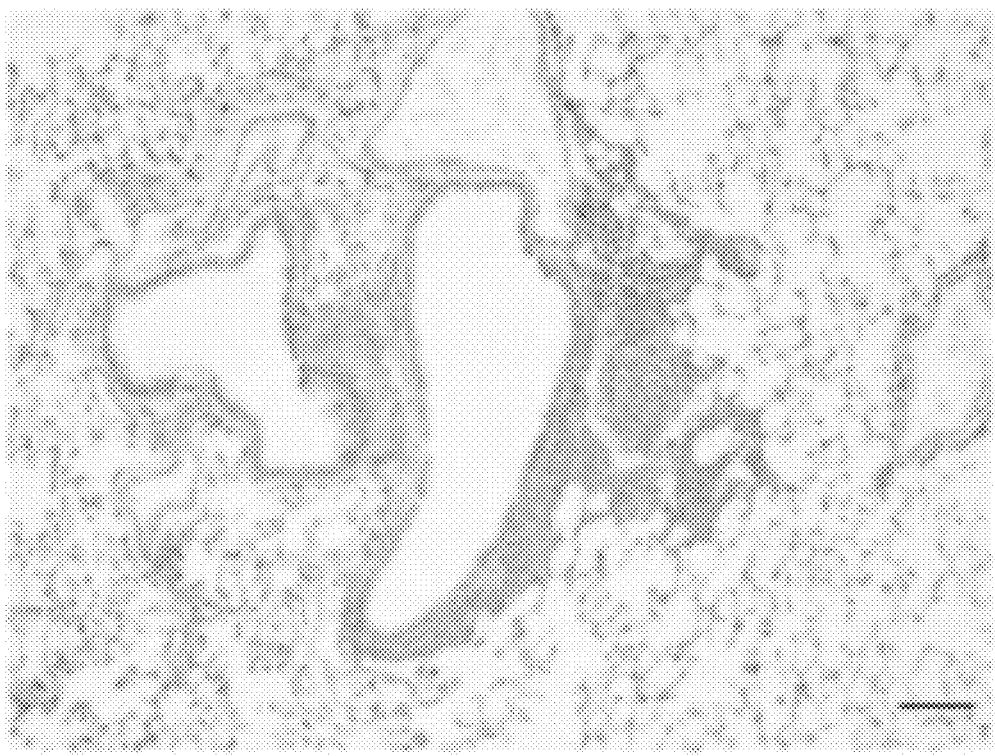
FIG. 19A, FIG. 19B, FIG. 19C, FIG. 19D, FIG. 19E, FIG. 19F, FIG. 19G, FIG. 19H, FIG. 19I, FIG. 19J, FIG. 19L, FIG. 19K, FIG. 19M, and FIG. 19N (FIG. 19A and FIG. 19B) Representative images of influenza H1N1 staining by polyclonal antibody on lung cross sections from wild-type (WT) (FIG. 19A) and Irgm1$^{-/-}$ (FIG. 19B) mice 6 days postinfection (representative images from 5-6 mice per group from two experiments). Bar=200 μm.
Figure 19B:
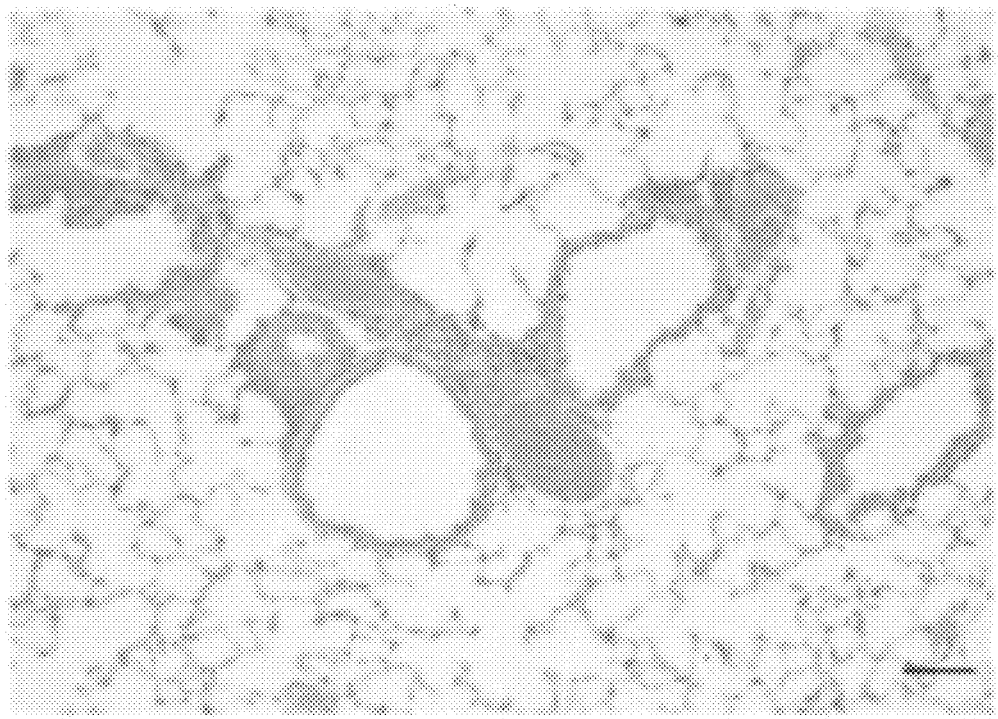
Figure 19C:
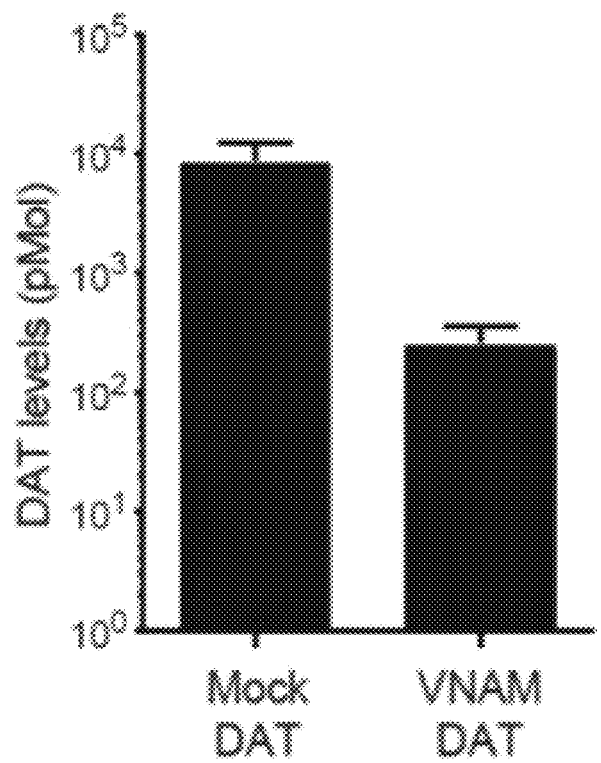
Figure 19D:
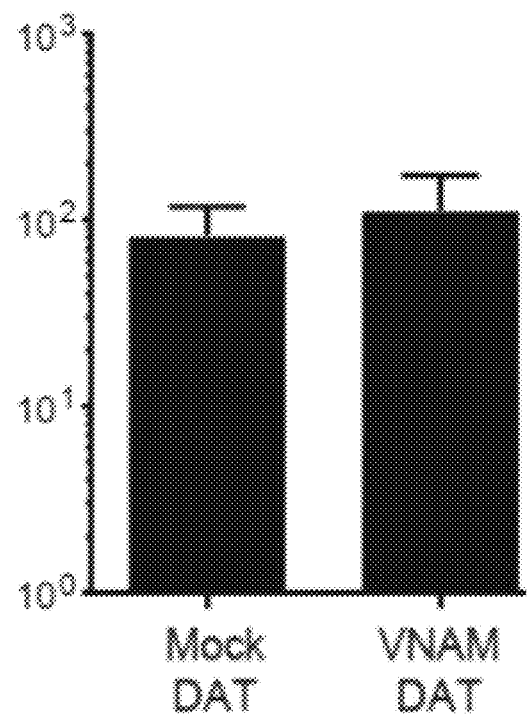
Figure 19E:
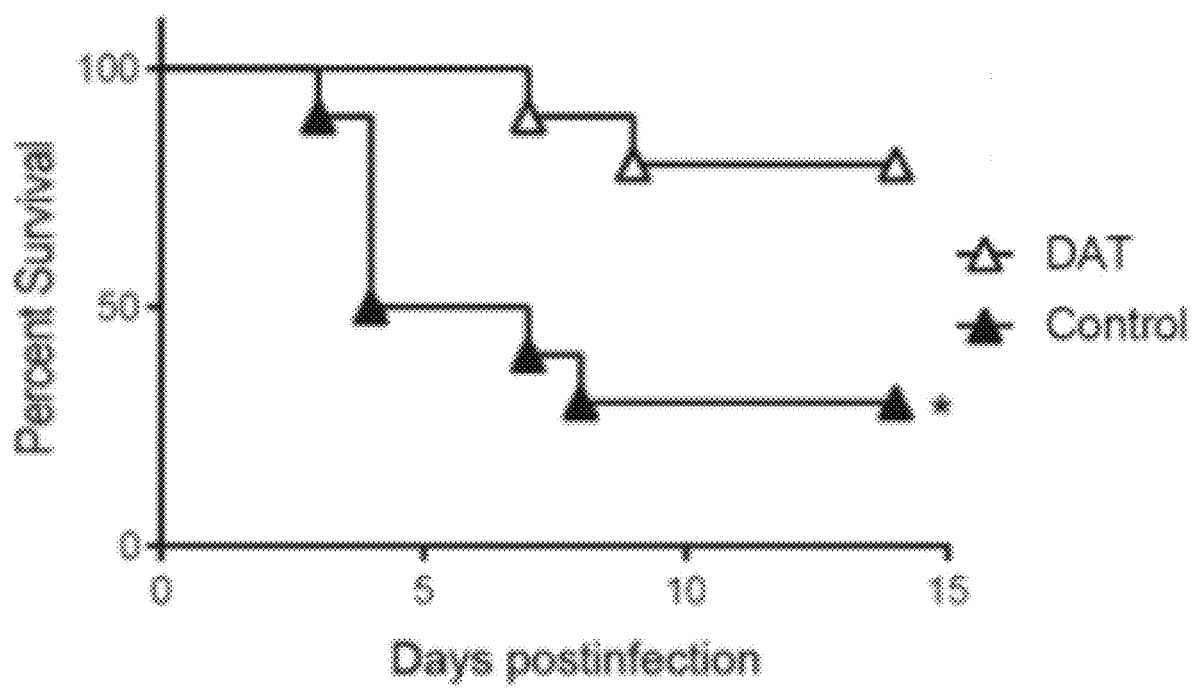
Figure 19F:
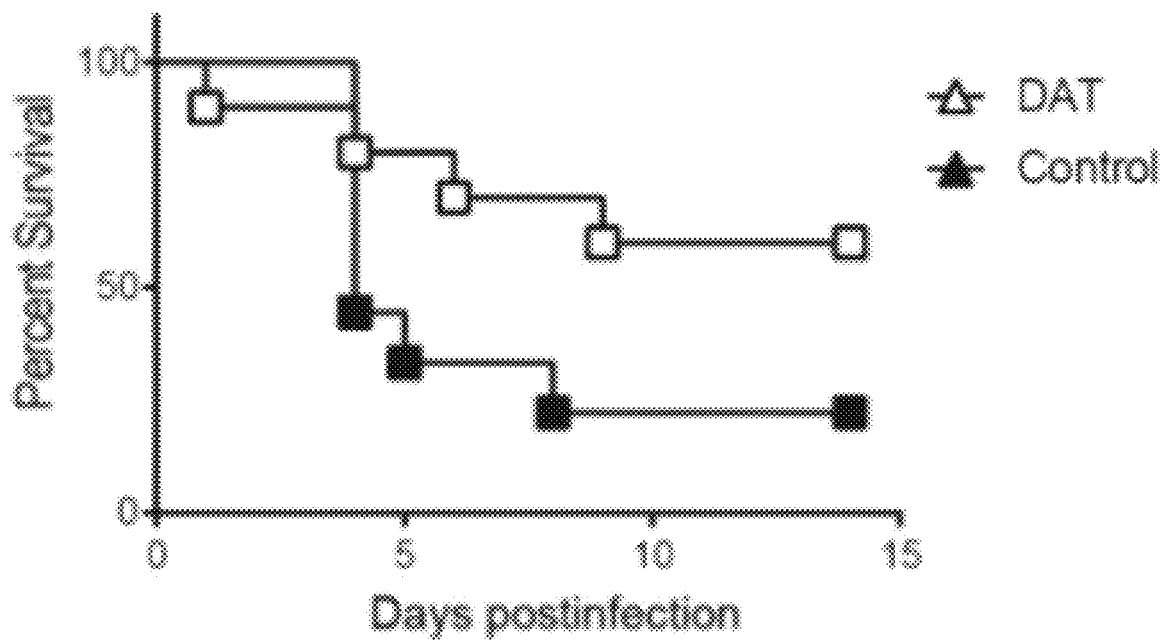
Figure 19G:
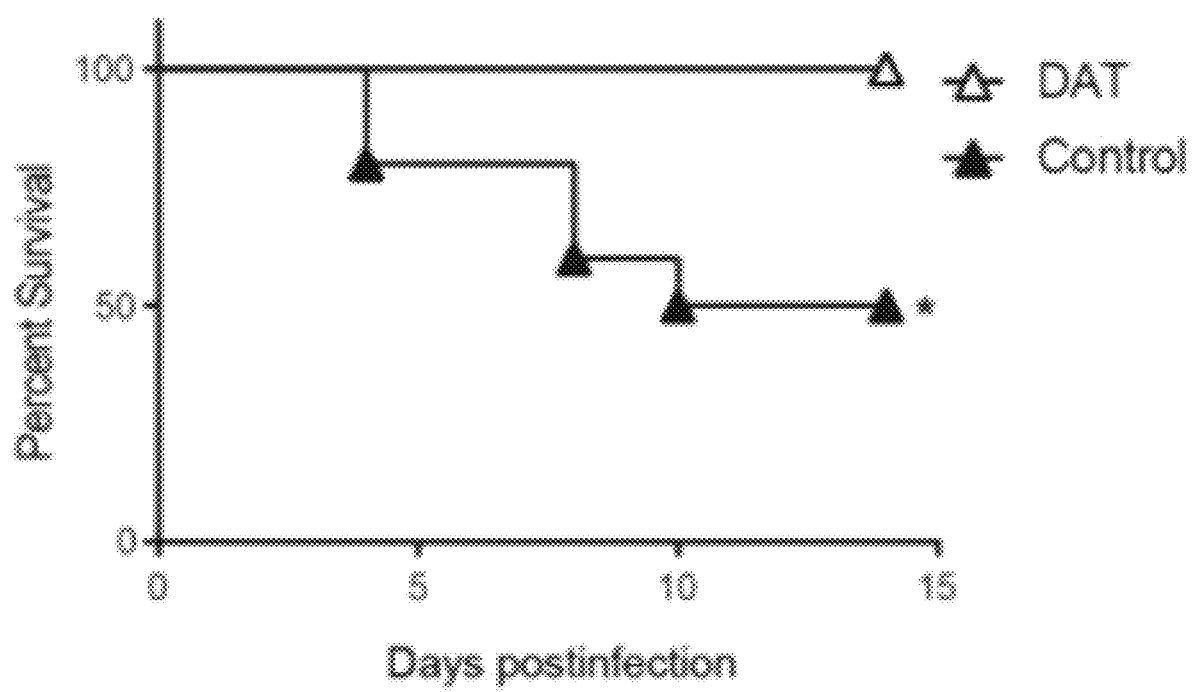
Figure 19H:
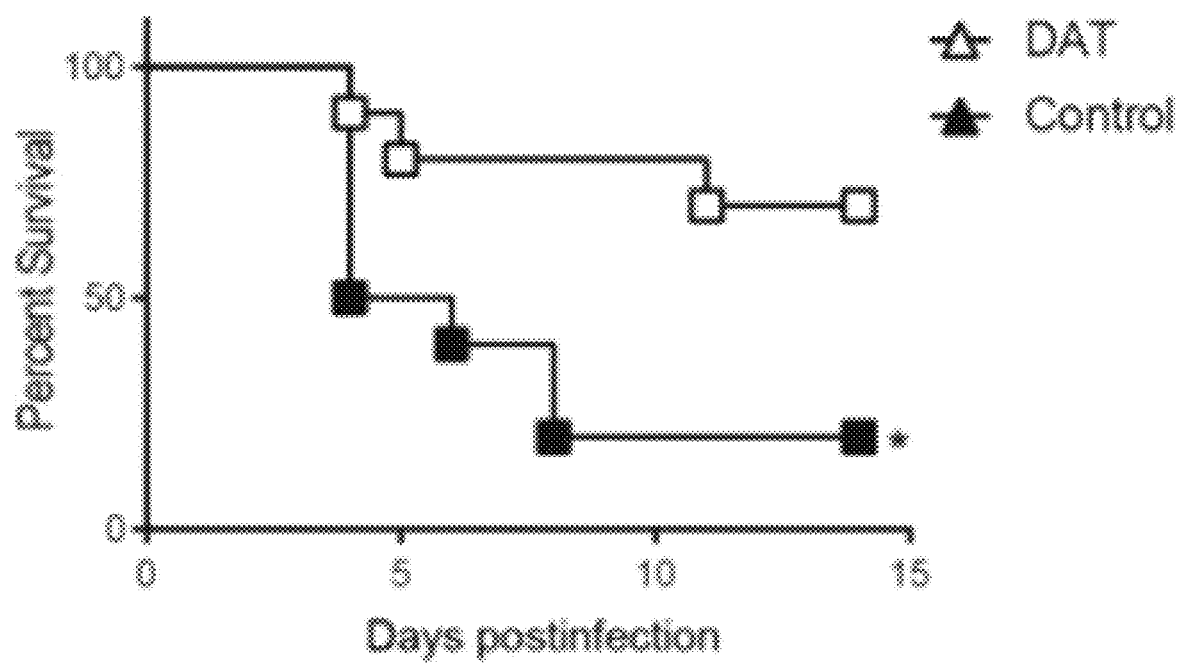
Figure 19I:
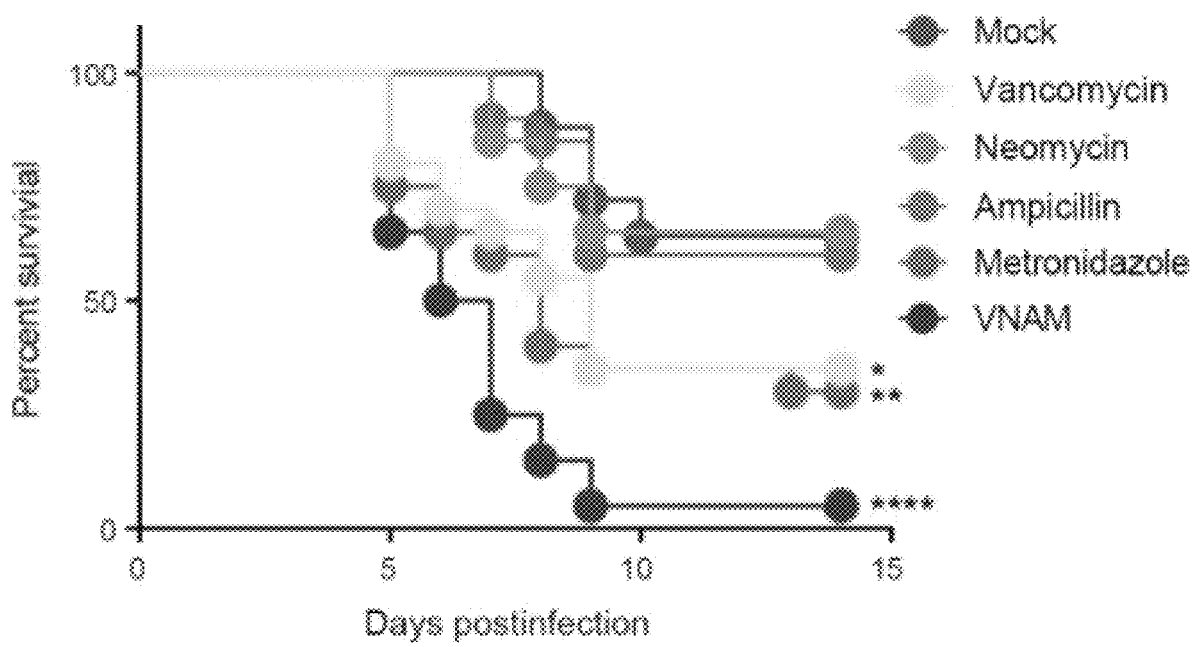
Figure 19J:
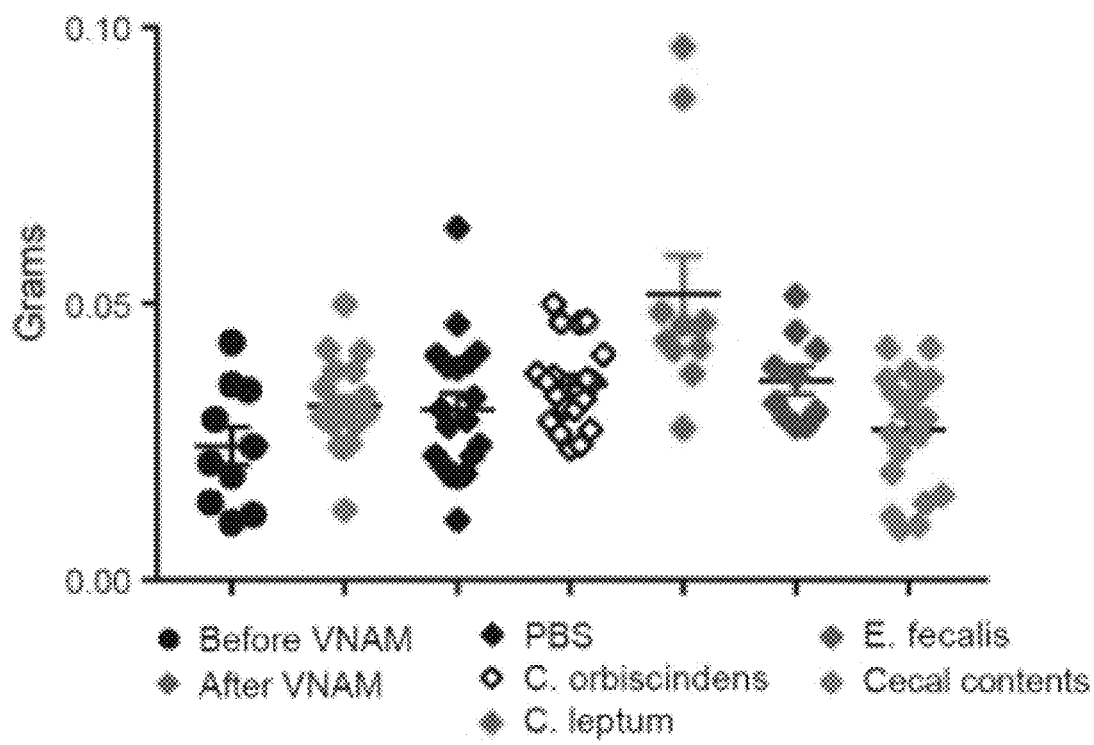
Figure 19K:
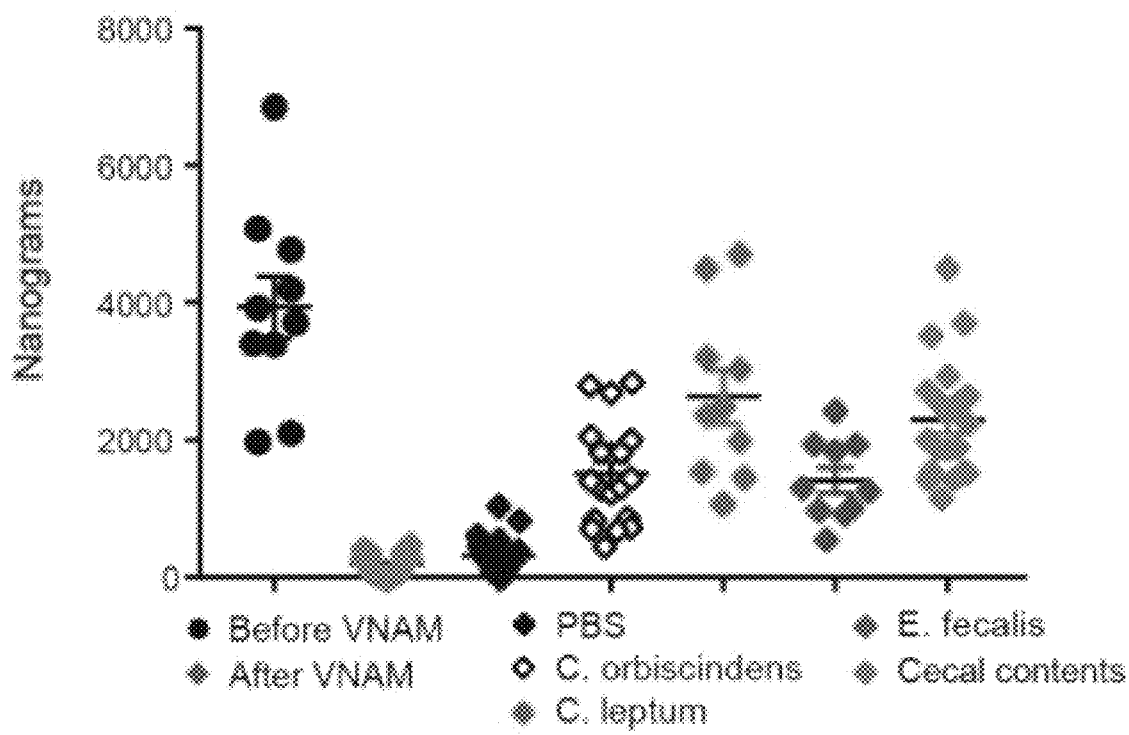
Figure 19L:
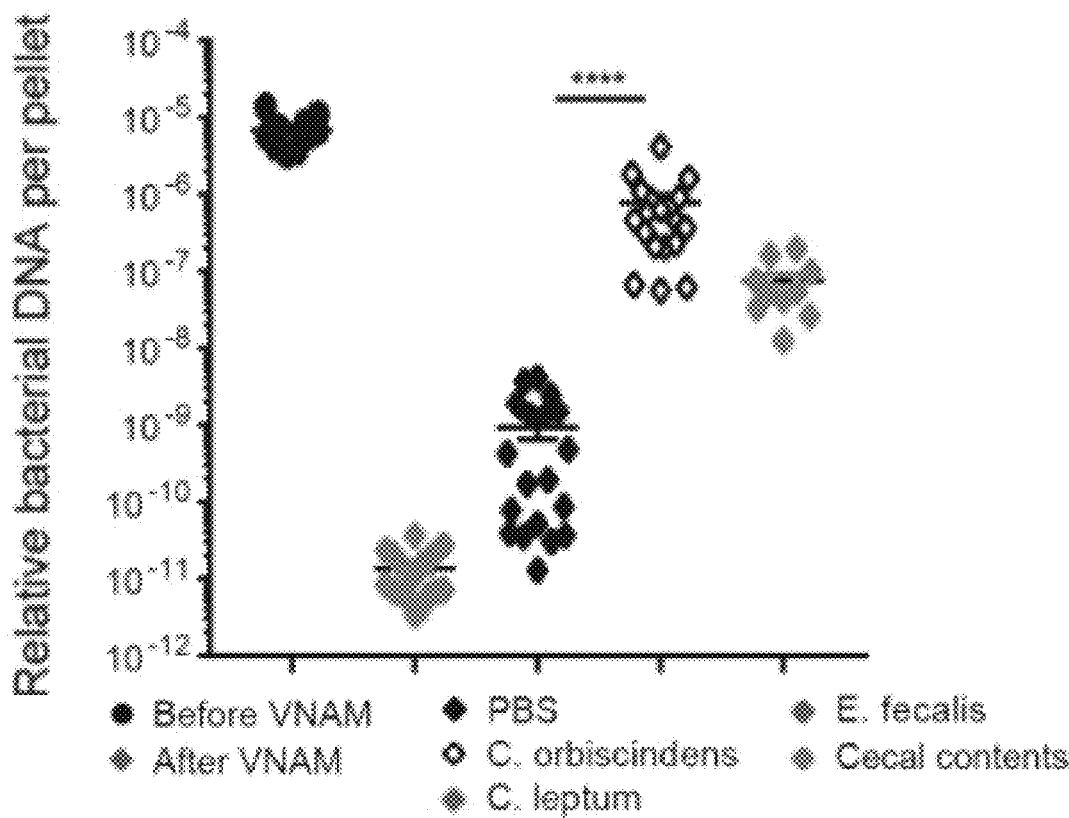
Figure 19M:
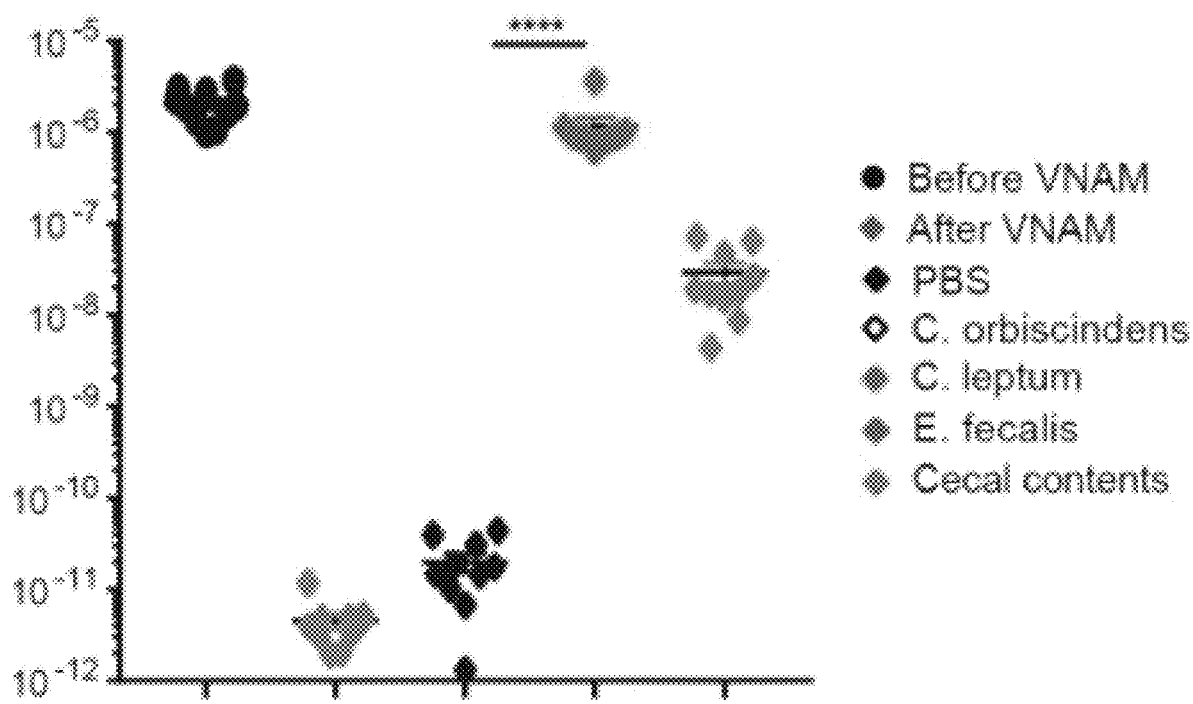
Figure 19N:
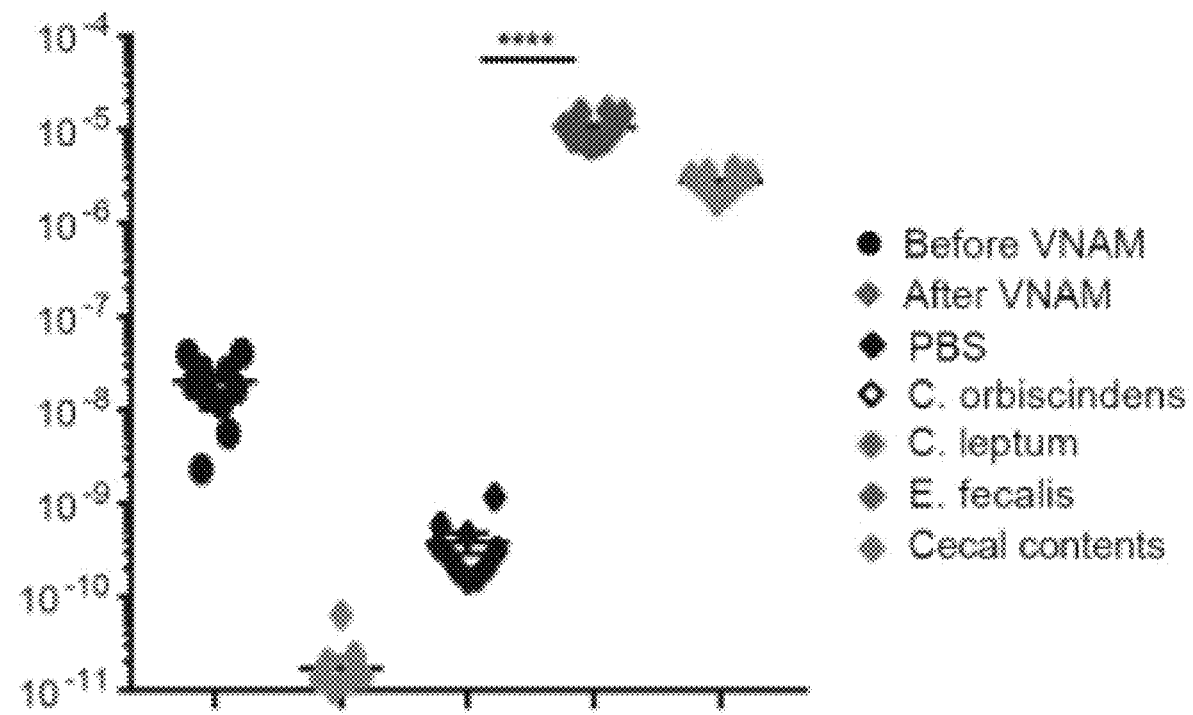

Desaminotyrosine generation occurs during flavonoid metabolism, and specific microbiota species metabolize flavonoids.[23] A limited screen of the human fecal microbiota for flavonoid metabolism to desaminotyrosine identified *Clostridium orbiscindens* (FIG. 18D).[24] Interestingly, Clostridial species are sensitive to metronidazole and vancomycin,[25] the individual antibiotics that enhanced influenza associated-mortality (FIG. 19I). To investigate the role of specific bacteria in desaminotyrosine generation and ultimately influenza protection, isolates of *Clostridium orbiscindens, Clostridium leptum* (a related bacterium), and *Enterococcus faecalis* (an unrelated microbiota member sensitive to vancomycin) were obtained. Consistent with prior studies, it was found *Clostridium orbiscindens* degraded flavonoid substrates effectively (FIG. 18D). Importantly, mouse cecal contents containing multiple prokaryote species also degraded the flavonoid substrate, albeit, less effectively than pure cultures of *Clostridium orbiscindens* (FIG. 18D). In contrast, other vancomycin-sensitive species, *Clostridium leptum* and *Enterococcus faecalis*, did not degrade flavonoids (FIG. 18D). Groups of VNAM pretreated mice were gavaged with *Clostridium orbiscindens*, mouse cecal contents, or PBS prior to influenza infection. *Clostridium orbiscindens* and cecal content gavage protected mice from influenza mortality and morbidity (FIG. 18I), whereas gavage with *Clostridium leptum* or *Enterococcus faecalis* did not alter mortality even though these organisms colonized mice efficiently (FIG. 18I). Moreover, *Clostridium orbiscindens* and cecal contents restored fecal desaminotyrosine levels while *Clostridium leptum* and *Enterococcus faecalis* did not (FIG. 18M).

Figure 2V:
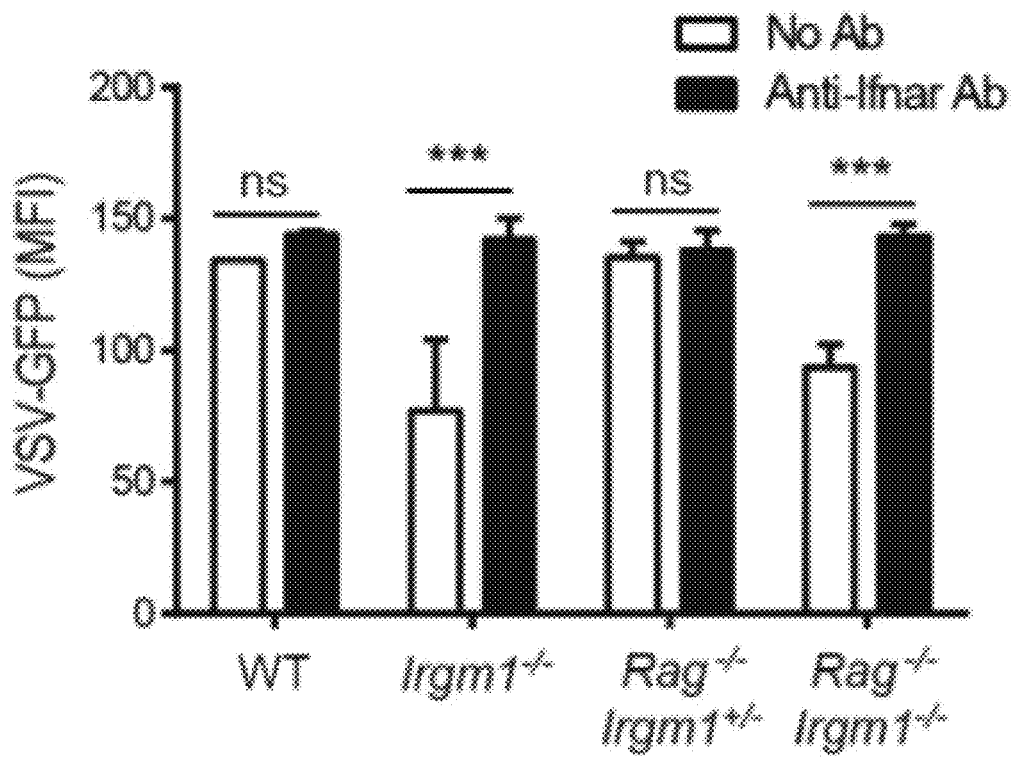
Figure 2W:
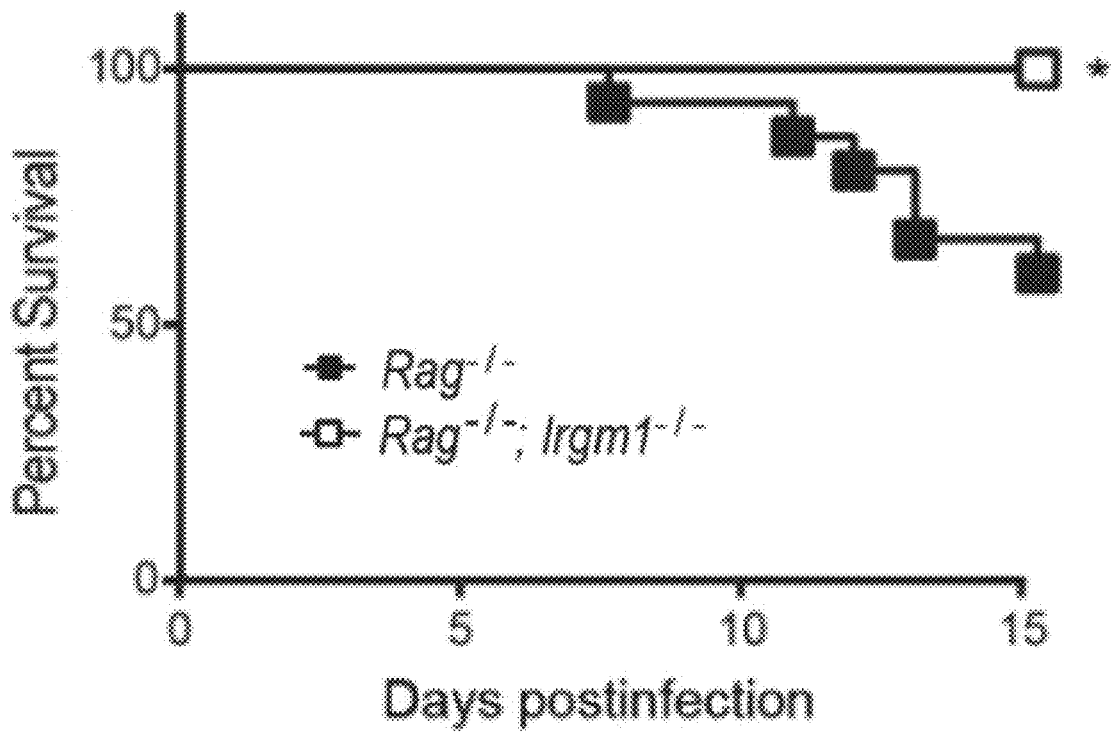
Figure 20A:
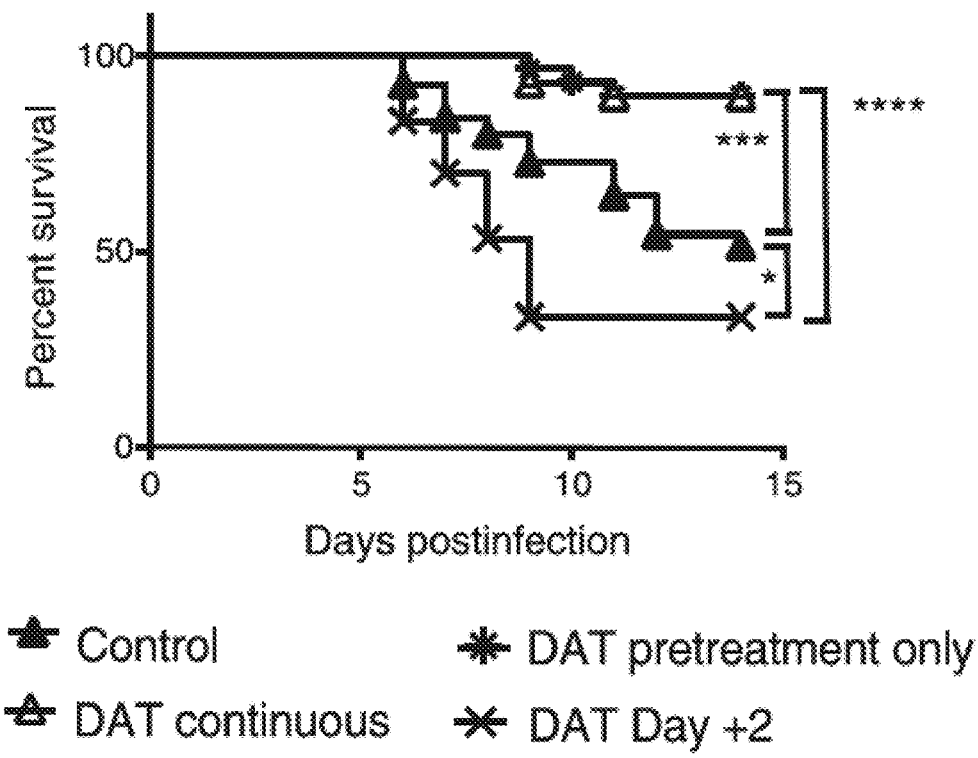
Figure 20B:
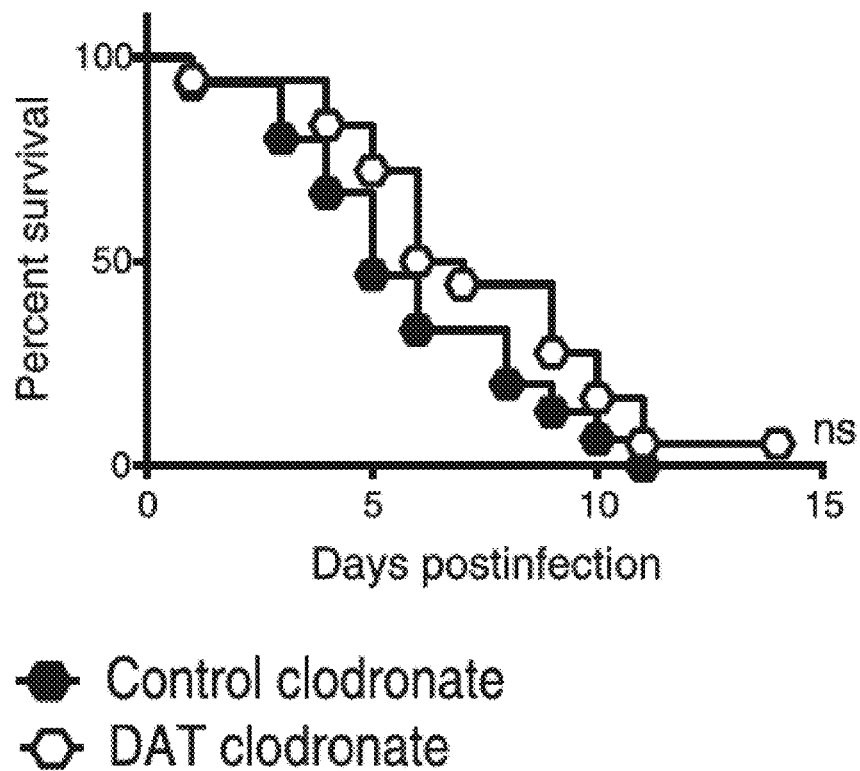
Figure 20F:
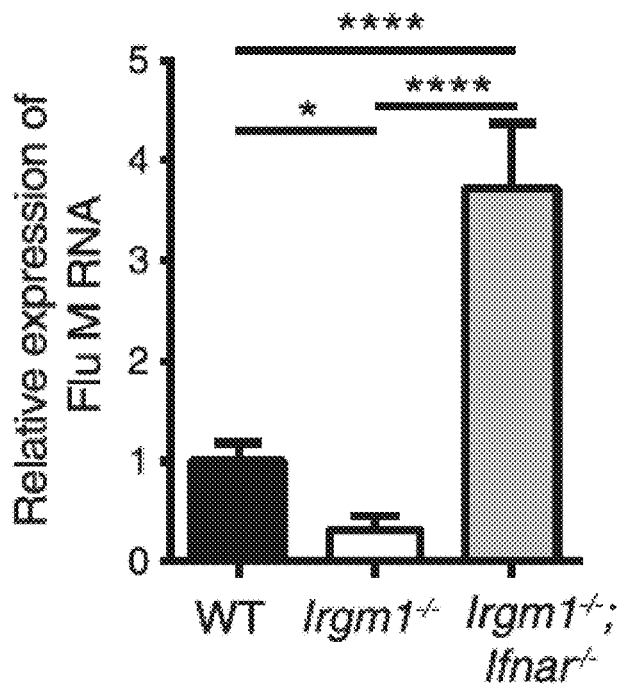
Figure 21:
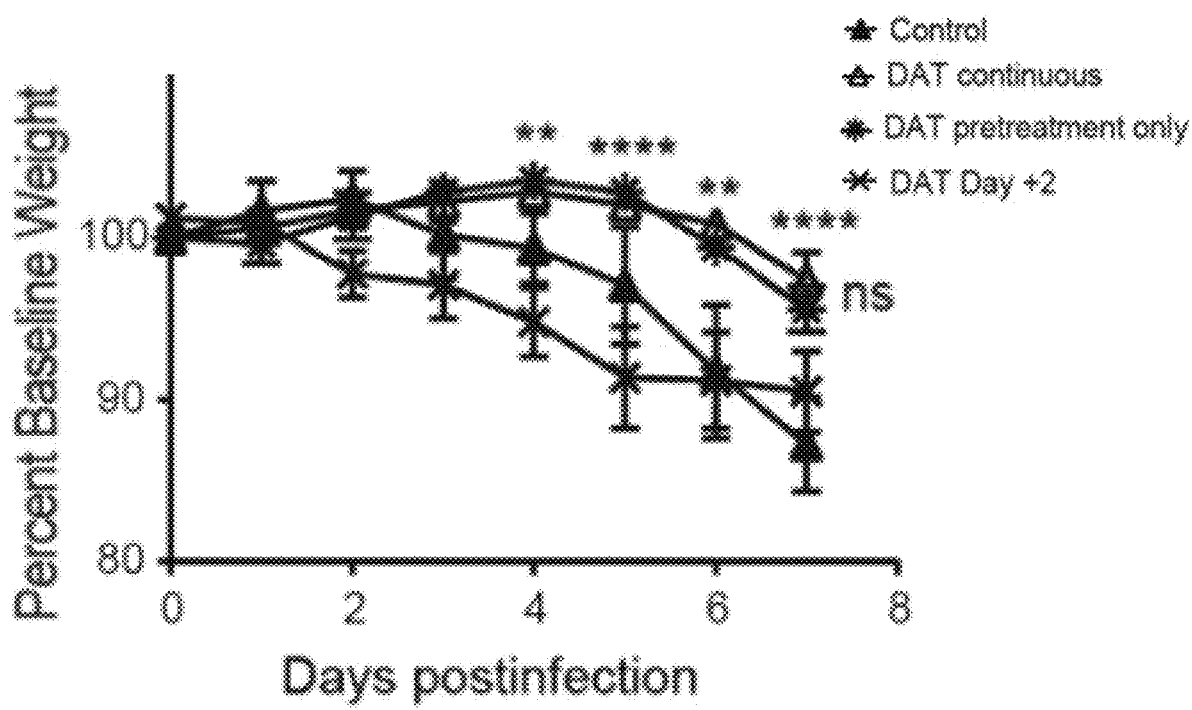
FIG. 21 depicts a graph showing percent weight loss of groups of wild-type mice with variations on the timing desaminotyrosine treatment with respect to infection. Control=no desaminotyrosine; desaminotyrosine continuous=one week pretreatment and continuous treatment postinfection; desaminotyrosine pretreatment only=one week pretreatment only; desaminotyrosine day +2=treatment commenced 2 days postinfection (n=30 mice per group from two experiments). Asterisk represents significance between desaminotyrosine pretreatment group and desaminotyrosine rescue group; ns denotes no significance between desaminotyrosine continuous group and desaminotyrosine pretreatment group. p<0.01 and **p<0.0001 and ns denotes not statistically significant by ANOVA with Tukey's multiple comparisons.
Figure 22A:
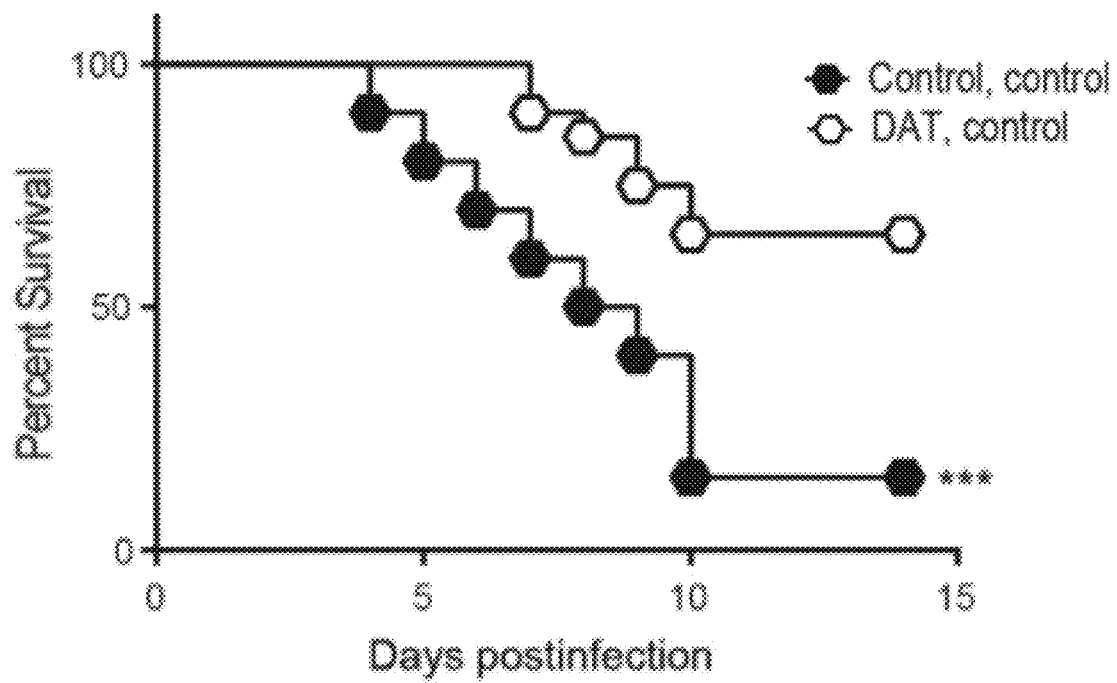
FIG. 22A and FIG. 22B depict graphs showing Kaplan-Meier survival analysis of infected wild-type mice (FIG. 22A) all treated with control liposomes and either control or desaminotyrosine (n=15-20 mice per group from two experiments). Kaplan-Meier survival analysis of infected wild-type (WT) (FIG. 22A) and Irgm1$^{-/-}$ mice (FIG. 22B) treated with control liposomes (n=6-11 mice per group from three experiments). ***p<0.001 by Mantel-Cox test.
Figure 22B:
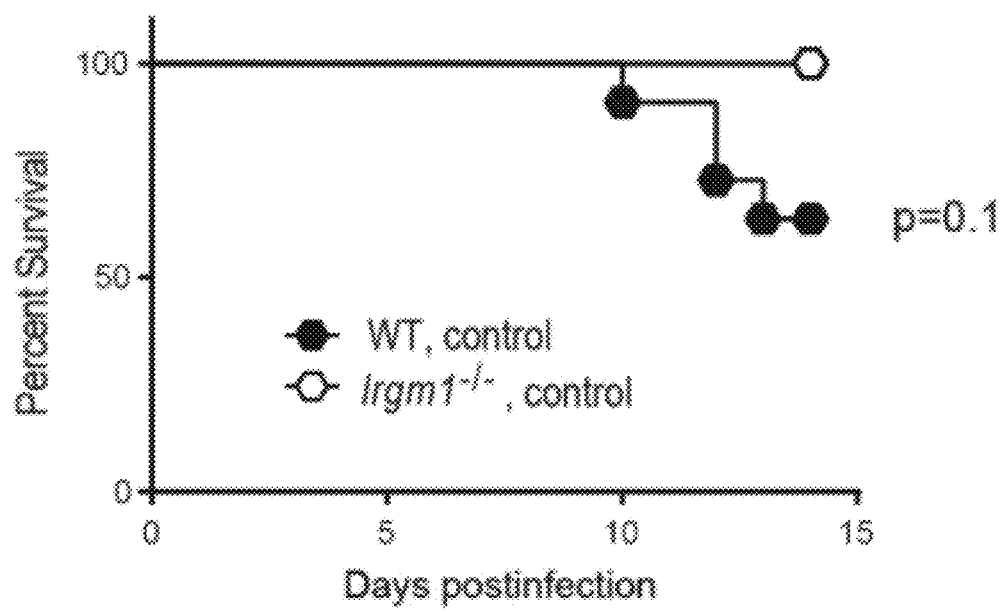

Pretreating mice with desaminotyrosine for one week prior to influenza infection, followed by cessation of treatment at the time of infection, protected mice from mortality and weight loss similarly to mice continuously treated (FIG. 20A and FIG. 21). However, administration of desaminotyrosine starting two days postinfection led to a worse outcome than in mice who never received desaminotyrosine (FIG. 20A and FIG. 21). This finding suggests that priming of the immune system by desaminotyrosine prior to infection is protective. Consistent with this idea, Irgm1$^{-/-}$; Rag1$^{-/-}$, which maintain elevated levels of type I IFN, showed protection compared to Rag1$^{-/-}$ mice (FIG. 2V and FIG. 2W), implying that innate, not adaptive, immunity is crucial for the protective priming effect of type I IFN.

Within the lung, phagocytes are essential mediators of innate immune responses to bacterial and viral pathogens.[28] To determine whether type I IFN mediates protection from influenza infection through a phagocytic-dependent mechanism, mice were treated systemically with clodronate liposomes to deplete lung phagocytes[29] (FIG. 9). Clodronate treatment also abolished desaminotyrosine and Irgm1$^{-/-}$ mediated protection (FIG. 20B, FIG. 20C, FIG. 22A, and FIG. 22B). These results indicate that phagocytes are required for type I IFN-mediated protection from influenza infection.

Figure 20G:
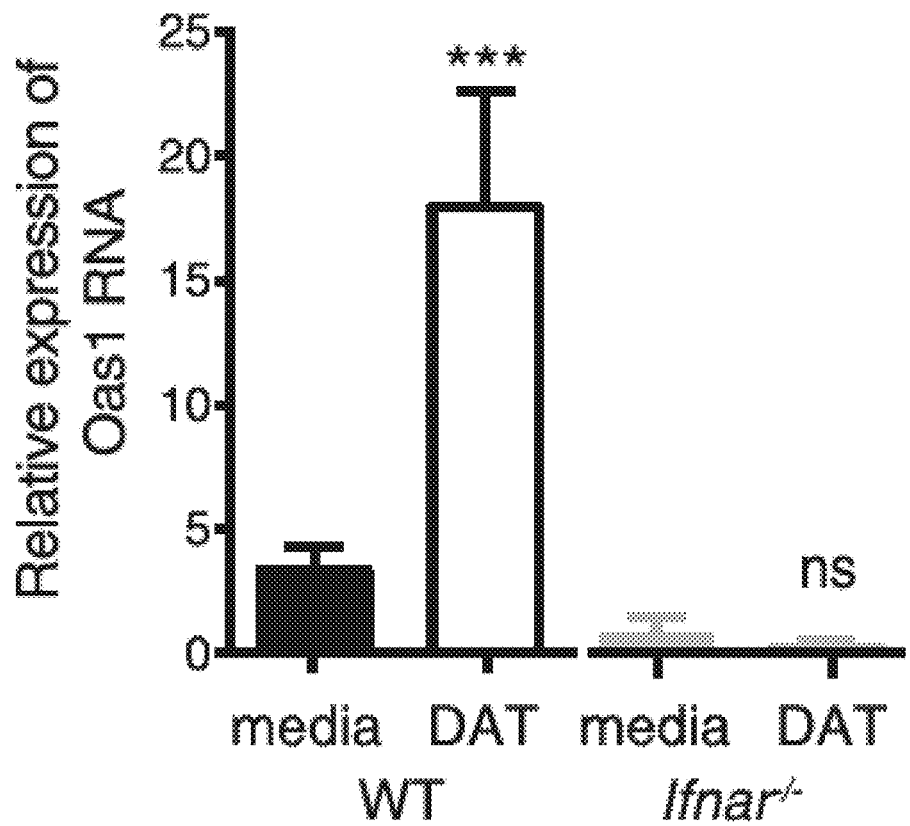
Figure 20H:
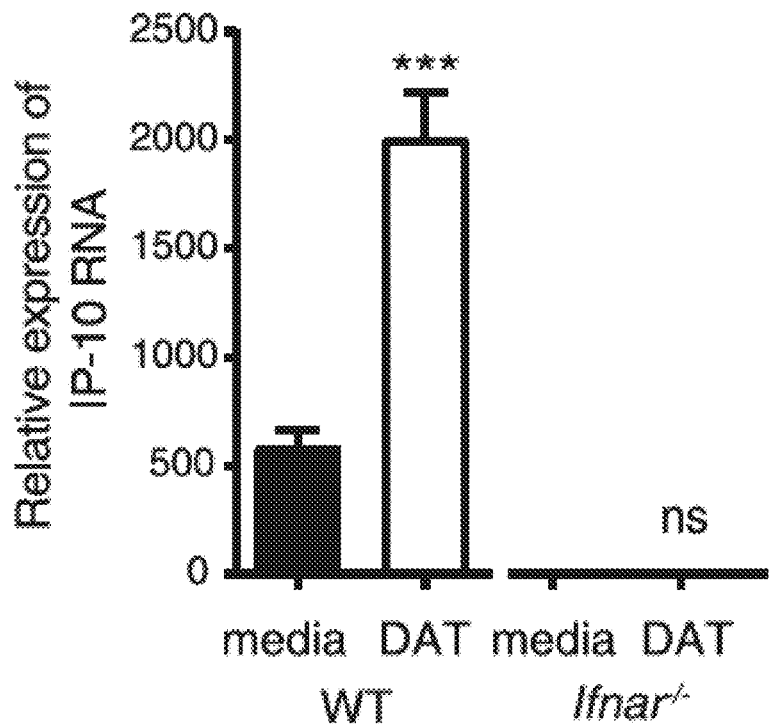
Figure 20I:
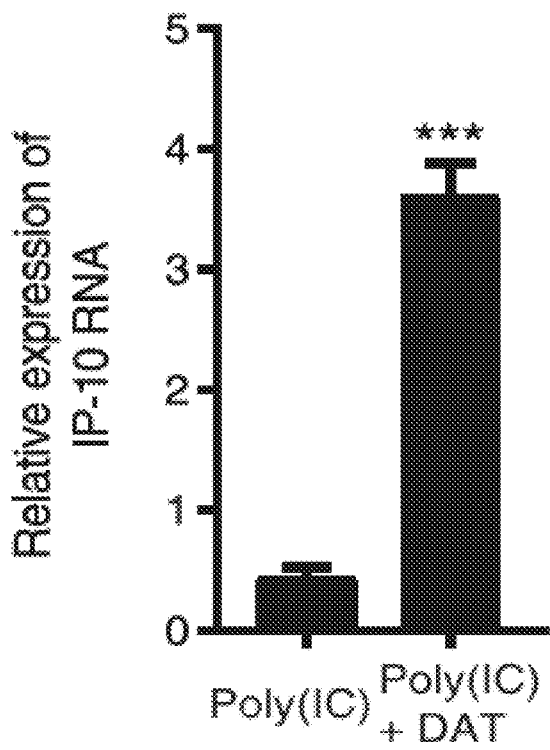
Figure 20J:
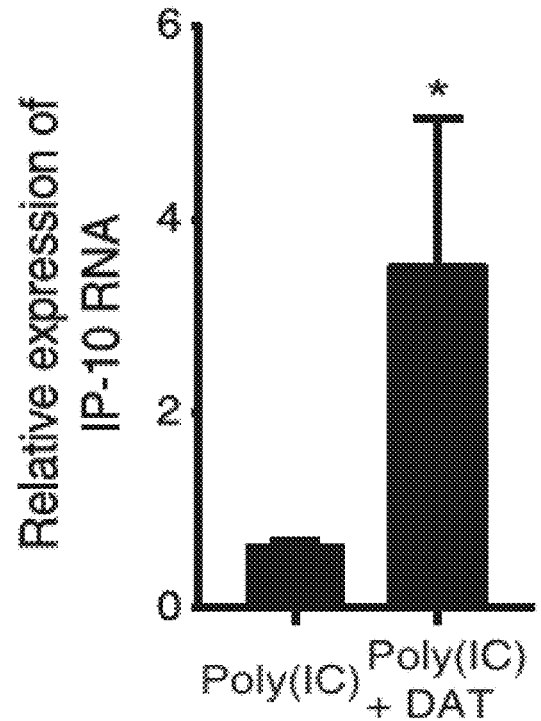
Figure 20K:
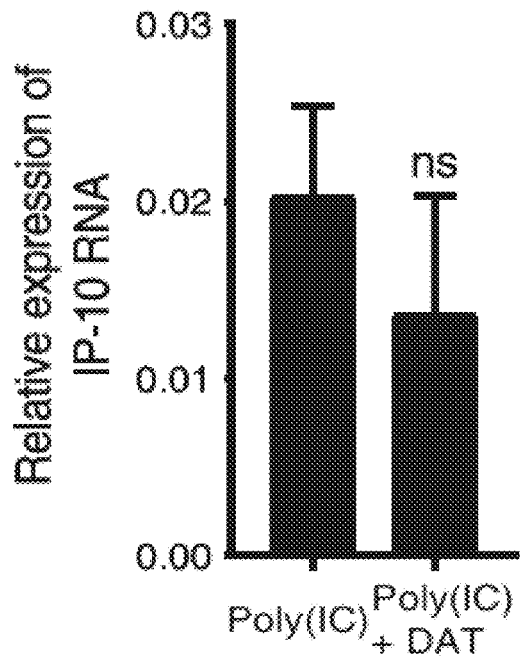
Figure 20L:
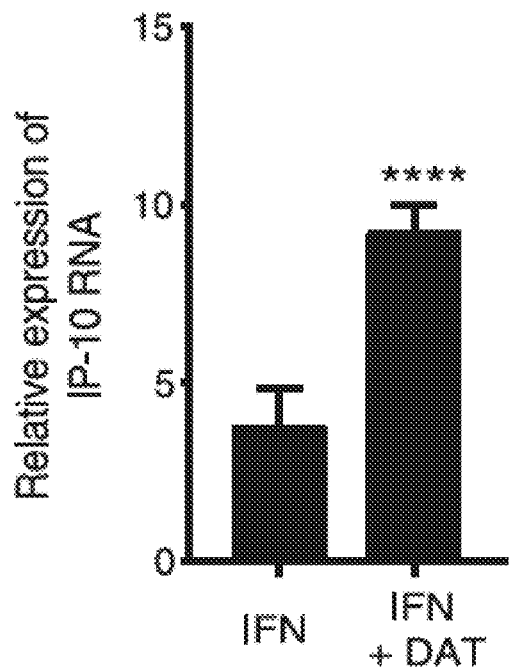
Figure 20M:
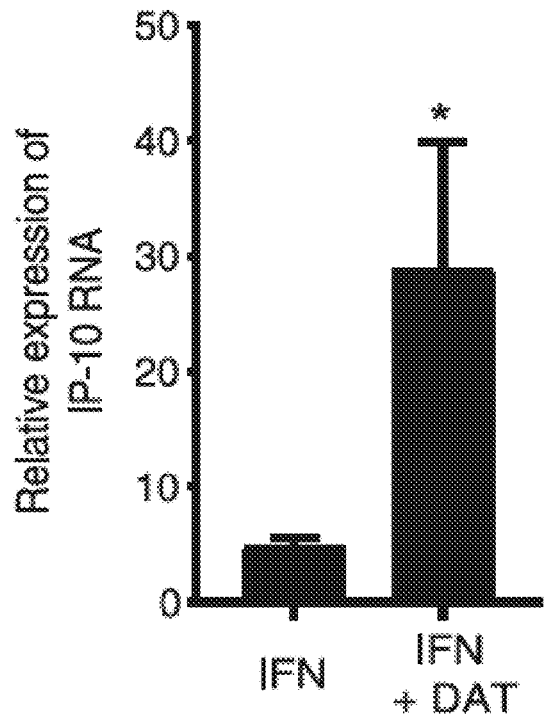
Figure 20N:
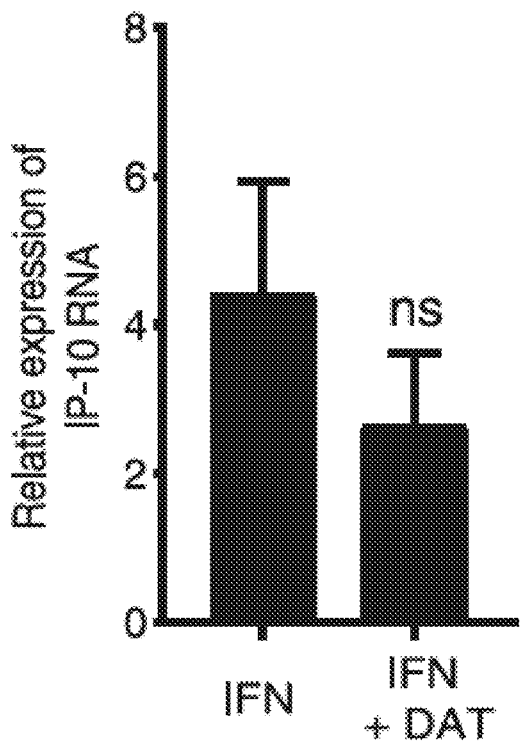

Similarly to lung homogenates, influenza viral RNA was depleted in desaminotyrosine-treated and Irgm1$^{-/-}$ bone-marrow derived macrophages (BMDMs) in an Ifnar-dependent manner (FIG. 20D, FIG. 20E, and FIG. 10F). Desaminotyrosine pretreated BMDMs showed increased ISG transcripts after in vitro influenza infection, in an Ifnar-dependent manner (FIG. 20G and FIG. 20H). Similarly, ISG transcript abundance increased when DAT treatment was combined with either polyIC or type I IFN (FIG. 20I, FIG. 20J, FIG. 20K, FIG. 20L, FIG. 20M, and FIG. 20N).

Figure 23A:
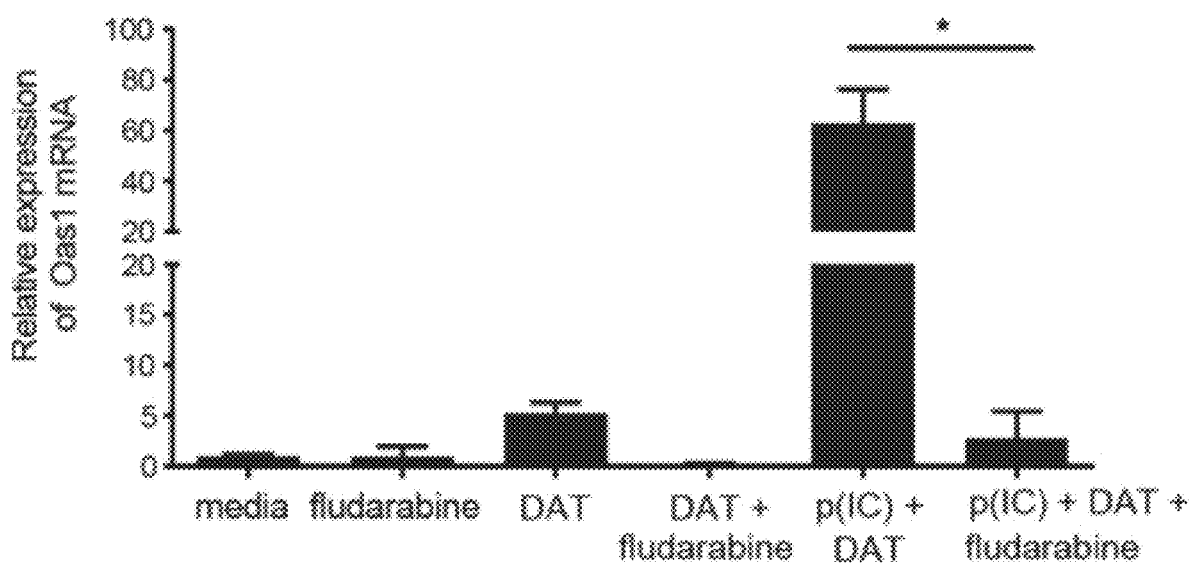
FIG. 23A, FIG. 23B, and FIG. 23C depict graphs showing relative mRNA expression of Oas1 (FIG. 23A), Mx2 (FIG. 23B), and Cxcl10 (as IP-10) (FIG. 23C) by qRT-PCR from wild-type BMDMs treated with fludarabine, desaminotyrosine, and/or poly(IC) (n=4-5 from two experiments). *p<0.05 by Mann-Whitney test.
Figure 23B:
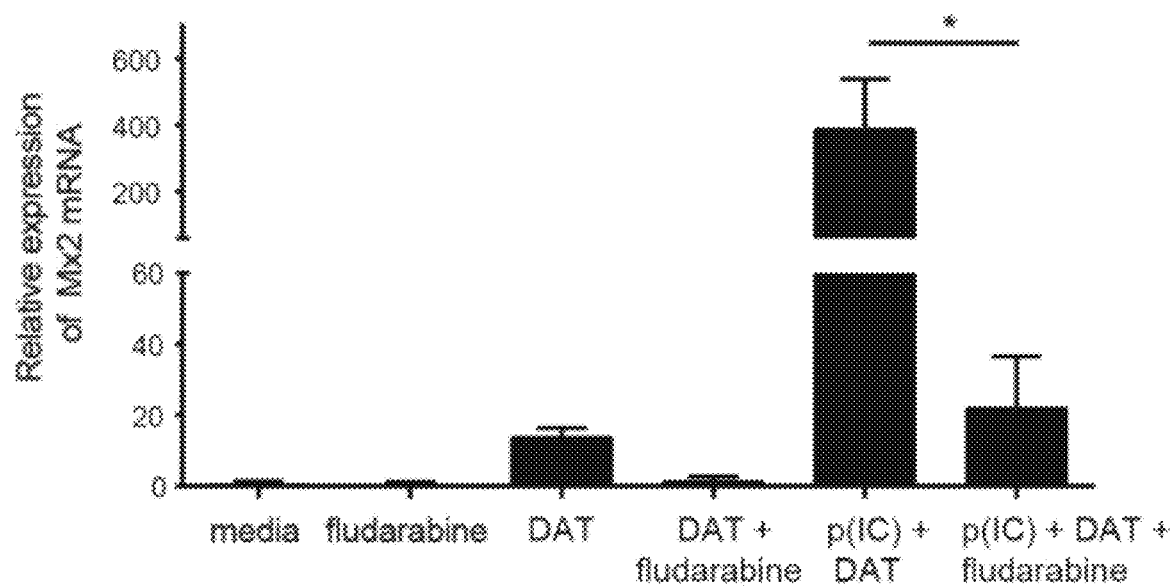
Figure 23C:
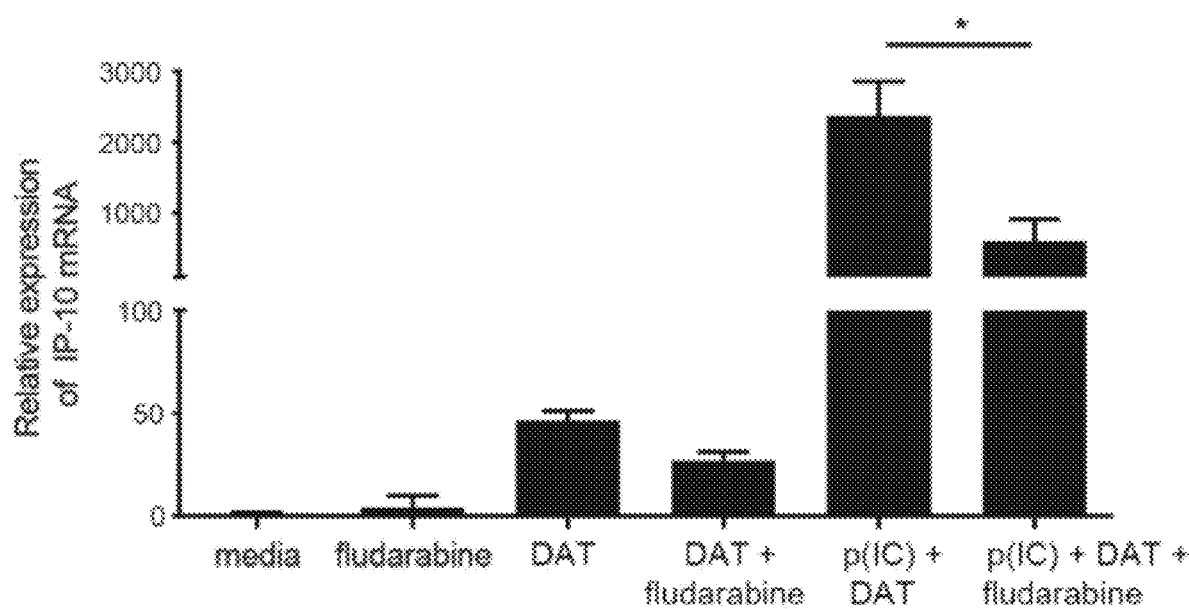

The initial validation of desaminotyrosine did not discern between augmentation of type I IFN induction or type I IFN amplification. To clarify where desaminotyrosine exerts its effects, BMDMs were isolated from mice genetically deficient in key mediators of type I IFN induction and amplification. To query the upstream induction pathway, BMDMs were isolated from Mavs$^{-/-}$ mice and found that desaminotyrosine still enhanced polyIC and type I IFN expression of IP-10 (FIG. 20I, FIG. 20J, FIG. 20K, FIG. 20L, FIG. 20M, and FIG. 20N). Therefore, it was conclude that desaminotyrosine is less likely to act in the induction pathway than in the amplification loop. To confirm this, the role of Stat1, a signaling molecule downstream of Ifnar, was examined. IP-10 expression was not enhanced in similarly treated BMDMs from Stat1$^{-/-}$ mice (FIG. 20I, FIG. 20J, FIG. 20K, FIG. 20L, FIG. 20M, and FIG. 20N). This finding was confirmed with the Stat1 inhibitor, Fludarabine (FIG. 23A, FIG. 23B, and FIG. 23C). Taken together, these findings, without being bound by theory, indicate that desaminotyrosine augmentation of type I IFN signaling is mediated by IFN amplification via Ifnar and Stat1.

Methods for the Examples

Metabolic Screen:

Metabolites were screened using the 2fTGH-ISRE-CBG99 luciferase cell line.[22] The day before screening the reporter cells were plated at 3×104 cell/well in 96 well plates. The following day cells were treated with 100 µM, 10 µM, and 1 µM of metabolite or vehicle control and with or without either IFN-β (PBL Assay Science), poly(IC) (Amersham Biosciences) plus Lyovec (Invivogen) or media control. Luciferase was measured at 14 hours post-treatment for IFN-β, and 24 hours post-treatment for poly(IC) using the STEADYLITE PLUS Reporter Gene assay system (Perkin Elmer) with a 40 minute development time. Plates were read on a luminometer (1 second read time) using the CYTATION 5 (BioTek). For secondary validation, cells were treated with 1000 µM, 100 µM, 10 µM, and 1 µM of metabolite and 5 or 50 U/ml of IFN-β (PBL Assay Science) or 2.5 or 25 pg/ml of poly(IC) (Amersham Biosciences) and measured as above.

In Vivo Treatment of Mice:

All experimental procedures were performed under approval by Washington University's Animal Studies Committee. For experiments with knockout mouse lines, heterozygote breeding pairs were used to obtain littermate controls. All animals were bred at Washington University under specific pathogen-fee conditions. For Influenza A infections, 8-12 week-old male and female mice were anesthetized using isofluorane and injected intranasally with recombinant influenza A/WSN/33 (rWSN) H1N1 virus strain in 40 µL total volume (20 µL per nare). For macrophage depletion survival experiments, animals were injected with 250 µL per mouse of Encapsula's clondronate or control liposomes intraperitoneally 2 days prior to infection, the day of infection, and then on days 2, 5, 8, and 11 postinfection with sacrifice on day 14. For quantification of macrophage depletion, animals were injected with 250 µL per mouse of Encapsula's clondronate or control liposomes intraperitoneally 2 days prior to infection, the day of infection, and then on day 2 postinfection with sacrifice on day 5. Antibiotic treated mice were given the following cocktail for 2 weeks: 500 mg ampicillin, 250 mg vancomycin, 500 mg neomycin-sulfate, 500 mg metronidazole, 10 g grape Kool-Aid in 500 mL water, which was sterile filtered through a 0.22 µm filter and dissolved in Kool-Aid. Control animals received Kool-Aid alone. Desaminotyrosine (200 µM) was added to the drinking water of mice 1 week prior to infection and then continued, 1 week prior to infection only, or 2 days after infection. Deasminotyrosine was added to the antibiotic treatment for indicated groups or to Kool-Aid alone.

Fecal Bacterial Quantification:

Fecal bacterial quantification was estimated using qRT-PCR with the following primers: *C. orbiscindens*: Forward 5'GCACAAGCGGTGGAGT (SEQ ID NO: 1) and Reverse 5'CTTCCTCCGTTTTGTCAA (SEQ ID NO: 2) *C. leptum*: Forward 5' GCACAAGCAGTGGAGT (SEQ ID NO: 3) and Reverse 5'CTTCCTCCGTTTTGTCAA (SEQ ID NO: 4) *E. fecalis*: Forward 5' AGAAATTCCAAACGAACTTG (SEQ ID NO: 5) and Reverse 5' CAGTGCCTCTACCTCCAT-CATT (SEQ ID NO: 6). Clostridia amplification was performed with the following temperature gradient: 94° C. for 5 minutes followed by 40 cycles of 94° C. for 20 seconds, 50° C. for 20 seconds, and 72° C. for 50 seconds, and ended with 7 minutes at 72° C. *Enterococcus* amplification was performed with the following gradient: 95° C. for 2 minutes followed by 40 cycles of 95° C. for 15 seconds and 60° C. for 1 minute, and ended with 7 minutes at 72° C.

Viral Titer Determinations:

To assess lung viral titers, lung tissue was collected in 1 ml of PBS and subject to homogenization in a Roche MagNA Lyser using 1 mm-diameter zirconia/silica beads (BioSpec Products). Plaque assays was performed on MCDK cells with methylcellulose overlay. The limit of detection of the Influenza A plaque assays was 50 pfu/lung tissue or 50 pfu/ml cell supernatant.

Tissue Histology and Staining:

Lungs were inflated with formalin at the time of sacrifice and harvested into formalin containing conical tubes. The following day, the tissue was serially washed in PBS, 30% ethanol, and 50% ethanol and then stored in 70% ethanol until they were processed for paraffin embedding, sectioning, and staining. Cleaved caspase 3 staining was performed with Cell Signaling Technology cleaved caspase 3 antibody Asp175. H1N1 staining was performed with a polyclonal H1N1 antibody, US Biological Influenza A, USSR.[26]

Chemokine and Cytokine Quantification:

Chemokine and cytokine protein quantification was performed using R &D's Proteome Profiler Mouse XL Cytokine Array. Images were quantified with IMAGEJ. Type I IFN Varicella Zoster Virus bioassay was performed as previously described.[27, 26]

RNA Sequencing and Quantification:

RNA was isolated from whole lung homogenates with Trizol Reagent or from cell cultures via NUCLEOSPIN RNA Isolation Kits. For RNA sequencing, RNA library preparation was performed with RIBOZERO and sequencing performed on an ILLUMINA HISEQ 2500 at the Genome Technology Access Center at Washington University.

For directed RNA quantification, cDNA was synthesized using BioRad's ISCRIPT cDNA Synthesis Kit and quantitative PCR was performed with Thermofischer's SYBR-GREEN Master Mix. The following primer pairs were used:

```
Influenza A Matrix Forward
                                   (SEQ ID NO: 7)
5'AAGACCAATCCTGTCACCTCTGA
and Influenza A Matrix Reverse
                                   (SEQ ID NO: 8)
5'CAAAGCGTCTACGCTGCAGTCC, Mx2 Forward
                                   (SEQ ID NO: 9)
5'GAGGCTCTTCAGAATGAGCAAA
and Mx2 Reverse
                                   (SEQ ID NO: 10)
5'CTCTGCGGTCAGTCTCTCT, Oas2 Forward
                                   (SEQ ID NO: 11)
5'TTGAAGAGGAATACATGCGGAAG
and Oas2 Reverse
                                   (SEQ ID NO: 12)
5'GGGTCTGCATTACTGGCACTT,
and GAPDH Forward
                                   (SEQ ID NO: 13)
5'AGGTCGGTGTGAACGGATTTG
and GAPDH Reverse
                                   (SEQ ID NO: 14)
5'TGTAGACCATGTAGTTGAGGTCA.
```

Mass Spectroscopy:

Stool samples were extracted at 100 mg/ml tissue concentration in 80% methanol, then centrifuged for clarification and filtered through an 8 μm PES spin filter. Samples were then subject to a column gradient and analyzed on a Q-EXACTIVE mass spectrometer. Data was then integrated with the QUANBROSWER application of XCALIBUR.

Flavonoid Degradation In Vitro:

$2 \times 10^8$ individual bacteria or 4 mg of pooled cecal contents from 10 wild-type mice was inoculated into 2 ml of Chopped Meat Carbohydrate broth with and without 1.5% quercetin under strict anaerobic conditions. At each time point, an aliquot of the broth was incubated with equal volume solution of 2% $AlCl_3$ dissolved in methanol for 10 minutes to enhance color. Absorbance was measured under 415 nm with a spectrophotometer.

Flow Cytometry:

For determination of in vivo macrophage depletion, lungs were perfused with PBS, harvested, minced with scissors and incubated in DMEM with 350 U/ml collagenase type I (Worthington) and 50 U/ml DNase (Worthington) for 1 hour at 37° C. The remaining tissue after enzymatic digestion was crushed between the rough edge of a frosted microscope slide. The cells were passed through a cell strainer. RBCs were lysed in 1 ml of RBC lysis buffer (Sigma) for 5 minutes at room temperature. The cells were then washed with FACS buffer, blocked, stained with eBiolegend antibodies for CD45, CD64, and CD19. Flow cytometry data analysis was done using FLOJO software (TreeStar).

Bone Marrow Derived Macrophage Generation:

Bone marrow derived macrophages were generated by isolation of bone marrow cells from mouse femurs and tibiae after sacrifice. Cells were incubated in the presence of Sigma's Macrophage Colony-Stimulating Factor at 10 ng/ml for 10 days prior to experimental procedure. Desaminotyrosine (100 μM) was added to the tissue culture media for indicated groups.

Ifnα Quantification:

Type I IFN quantification from serum and lungs was performed by a Type I IFN bioassay as previously described.[30] Neutralizing anti-Ifnar1 antibody (Leinco Technologies, clone #MAR1-5A3) was used to determine Type I IFN specificity. IFNα quantification from cell culture supernatants was performed using PBL BIOLEGEND'S Mouse IFN Alpha Elisa Kit.

Accession Numbers:

RNA sequencing data is available on the Gene Expression Omnibus (GEO).

Statistics:

Data are presented as scatter plots with ±SEM error bars or Kaplan-Mei'er survival curves. GRAPHPAD PRISM (San Diego, Calif.) software was used to perform all statistical analyses unless otherwise specified.

TABLE 1

Irgm1$^{-/-}$ lungs have decreased inflammation and cell death at the RNA level after infection with influenza.
Biological pathways as identified by analysis of RNA sequencing that are differentially expressed in the lungs between wildtype control and Irgm1$^{-/-}$ mice infected with 5,000pfu of WSN 3 days postinfection. Statistical significance determined by multivariate analysis.

| Pathway | Normalized Enrichment Score | Normalize p-value | False Discovery Rate |
|---|---|---|---|
| Interferon alpha response | 2.479 | <0.001 | <0.001 |
| Interferon alpha beta signaling | 2.349 | <0.001 | <0.001 |
| Rig I Mda5 mediated induction of IFN alpha beta pathways | 2.108 | <0.001 | 0.001 |
| Negative regulators of Rig I Mda5 signaling | 1.978 | <0.001 | 0.011 |
| Rig I like receptor signaling pathway | 1.971 | <0.001 | 0.009 |
| Interferon signaling | 1.917 | <0.001 | 0.015 |
| Cytokine signaling in immune system | 1.916 | <0.001 | 0.014 |

TABLE 2

Irgm1$^{-/-}$ lungs have an increased type I Interferon signature.
Biological pathways as identified by analysis of RNA sequencing that are differentially expressed between wildtype control and Irgm1$^{-/-}$ lungs. Statistical significance determined by multivariate analysis.

| Pathway | Normalized Enrichment Score | Normalize p-value | False Discovery Rate |
|---|---|---|---|
| TNFa signaling via NFKB | -2.227 | <0.001 | <0.001 |
| p53 independent DNA damage checkpoint | -2.226 | <0.001 | <0.001 |
| Regulation of apoptosis | -1.952 | <0.001 | 0.006 |
| Inflammatory response | -1.917 | <0.001 | 0.008 |
| p53 dependent DNA damage checkpoint | -1.859 | <0.001 | 0.012 |
| Reactive oxygen species pathway | -1.812 | 0.002 | 0.017 |
| Cytokine signaling in immune system | -1.806 | <0.001 | 0.018 |
| Il-6 Jak Stat3 signaling | -1.774 | <0.001 | 0.021 |
| Toll like receptor signaling pathway | -1.723 | <0.001 | 0.03 |
| Il-1 signaling | -1.677 | 0.006 | 0.04 |

Figure 13A:
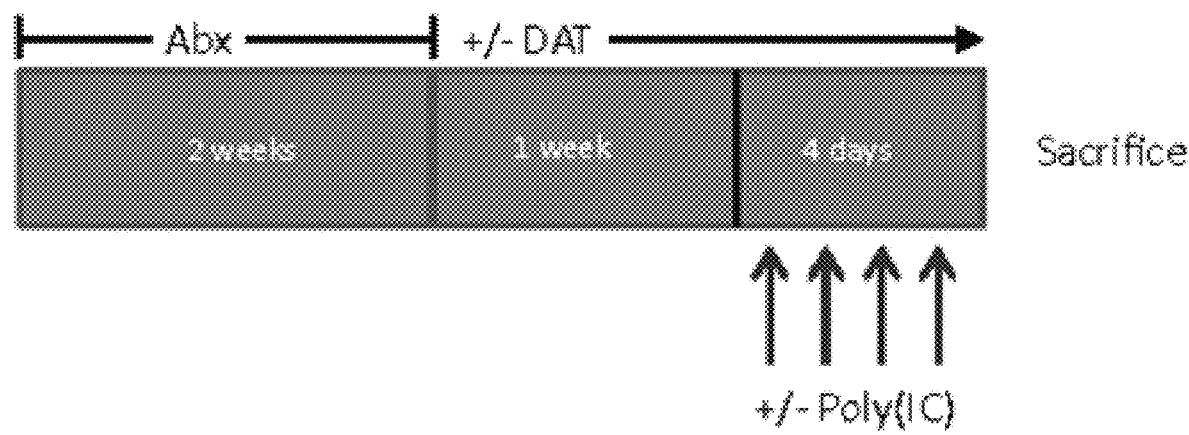
FIG. 13 depicts an experimental scheme of mice treated with VNAM for 2 weeks and then give +/−200 mM desaminotyrosine in the drinking water for 1 week. After 1 week, the mice were continued on +/−200 mM desaminotyrosine and then treated with +/−1 mg/kg polyIC intraperitoneally once per day for 4 days and then sacrificed 1 day later.
Figure 13F:
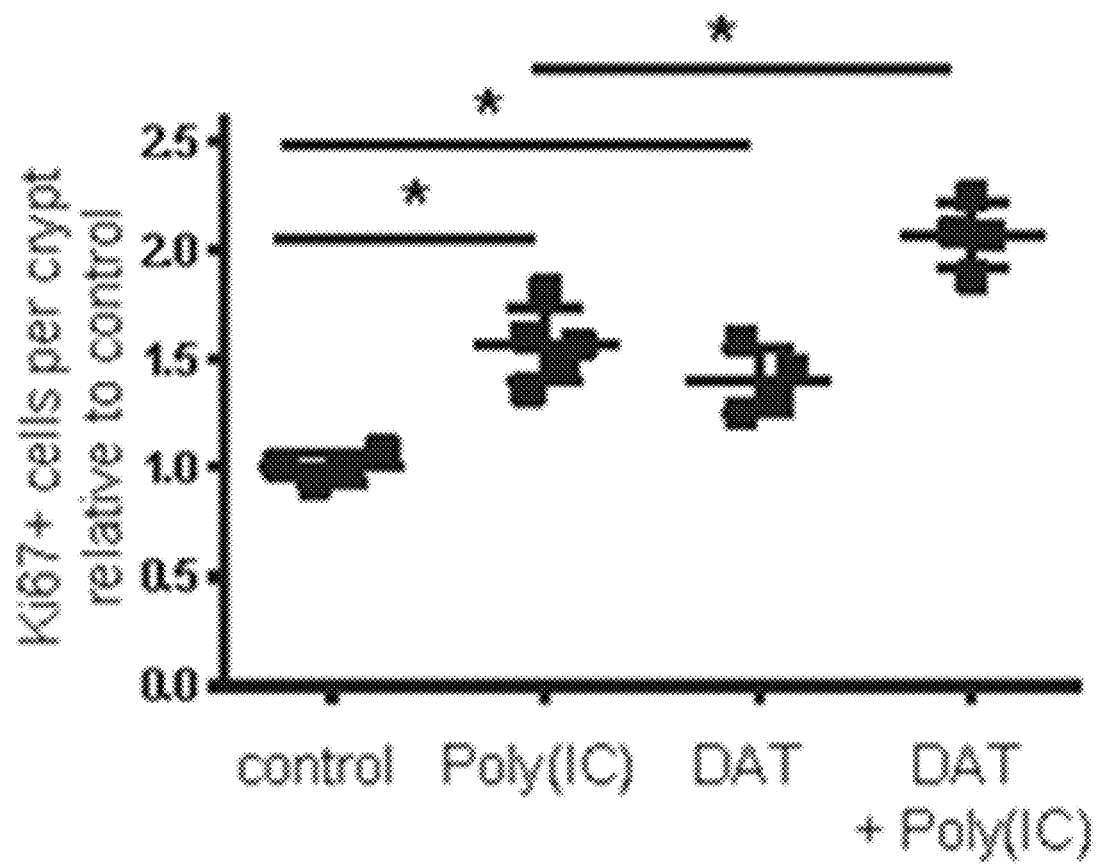
Figure 14E:
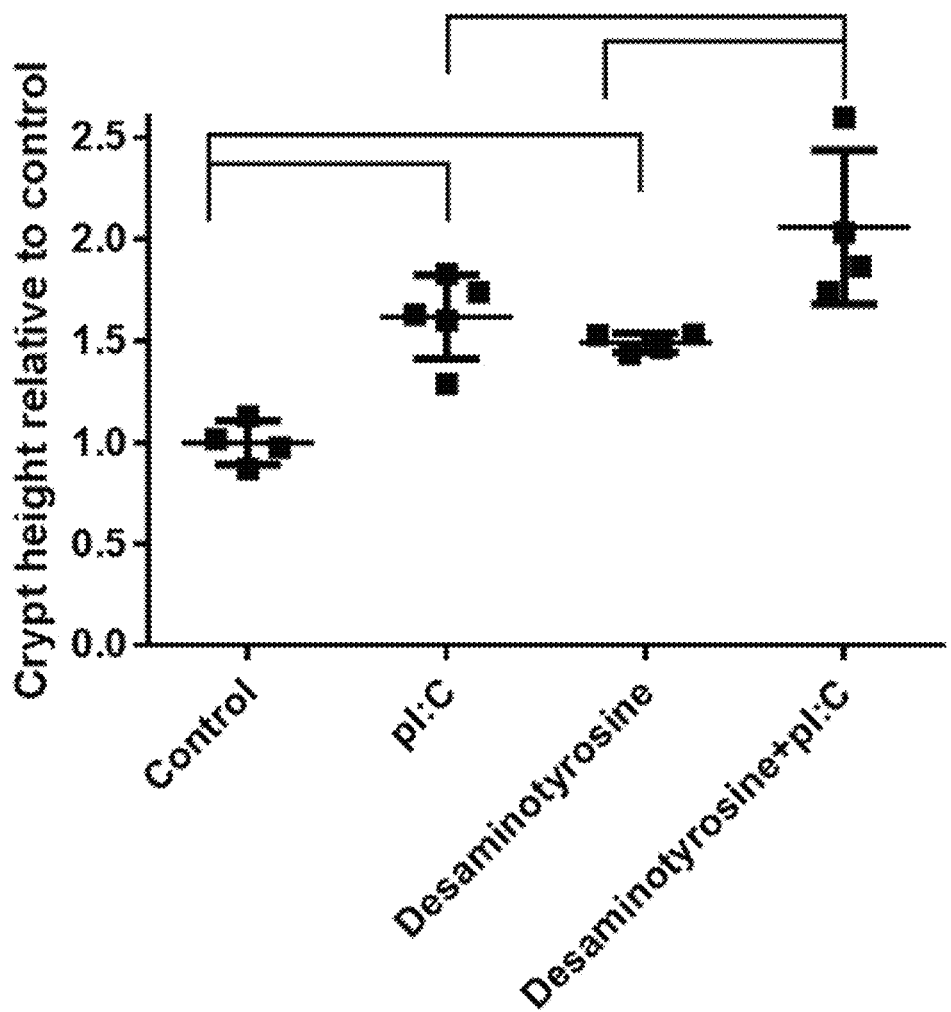

Example 2. Desaminotyrosine Increases Epithelial Proliferation and Treats Dextran Sodium Sulfate (DSS) Induced Colitis To examine the effects of desaminotyrosine on epithelial proliferation, mice were treated with and without antibiotics for 2 weeks and then with or without desaminotyrosine for 2 weeks and with or without polyIC (FIG. 13). Results showed that desaminotyrosine treatment increases crypt height and epithelial proliferation (FIG. 14A, FIG. 14B, FIG. 14C, FIG. 14D, and FIG. 14E). Further, It can be seen that desaminotyrosine stimulated epithelia proliferation in the small intestine alone and, without being bound by theory, in a synergistic fashion with polyIC (FIG. 14A, FIG. 14B, FIG. 14C, FIG. 14D, and FIG. 14E).

Figure 15A:
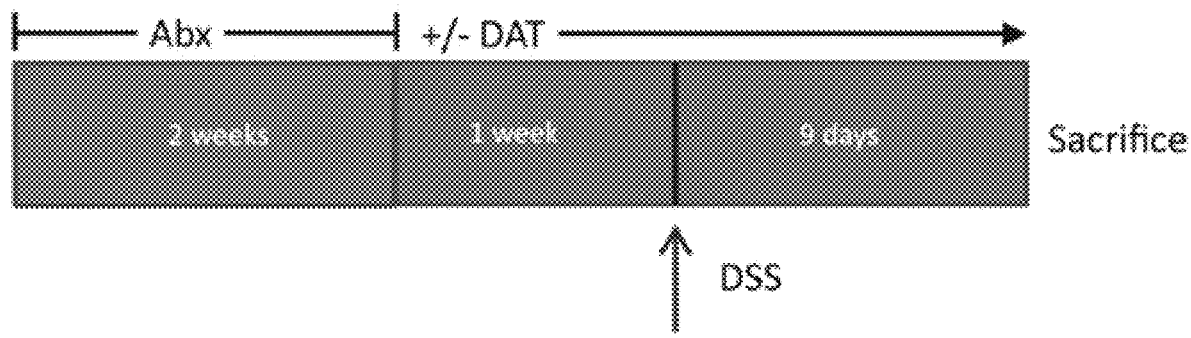
FIG. 15A depicts a schematic of the experimental design to test the effects of desaminotyrosine on DSS-induced colitis, mice were treated with VNAM for 2 weeks and then give +/−200 mM desaminotyrosine in the drinking water for 1 week prior to additional treatment with +/−2.5% DSS treatment.
Figure 15B:
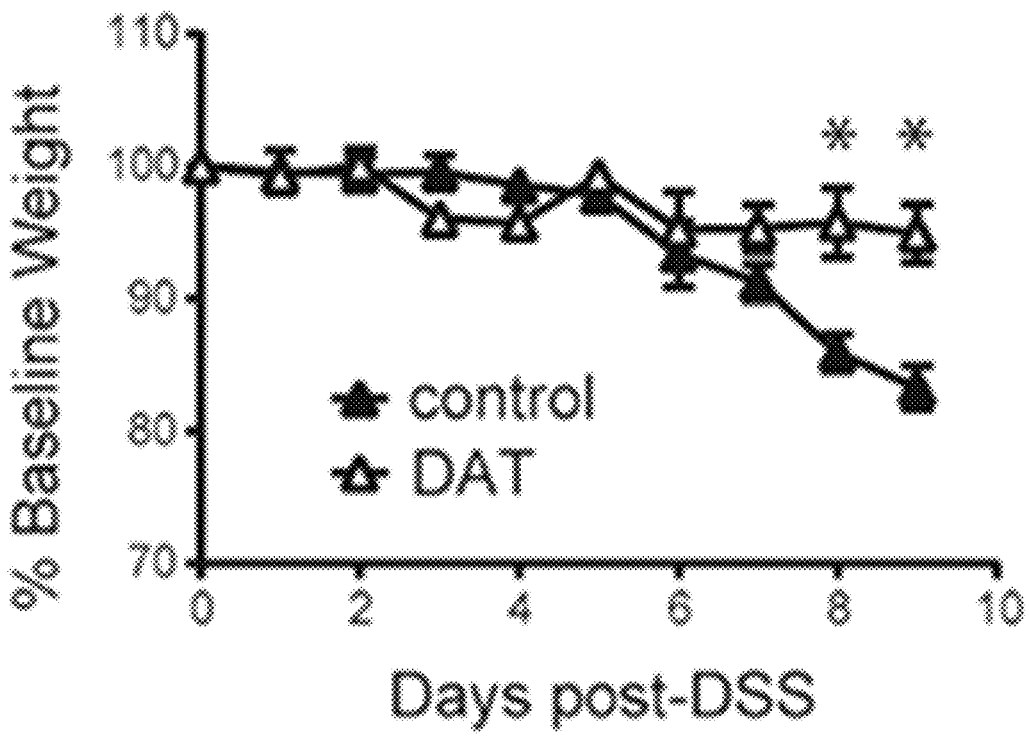
(FIG. 15B) Weight loss of WT mice treated as shown in FIG. 15A (n=20 mice in control group, 10 mice in desaminotyrosine group from 2 experiments).
Figure 15C:
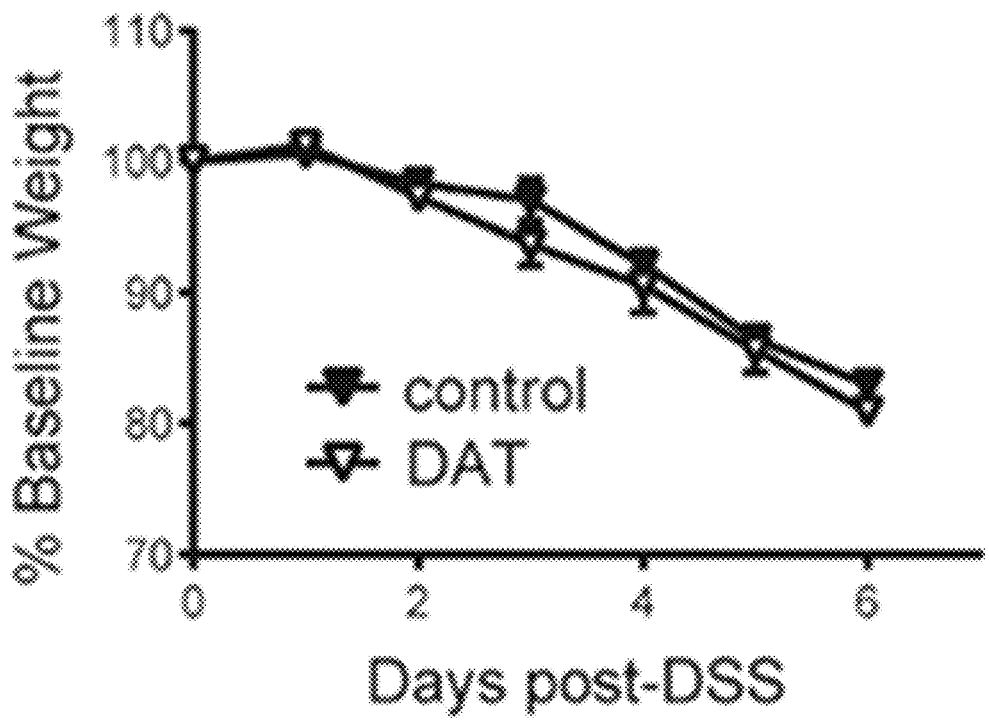
(FIG. 15C) Weight loss of Ifnar mice treated as shown in FIG. 15A with the exception of mice were sacrificed on day 6 post-DSS treatment due to morbidity (n=13-14 mice per group from 2 experiments).
Figure 15D:
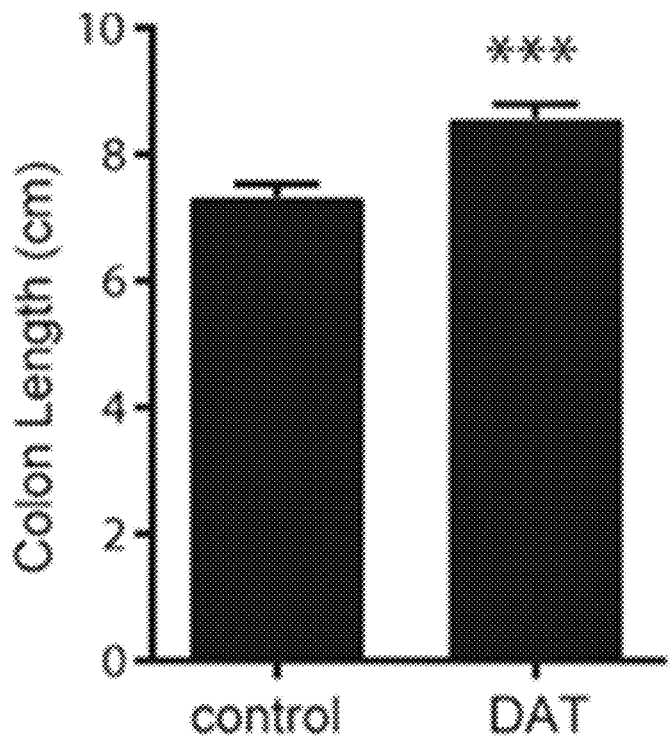
(FIG. 15D) Colon length of VVT mice on day of sacrifice.
Figure 15E:
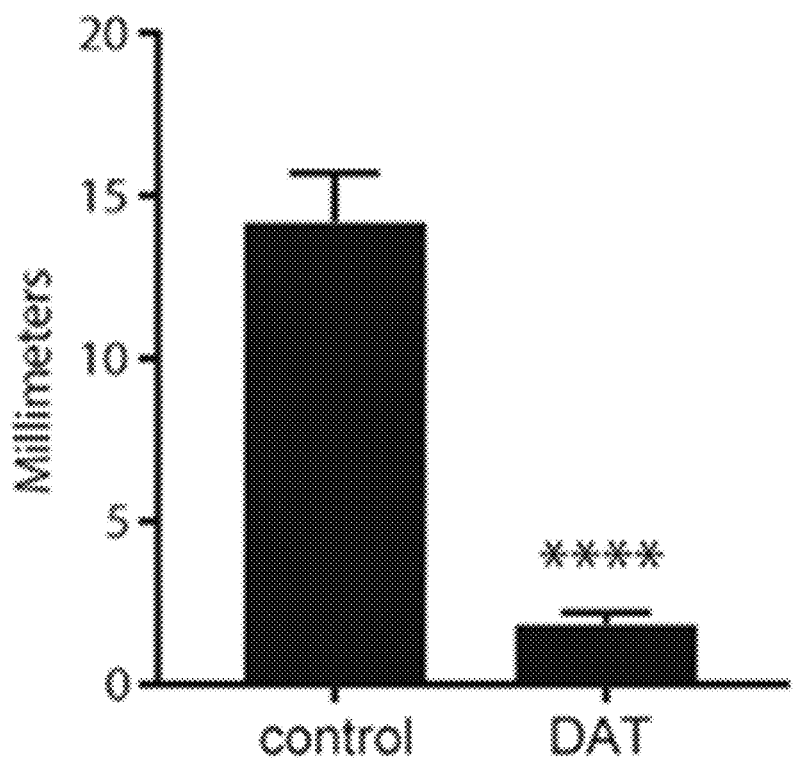
(FIG. 15E) Distance from anorectal junction to crypt containing areas in the rectum. (n=8-10 WT mice per group) *p<0.05 by multivariate analysis, *p<0.001 by Mann-Whitney test, and **p<0.0001 by Mann-Whitney test.
Figure 16A:
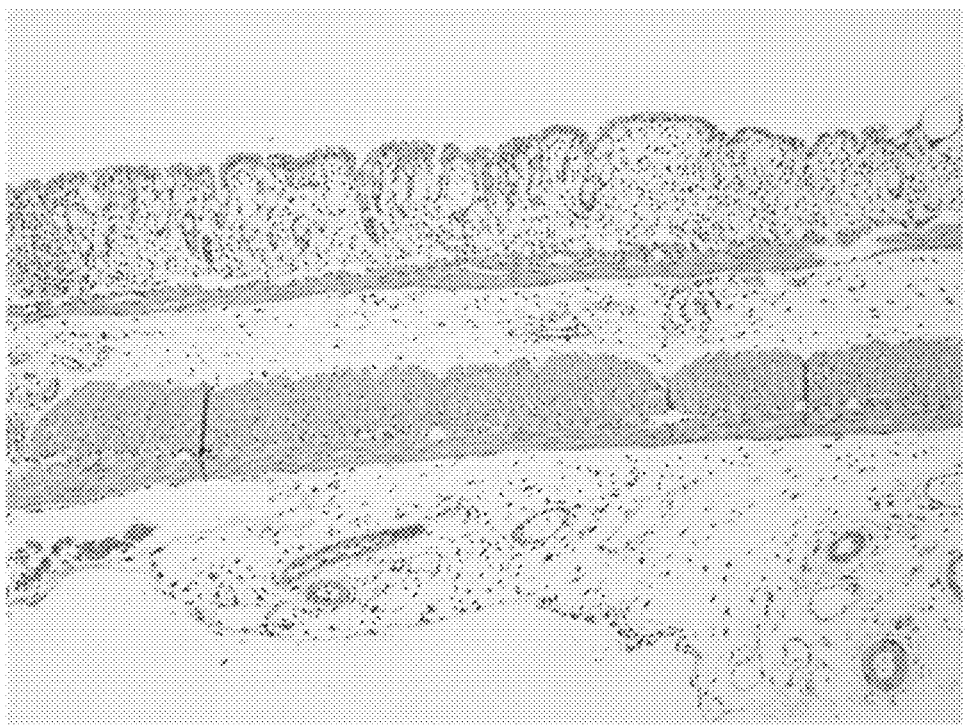
FIG. 16A and FIG. 16B depict images showing that desaminotyrosine rescues DSS damage in antibiotic treated mice.
Figure 16B:
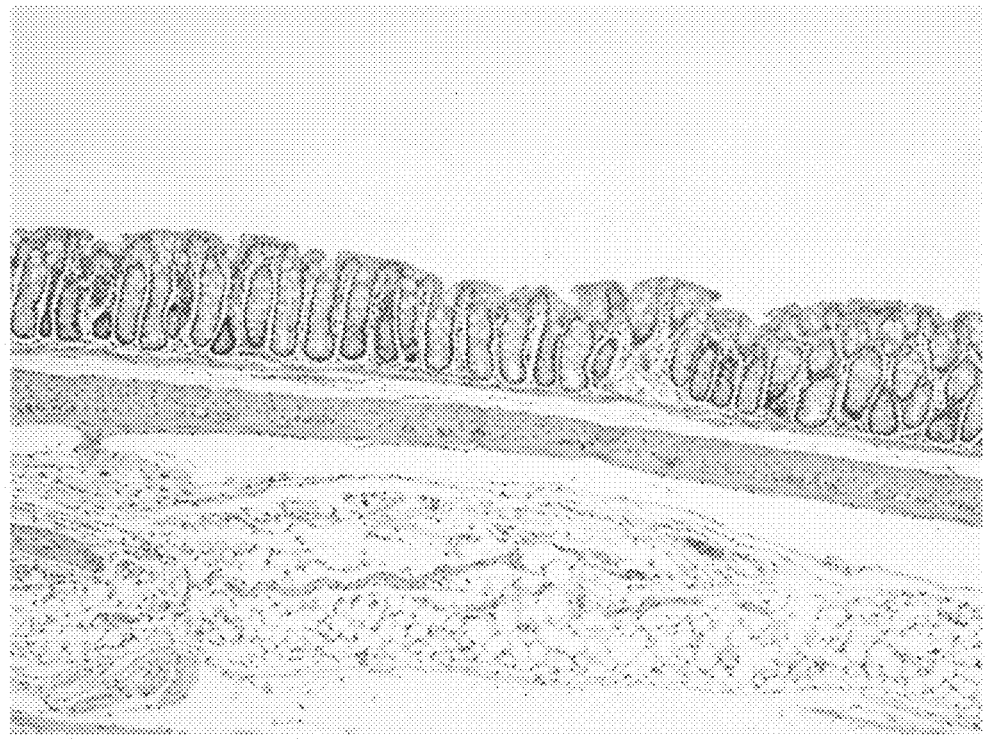
Figure 17A:
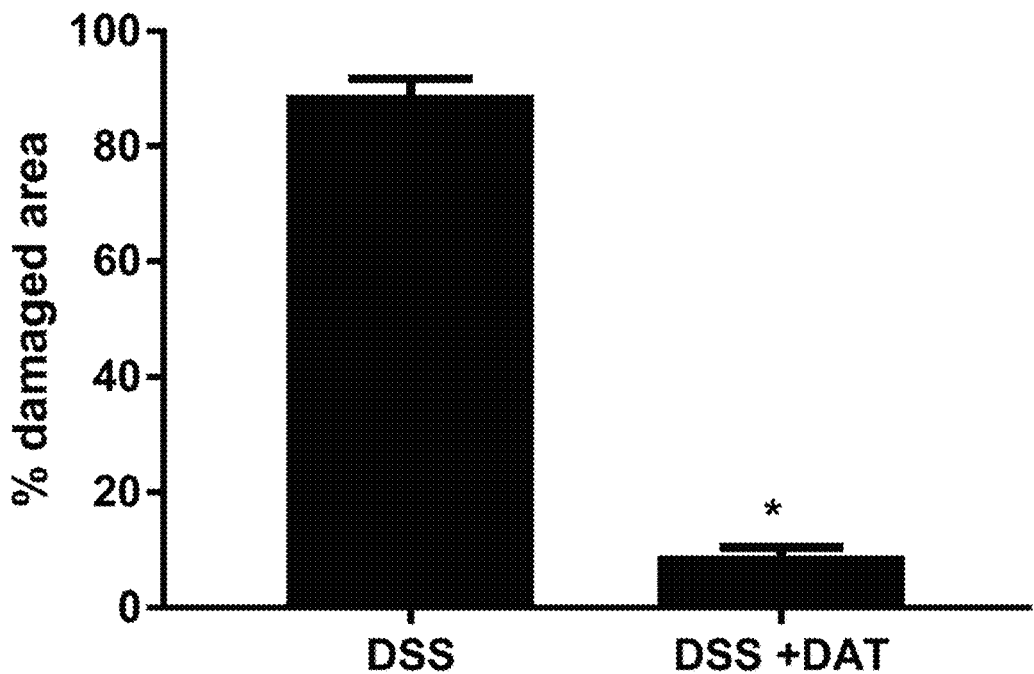
FIG. 17A depicts a graph quantifying the amount of damaged area following treatment with DSS +/−desaminotyrosine.
Figure 17B:
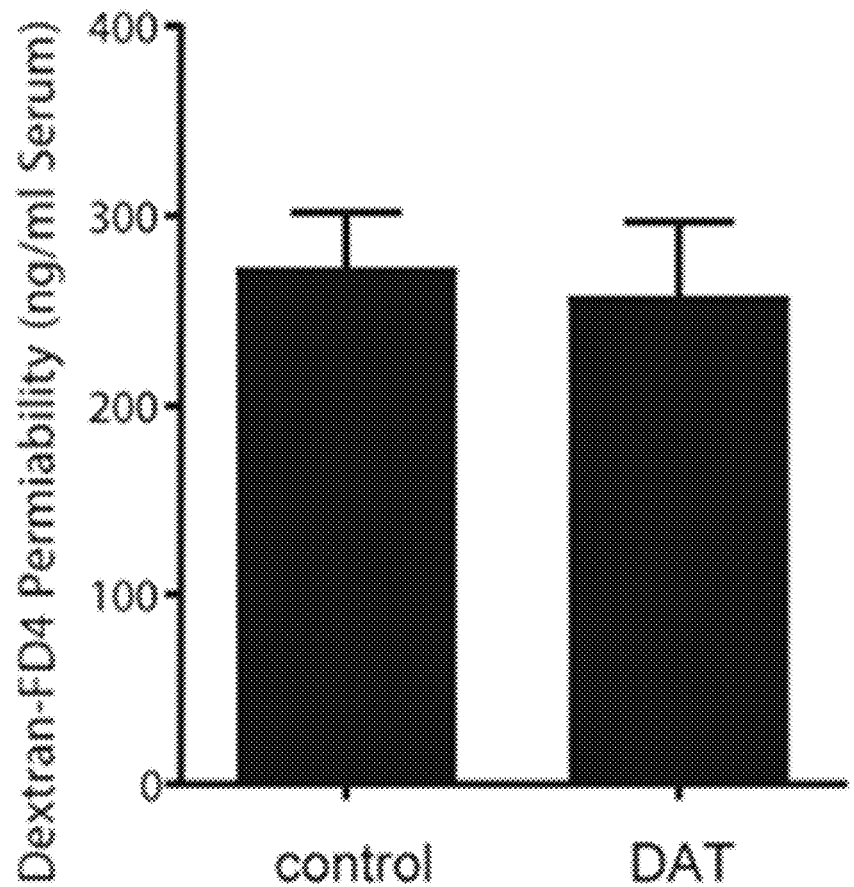
FIG. 17B depicts a graph dextrain-FD4 measured in the serum of mice treated with VNAM for 2 weeks and then +/−200 mM of desaminotyrosine for 1 week in the drinking water. 4 kD Dextran was administered by gavage and serum collected 4 hours post-gavage. (n=5 mice per group) Not significant by Mann-Whitney test.

Next, the effects of desaminotyrosine on dextran sodium sulfate (DSS) induced colitis were examined. Mice were treated with antibiotics for 2 weeks then with or without desaminotyrosine for 2 weeks in the presence of 2.5% DSS (FIG. 15B and FIG. 15C). Results showed that desaminotyrosine is beneficial in the response to DSS injury as it promoted epithelial profliferation and crypt preservation (FIG. 15B, FIG. 15C, FIG. 15D, and FIG. 15E). Results also showed that desaminotyrosine rescues DSS damage in antibiotic treated mice. In control mice, not treated with desaminotyrosine, nearly all crypts (~90%) were destroyed in the distal colon after DSS treatment (FIG. 16A). However, in mice treated with desaminotyrosine, only minimal areas (~8%) of damage in the distal colon were observed after DSS treatment (FIG. 16B). Additionally, results showed that the oral dose of desaminotyrosine provides protection from influenza had no effect on barrier function (FIG. 17A and FIG. 17B).

REFERENCES FOR THE EXAMPLES

1 Platanias, L. C. Mechanisms of type-I- and type-II-interferon-mediated signalling. *Nat Rev Immunol* 5, 375-386, doi: 10.1038/nri1604 (2005).

2 Honda, K. et al. IRF-7 is the master regulator of type-I interferon-dependent immune responses. *Nature* 434, 772-777, doi:10.1038/nature03464 (2005).

3 Kolumam, G. A., Thomas, S., Thompson, L. J., Sprent, J. & Murali-Krishna, K. Type I interferons act directly on CD8 T cells to allow clonal expansion and memory formation in response to viral infection. *J Exp Med* 202, 637-650, doi: 10.1084/jem.20050821 (2005).

4 Nguyen, K. B. et al. Coordinated and distinct roles for IFN-alpha beta, IL-12, and IL-15 regulation of NK cell responses to viral infection. *Journal of Immunology* 169, 4279-4287 (2002).

Davidson, S., Crotta, S., McCabe, T. M. & Wack, A. Pathogenic potential of interferon alphabeta in acute influenza infection. *Nat Commun* 5, 3864, doi:10.1038/ncomms4864 (2014).

6 Koerner, I., Kochs, G., Kalinke, U., Weiss, S. & Staeheli, P. Protective role of beta interferon in host defense against influenza A virus. *J Virol* 81, 2025-2030, doi:10.1128/JVI.01718-06 (2007).

7 Arimori, Y. et al. Type I interferon limits influenza virus-induced acute lung injury by regulation of excessive inflammation in mice. *Antiviral Res* 99, 230-237, doi: 10.1016/j.antiviral.2013.05.007 (2013).

8 Hogner, K. et al. Macrophage-expressed IFN-beta contributes to apoptotic alveolar epithelial cell injury in severe influenza virus pneumonia. *PLoS Pathog* 9, e1003188, doi:10.1371/journal.ppat. 1003188 (2013).

9 Billiau, A. Anti-inflammatory properties of Type I interferons. *Antivir Res* 71, 108-116, doi: 10.1016/j.antiviral.2006.03.006 (2006).

Gonzalez-Navajas, J. M., Lee, J., David, M. & Raz, E. Immunomodulatory functions of type I interferons. *Nat Rev Immunol* 12, 125-135, doi:10.1038/nri3133 (2012).

11 Guarda, G. et al. Type I interferon inhibits interleukin-1 production and inflammasome activation. *Immunity* 34, 213-223, doi:10.1016/j. immuni.2011.02.006 (2011).

12 Sun, L. et al. Type I interferons link viral infection to enhanced epithelial turnover and repair. *Cell Host Microbe* 17, 85-97, doi:10.1016/j.chom.2014.11.004 (2015).

13 Kernbauer, E., Ding, Y. & Cadwell, K. An enteric virus can replace the beneficial function of commensal bacteria. *Nature* 516, 94-98, doi:10.1038/nature13960 (2014).

14 Ichinohe, T. et al. Microbiota regulates immune defense against respiratory tract influenza A virus infection. *Proc Natl Acad Sci USA* 108, 5354-5359, doi: 10.1073/pnas. 1019378108 (2011).

Abt, M. C. et al. Commensal bacteria calibrate the activation threshold of innate antiviral immunity. *Immunity* 37, 158-170, doi:10.1016/j.immuni.2012.04.011 (2012).

16 Wang, J. et al. Bacterial colonization dampens influenza-mediated acute lung injury via induction of M2 alveolar macrophages. *Nat Commun* 4, 2106, doi:10.1038/ncomms3106 (2013).

17 Kaiko, G. E. et al. The Colonic Crypt Protects Stem Cells from Microbiota-Derived Metabolites. *Cell* 165, 1708-1720, doi:10.1016/j.cell.2016.05.018 (2016).

18 Ryu, S. H. & Stappenbeck, T. S. Gut-Pancreatic Axis AMPlified in Islets of Langerhans. *Immunity* 43, 216-218, doi: 10.1016/j.immuni.2015.08.003 (2015).

19 Trompette, A. et al. Gut microbiota metabolism of dietary fiber influences allergic airway disease and hematopoiesis. *Nat Med* 20, 159-166, doi:10.1038/nm.3444 (2014).

Smith, P. M. et al. The microbial metabolites, short-chain fatty acids, regulate colonic Treg cell homeostasis. *Science* 341, 569-573, doi:10.1126/science.1241165 (2013).

21 Matsumoto, M. et al. Impact of intestinal microbiota on intestinal luminal metabolome. *Sci Rep* 2, 233, doi: 10.1038/srep00233 (2012).

22 Patel, D. A., Patel, A. C., Nolan, W. C., Zhang, Y. & Holtzman, M. J. High throughput screening for small molecule enhancers of the interferon signaling pathway to drive next-generation antiviral drug discovery. *PLoS One* 7, e36594, doi: 10.1371/journal. pone.0036594 (2012).

23. Zhang, Z., Peng, X., Li, S., Zhang, N., Wang, Y., Wei, H., Isolation and identification of quercetin degrading bacteria from human fecal microbes. *PLoS One* 9, e90531 (2014)10.1371/journal.pone.0090531).

24. Schoefer, L., Mohan, R., Schwiertz, A., Braune, A., Blaut, M., Anaerobic degradation of flavonoids by *Clostridium orbiscindens*. *Appl Environ Microbiol* 69, 5849-5854 (2003); published online EpubOct.

25. Stevens, V. W., Nelson, R. E., Schwab-Daugherty, E. M., Khader, K., M. M. Jones, M. M., Brown, K. A., Greene, T., Croft, L. D., Neuhauser, M., Glassman, P., Goetz, M. B., Samore, M. H., Rubin, M. A., Comparative Effectiveness of Vancomycin and Metronidazole for the Prevention of Recurrence and Death in Patients With *Clostridium difficile* Infection. *JAMA Internal Medicine* 177, 546-553 (2017); published online EpubApr 01 (10.1001/jamainternmed.2016.9045).

26. Boon, A., C., deBeauchamp, J., Hollmann, A., Luke, J., Kotb, M., Rowe, S., Finkelstein, D., Neale, G., Lu, L., Williams, R. W., Webby, R. J., Host genetic variation affects resistance to infection with a highly pathogenic H5N1 influenza A virus in mice. *J Virol* 83, 10417-10426 (2009); published online EpubOct (10.1128/JVI.00514-09).

27. Sun, L., Miyoshi, H., Origanti, S., Nice, T. J., Barger, A. C., Manieri, N. A., Fogel, L. A., French, A. R., Piwnica-Worms, D., Piwnica-Worms, H., Virgin, H. W., Lenschow, D. J., Stappenbeck, T. S., Type I interferons link viral infection to enhanced epithelial turnover and repair. *Cell Host Microbe* 17, 85-97 (2015); published online EpubJan 14 (10.1016/j.chom.2014.11.004).

28. Byrne, A. J., Mathie, S. A., Gregory, L. G., Lloyd, C. M., Pulmonary macrophages: key players in the innate defence of the airways. *Thorax* 70, 1189-1196 (2015); published online EpubDec (10.1136/thoraxjnl-2015-207020).

29. van Rooijen, N., van Nieuwmegen, R., Elimination of phagocytic cells in the spleen after intravenous injection of liposome-encapsulated dichloromethylene diphosphonate. An enzyme-histochemical study. *Cell and tissue research* 238, 355-358 (1984).

30. Newby, C. M., Sabin, L. & Pekosz, A. The RNA binding domain of influenza A virus NS1 protein affects secretion of tumor necrosis factor alpha, interleukin-6, and interferon in primary murine tracheal epithelial cells. *J Virol* 81, 9469-9480, doi:10.1128/JVI.00989-07 (2007).

---

What is claimed is:

1. A method to prevent or reduce influenza-associated symptoms in a subject in need thereof, the method comprising administering to the subject a composition comprising desaminotyrosine, wherein the desaminotyrosine has the following structure:

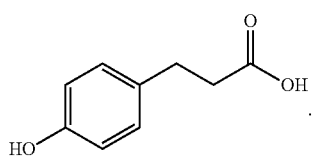 [SMILES: O=C(O)CCc1ccc(O)cc1]

2. The method of claim 1, wherein the composition is administered prophylactically and wherein type I interferon stimulation is enhanced in the subject.

3. The method of claim 1, wherein the subject is at a high risk for complications from influenza.

4. A method to promote epithelial tissue proliferation in a subject, the method comprising administering to the subject a composition comprising desaminotyrosine, wherein the desaminotyrosine has the following structure:

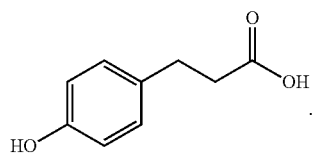 [SMILES: O=C(O)CCc1ccc(O)cc1]

5. The method of claim 4, wherein the epithelial tissue is selected from the group consisting of skin, mouth, esophagus, lungs, gastrointestinal tract, reproductive tract, urinary tract, exocrine glands, and endocrine glands.

6. The method of claim 5, wherein the epithelial tissue is the gastrointestinal tract.

7. The method of claim 5, wherein the epithelial tissue is located in the colon.

8. The method of claim 7, wherein the desaminotyrosine restores or increases crypt height.

9. A method to promote wound repair in a subject, the method comprising administering to the subject a composition comprising desaminotyrosine, wherein the desaminotyrosine has the following structure:

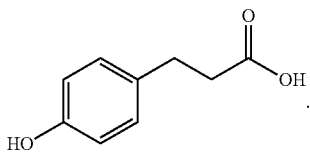 [SMILES: O=C(O)CCc1ccc(O)cc1]

10. The method of claim 9, wherein the wound is due to surgery, injury and/or inflammation.

11. The method of claim 9, wherein the wound is at a mucosal site.

12. The method of claim 9, wherein the wound is located in the gastrointestinal tract.

13. The method of claim 12, wherein the desaminotyrosine restores the normal structure of the epithelium.

14. The method of claim 8, wherein the subject has colitis.

15. The method of claim 14, wherein the colitis is inflammatory bowel disease.

16. The method of claim 15, wherein the inflammatory bowel disease is ulcerative colitis or Crohn's disease.

17. The method of claim 6, further comprising administering polyIC.

18. The method of claim 4, wherein type I interferon stimulation is enhanced in the subject.

19. The method of claim 9, wherein type I interferon stimulation is enhanced in the subject.

* * * * *

SEQUENCE LISTING

```
<160> NUMBER OF SEQ ID NOS: 14

<210> SEQ ID NO 1
<211> LENGTH: 16
<212> TYPE: DNA
<213> ORGANISM: Artificial Sequence
<220> FEATURE:
<223> OTHER INFORMATION: SYNTHESIZED

<400> SEQUENCE: 1
gcacaagcgg tggagt                                                     16

<210> SEQ ID NO 2
<211> LENGTH: 18
<212> TYPE: DNA
<213> ORGANISM: Artificial Sequence
<220> FEATURE:
<223> OTHER INFORMATION: SYNTHESIZED

<400> SEQUENCE: 2
cttcctccgt tttgtcaa                                                   18

<210> SEQ ID NO 3
<211> LENGTH: 16
<212> TYPE: DNA
<213> ORGANISM: Artificial Sequence
<220> FEATURE:
```

<223> OTHER INFORMATION: SYNTHESIZED

<400> SEQUENCE: 3
gcacaagcag tggagt                                                    16

<210> SEQ ID NO 4
<211> LENGTH: 18
<212> TYPE: DNA
<213> ORGANISM: Artificial Sequence
<220> FEATURE:
<223> OTHER INFORMATION: SYNTHESIZED

<400> SEQUENCE: 4
cttcctccgt tttgtcaa                                                  18

<210> SEQ ID NO 5
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 5
agaaattcca aacgaacttg                                                20

<210> SEQ ID NO 6
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 6
cagtgcctct acctccatca tt                                             22

<210> SEQ ID NO 7
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 7
aagaccaatc ctgtcacctc tga                                            23

<210> SEQ ID NO 8
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 8
caaagcgtct acgctgcagt cc                                             22

<210> SEQ ID NO 9
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 9
gaggctcttc agaatgagca aa                                             22

```
<210> SEQ ID NO 10
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 10
ctctgcggtc agtctctct                                                    19

<210> SEQ ID NO 11
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 11
ttgaagagga atacatgcgg aag                                               23

<210> SEQ ID NO 12
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 12
gggtctgcat tactggcact t                                                 21

<210> SEQ ID NO 13
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 13
aggtcggtgt gaacggattt g                                                 21

<210> SEQ ID NO 14
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 14
tgtagaccat gtagttgagg tca                                               23
```